(12) United States Patent
Tofail et al.

(10) Patent No.: US 9,103,006 B2
(45) Date of Patent: Aug. 11, 2015

(54) NICKEL-TITANIUM ALLOY INCLUDING A RARE EARTH ELEMENT

(75) Inventors: Syed Ansar Md. Tofail, Limerick (IE); James M. Carlson, Bloomington, IN (US); Shane Carr, Kilcar (IE); Paul Devereux, Leopardstown Valley (IE); Donncha Haverty, Castletroy (IE); Shay J. Lavelle, Annacotty (IE); Tim McGloughlin, Ballyclough (IE)

(73) Assignee: Cook Medical Technologies LLC, Bloomington, IN (US)

( * ) Notice: Subject to any disclaimer, the term of this patent is extended or adjusted under 35 U.S.C. 154(b) by 671 days.

(21) Appl. No.: 11/899,420

(22) Filed: Sep. 6, 2007

(65) Prior Publication Data

US 2008/0053577 A1     Mar. 6, 2008

Related U.S. Application Data

(60) Provisional application No. 60/842,484, filed on Sep. 6, 2006, provisional application No. 60/872,369, filed on Nov. 29, 2006, provisional application No. 60/872,370, filed on Nov. 29, 2006.

(51) Int. Cl.
| | |
|---|---|
| *C22C 19/03* | (2006.01) |
| *C22C 12/00* | (2006.01) |
| *C22C 30/00* | (2006.01) |
| *C22C 1/02* | (2006.01) |
| *C22C 14/00* | (2006.01) |
| *C22C 19/05* | (2006.01) |

(Continued)

(52) U.S. Cl.
CPC .............. *C22C 30/00* (2013.01); *C22C 1/023* (2013.01); *C22C 14/00* (2013.01); *C22C 19/03* (2013.01); *C22C 19/05* (2013.01); *C22F 1/10* (2013.01); *C22F 1/18* (2013.01)

(58) Field of Classification Search
None
See application file for complete search history.

(56) References Cited

U.S. PATENT DOCUMENTS

| | | | |
|---|---|---|---|
| 5,069,226 | A | 12/1991 | Yamauchi et al. |
| 5,230,348 | A | 7/1993 | Ishibe et al. |
| 5,636,641 | A | 6/1997 | Fariabi |

(Continued)

FOREIGN PATENT DOCUMENTS

| | | |
|---|---|---|
| EP | 0873734 A2 | 10/1998 |
| JP | 48 066521 A | 9/1973 |

(Continued)

OTHER PUBLICATIONS

International Search Report and the Written Opinion for International Patent Application No. PCT/US2007/019445 dated Dec. 14, 2007.

(Continued)

*Primary Examiner* — Yoshitoshi Takeuchi
(74) *Attorney, Agent, or Firm* — Brinks Gilson & Lione

(57) ABSTRACT

Disclosed herein is a nickel-titanium alloy comprising nickel, titanium, and at least one rare earth element. The nickel-titanium alloy comprises from about 34 at. % to about 60 at. % nickel, from about 34 at. % to about 60 at. % titanium, and from about 0.1 at. % to about 15 at. % at least one rare earth element. The nickel-titanium alloy may further include one or more additional alloying elements. In addition to radiopacity, the nickel-titanium alloy preferably exhibits superelastic or shape memory behavior. Medical devices comprising the nickel-titanium alloy and a method of making them are also disclosed.

20 Claims, 21 Drawing Sheets

(51) Int. Cl.
C22F 1/10 (2006.01)
C22F 1/18 (2006.01)

(56) References Cited

U.S. PATENT DOCUMENTS

| | | | |
|---|---|---|---|
| 5,637,089 A | 6/1997 | Abrams et al. | |
| 5,641,364 A | 6/1997 | Golberg et al. | |
| 5,885,381 A | 3/1999 | Mitose et al. | |
| 5,927,345 A | 7/1999 | Samson | |
| 5,951,793 A | 9/1999 | Mitose et al. | |
| 6,077,368 A * | 6/2000 | Nakamura et al. | 148/563 |
| 6,165,292 A | 12/2000 | Abrams et al. | |
| 6,277,084 B1 | 8/2001 | Abele et al. | |
| 6,312,454 B1 | 11/2001 | Stöckel et al. | |
| 6,312,455 B2 | 11/2001 | Duerig et al. | |
| 6,325,824 B2 | 12/2001 | Limon | |
| 6,352,515 B1 | 3/2002 | Anderson et al. | |
| 6,375,458 B1 | 4/2002 | Moorleghem et al. | |
| 6,399,886 B1 | 6/2002 | Avellanet | |
| 6,461,453 B1 | 10/2002 | Abrams et al. | |
| 6,482,166 B1 | 11/2002 | Fariabi | |
| 6,497,709 B1 | 12/2002 | Heath | |
| 6,557,993 B2 | 5/2003 | Rossin | |
| 6,569,194 B1 | 5/2003 | Pelton | |
| 6,572,646 B1 | 6/2003 | Boylan et al. | |
| 6,602,228 B2 | 8/2003 | Nanis et al. | |
| 6,626,937 B1 | 9/2003 | Cox | |
| 6,682,608 B2 | 1/2004 | Abrams et al. | |
| 6,706,053 B1 | 3/2004 | Boylan et al. | |
| 6,776,795 B2 | 8/2004 | Pelton | |
| 6,827,734 B2 | 12/2004 | Fariabi | |
| 6,830,638 B2 | 12/2004 | Boylan et al. | |
| 6,855,161 B2 | 2/2005 | Boylan et al. | |
| 6,884,234 B2 | 4/2005 | Aita et al. | |
| 7,128,757 B2 | 10/2006 | Boylan et al. | |
| 7,192,496 B2 | 3/2007 | Wojcik | |
| 7,244,319 B2 | 7/2007 | Abrams et al. | |
| 7,258,753 B2 | 8/2007 | Abrams et al. | |
| 7,462,192 B2 | 12/2008 | Norton et al. | |
| 7,641,983 B2 | 1/2010 | Stinson | |
| 2002/0082681 A1 * | 6/2002 | Boylan et al. | 623/1.19 |
| 2003/0120181 A1 | 6/2003 | Toma et al. | |
| 2003/0193314 A1 * | 10/2003 | Solingen | 320/107 |
| 2004/0143317 A1 | 7/2004 | Stinson et al. | |
| 2004/0220608 A1 | 11/2004 | D'Aquanni et al. | |
| 2004/0236409 A1 | 11/2004 | Pelton et al. | |
| 2004/0249447 A1 | 12/2004 | Boylan et al. | |
| 2005/0038500 A1 | 2/2005 | Boylan et al. | |
| 2005/0131522 A1 | 6/2005 | Stinson et al. | |
| 2005/0209683 A1 | 9/2005 | Yamauchi et al. | |
| 2006/0129166 A1 | 6/2006 | Lavelle | |
| 2006/0222844 A1 | 10/2006 | Stinson | |
| 2007/0249965 A1 | 10/2007 | Abrams et al. | |
| 2008/0114449 A1 | 5/2008 | Gregorich et al. | |

FOREIGN PATENT DOCUMENTS

| | | | | |
|---|---|---|---|---|
| JP | 58-157935 | * | 9/1983 | C22C 19/03 |
| JP | 58 157935 A | | 9/1983 | |
| JP | 59 104459 A2 | | 6/1984 | |
| JP | 61 210142 A2 | | 9/1986 | |
| JP | 62 007839 A2 | | 1/1987 | |
| JP | 9-137241 | | 5/1997 | |
| JP | EP 0783040 | * | 7/1997 | C22C 19/00 |
| WO | WO 01/72349 A1 | | 10/2001 | |
| WO | WO 02/051462 A2 | | 7/2002 | |
| WO | WO 03/088805 A2 | | 10/2003 | |
| WO | WO 2004/033016 A1 | | 4/2004 | |
| WO | WO 2006/081011 A2 | | 8/2006 | |

OTHER PUBLICATIONS

Aichinger, H.; Dierker, J.; Joite-Barfuβ, S.; Säbel, M. "Raw X-Ray Data for Unfiltered Photons," *Radiation Exposure and Image Quality in X-Ray Diagnostic Radiology: Physical Principles and Clinical Applications*, Springer, Berlin.

"Biological Evaluation of Medical Devices—Part 1: Evaluation and Testing," *American National Standard ANSI/AAMI/ISO 10993-1:2003*, Association for the Advancement of Medical Instrumentation (AAMI), Arlington, VA, USA, 2003, 25 pages.

Boriskina, N.G.; Kenina, E.M. "Phase Equilibria in the Ti-TiPd-TiNi System Alloys," *Titanium '80, Science and Technology, Proceedings of the 4th International Conference on Titanium*, Kumura, H. and Izumi O., eds., 1980, The Metallurgical Society of AIME, Warrendale, PA, pp. 2917-2927.

Bozzolo, G.; Noebe, R.D.; Mosca, H.O. "Atomistic Modeling of Pd Site Preference in NiTi," *Journal of Alloys and Compounds*, 2005, 386, pp. 125-138.

Cai, W.; Tanaka, S.; Otsuka, K. "Thermal Cyclic Characteristics Under Load in a $Ti_{50.6}Pd_{30}Ti_{19.4}$ Alloy," *Materials Science Forum*, 2000, 327-328, pp. 279-282.

Cai, W.; Zhao, L. "The Reverse Transformation of Deformation-Induced Martensite in a Ni-Ti-Nb Shape Memory Alloy with Wide Hysteresis," *Shape Memory Materials '94 Proceedings of the International Symposium on Shape Memory Materials*, 1994, International Academic Publishers, pp. 235-238 (5 pages).

Craig, C.; Friend, C.; Edwards, M.; Gokcen, N. "Tailoring Radiopacity of Austenitic Stainless Steel for Coronary Stents," *Proceedings from the Materials & Processes for Medical Devices Conference*, Sep. 8-10, 2003, ASM International, Anaheim, CA, 2004, pp. 294-297.

Di, J.; Wenxi, L.; Ming, H.; Defa, W.; Zhizhong, D. "Some Properties of NiTi-Nb-X Quarternary Alloys," *Z. Metallkd.*, 2000, 91(3), pp. 258-260.

Donkersloot, H.C.; Van Vucht, J.H.N. "Martensitic Transformations in Gold-Titanium, Palladium-Titanium and Platinum-Titanium Alloys Near the Equiatomic Composition," *Journal of the Less-Common Metals*, 1970, 20, pp. 83-91.

Eckelmeyer, K.H. "The Effect of Alloying on the Shape Memory Phenomenon in Nitinol," *Scripta Metallurgica*, 1976, 10, pp. 667-672.

Enami, K.; Hara, M.; Maeda, H. "Effect of W Addition on the Martensitic Transformation and Shape Memory Behaviour of the TiNi-Base Alloys," *Journal de Physique IV*, 1995, 5, pp. C8-629-C8-633.

Enami, K.; Yoshida, T.; Nenno, S. "Premartensitic and Martensitic Transformations in TiPd-Fe Alloys," *Proceedings of the International Conference on Martensitic Transformations*, The Japan Institute of Metals, 1986, pp. 103-108.

Golberg, D.; Xu, Y.; Murakami, Y.; Otsuka, K.; Ueki, T.; Horikawa, H. "High-Temperature Shape Memory Effect in $Ti_{50}Pd_{50-x}Ni_x$ (x=10, 15, 20) Alloys," *Materials Letters*, 1995, 22, pp. 241-248.

Gschneidner Jr., K.; Russell, A.; Pecharsky, A.; Morris, J.; Zhang, Z.; Lograsso, T.; Hsu, D.; Chester Lo, C.H.; Ye, Y.; Slager, A.; Kesse, D. "A Family of Ductile Intermetallic Compounds," *Nature Materials*, 2003, 2, pp. 587-590.

Gupta, K.P. "The Hf-Ni-Ti (Hafnium-Nickel-Titanium) System," *Journal of Phase Equilibria*, 2001, 22(1), pp. 69-72.

Hashi, K.; Ishikawa, K.; Matsuda, T.; Aoki, K. "Hydrogen Permeation Characteristics of Multi-Phase Ni-Ti-Nb Alloys," *Journal of Alloys and Compounds*, 2004, 368, pp. 215-220.

Hashi, K.; Ishikawa, K.; Matsuda, T.; Aoki, K. "Hydrogen Permeation of Ternary Ni-Ti-Nb Alloys," *Advanced Materials for Energy Conversion II*, 2004, TMS (The Minerals, Metals & Materials Society), Warrendale, PA, pp. 283-289.

Haxel, G.B.; Hedrick, J.B.; Orris, G.J. "Rare Earth Elements-Critical Resources for High Technology," USGS Fact Sheet 087-02, U.S. Dept. of the Interior, 2002, 4 pages.

Hodgson, D.E.; Brown, J.W. *Using Nitinol Alloys*, Shape Memory Applications, Inc., San Jose, CA, 2000, 52 pages.

Hosoda, H.; Tsuji, M.; Takahashi, Y.; Inamura, T.; Wakashima, K.; Yamabe-Mitarai, Y.; Miyazaki, S.; Inoue, K. "Phase Stability and Mechanical Properties of Ti-Ni Shape Memory Alloys containing Platinum Group Metals," *Materials Science Forum*, 2003, 426-432, pp. 2333-2338.

(56) References Cited

OTHER PUBLICATIONS

Huang, X.; Lei Y.; Huang, B.; Chen, S.; Hsu, T.Y. "Effect of Rare-Earth Addition on the Shape Memory Behavior of a FeMnSiCr Alloy," *Materials Letters*, 2003, 57, pp. 2787-2791.

Huisman-Kleinherenbrink, P.M.; Beyer, J. "The Influence of Ternary Additions on the Transformation Temperatures of NiTi Shape Memory Alloys—A Theoretical Approach," *Journal de Physique IV*, 1991, 1, pp. C4-47-C4-52.

Jung, J.; Ghosh, G.; Olson, G.B. "A Comparative Study of Preciptiation Behavior of Heusler Phase ($Ni_2TiAl$) from B2-TiNi in Ni-Ti-Al and Ni-Ti-Al-X (X = Hf, Pd, Pt, Zr) Alloys," *Acta Materialia*, 2003, 51, pp. 6341-6357.

Kattner, U.R. "Thermodynamic Modeling of Multicomponent Phase Equilibria," *Journal of Metals (JOM)*, 1997, 49(12), pp. 14-19.

Khachin, V.N.; Gjunter, V.E.; Sivokha, V.P.; Savvinov, A.S. "Lattice Instability, Martensitic Transformations, Plasticity and Anelasticity of TiNi," *Proc. ICOMAT*, 1979, 79, pp. 474-479.

Khachin, V.N.; Matveeva, N.M.; Sivokha, V.P.; Chernov, D.B.; Kovneristyi, Y.K. "High-Temperature Shape-Memory Effects in Alloys of the TiNi-TiPd System," Translated from Doklady Akademii Nauk SSSR, vol. 257, No. 1, pp. 167-169, Mar. 1981. Plenum Publishing Corporation, New York, NY, 1981, pp. 195-197.

Lindquist, P.G.; Wayman, C.M. "Shape Memory and Transformation Behavior of Martensitic Ti-Pd-Ni and Ti-Pt-Ni Alloys," *Engineering Aspects of Shape Memory Alloys*, Butterworth-Heinemann, Ltd., London, UK, 1990, pp. 58-68.

Lindquist, P.G. "Structure and Transformation Behavior of Martensitic Ti—(Ni, Pd) and Ti—(Ni, Pt) Alloys," University Microfilms International, Ann Arbor, MI, 1988, Order No. 8908756, 134 pages.

Liu, A.L.; Gao, Z.Y.; Gao, L.; Cai, W.; Wu, Y. "Effect of Dy Addition on the Microstructure and Martensitic Transformation of a Ni-rich TiNi Shape Memory Alloy," *Journal of Alloys and Compounds*, 2007, 437, pp. 339-343.

Liu, A.; Meng, X.; Cai, W.; Zhao, L. "Effect of Ce Addition on Martensitic Transformation Behavior of TiNi Shape Memory Alloys," *Materials Science Forum*, 2005, 475-479, pp. 1973-1976, 6 pages.

Liu, J.; Ma, J.; Wang, Z.; Wu, G. "Effects of Aging Treatment on Shape Memory Characteristics of Ni-Ti-Ta Alloy," *Rare Metal Materials and Engineering*, 2003, 32(10), pp. 777-781 (6 pages).

Liu, J.; Pan, S.; Zhuang, Y. "Isothermal Section of the Phase Diagram of the Ternary System Dy-Ni-Ti at 773 K, "*Journal of Alloys and Compounds*, 2000, 313, pp. 93-94.

Liu, M.; Tu, M.J.; Zhang, X.M.; Li, Y.Y.; Shelyakov, A.V. "Microstructure of Melt-Spinning High Temperature Shape Memory Ni-Ti-Hf Alloys," *Journal of Materials Science Letters*, 2001, 20, pp. 827-830.

Ma, J.; Liu, J.; Wang, Z.; Xue, F.; Wu, K-H.; Pu, Z. "Effects of Ta Addition on NiTi Shape Memory Alloys," *J. Mater. Sci. Technol.*, 2000, 16(5), pp. 534-536.

Ma, J.; Yang, F.; Subirana, J.I.; Pu, Z.J.; Wu; K.H. "Study of NiTi-Ta Shape Memory Alloys," *SPIE Conference on Smart Materials Technologies*, 1998, 3324, pp. 50-57.

Meisner, L.L.; Sivokha, V.P. "The Effect of Applied Stress on the Shape Memory Behavior of TiNi-Based Alloys with Different Consequences of Martensitic Transformations," *Physica B*, 2004, 344, pp. 93-98.

Noebe, R.; Biles, T.; Padula, S.A. "NiTi-Based High-Temperature Shape-Memory Alloys: Properties, Prospects, and Potential Applications," *Materials Engineering*, 2006, 32, pp. 145-186, Marcel Dekker, Inc., New York, USA, 75 pages.

Noebe, R.; Gaydosh, D.; Padula, S.; Garg, A.; Biles, T.; Nathal, M. "Properties and Potential of Two (Ni,Pt)Ti Alloys for Use as High-Temperature Actuator Materials," *12th SPIE Conf. International Symposium*, San Diego, CA, USA, Mar. 6-10, 2005, pp. 1-12.

Otsuka, K.; Oda, K.; Ueno, Y.; Piao, M.; Ueki, T.; Horikawa, H. "The Shape Memory Effect in a $Ti_{50}Pd_{50}$ Alloy," *Scripta Metallurgica et Materialia*, 1993, 29, pp. 1355-1358.

Oyamada, O.; Amano, K.; Enomoto, K., Shigenaka, N.; Matsumoto, J.; Asada, Y. "Effect of Environment on Static Tensile and Fatigue Properties of Ni-Ti-Nb Shape Memory Alloy," *JSME International Journal*, 1999, Series A, 42, pp. 243-248.

Pryakhina, L.I.; Myasnikova, K.P.; Burnashova, V.V.; Cherkashin, E.E.; Markiv, V.Y. "Ternary Intermetallic Compounds in the System Ni-Ti-Nb," A. A. Baikov Institute of Metallurgy; (Translated from *Poroshkovaya Metallurgiya*, 1966, 8(44), pp. 61-69) pp. 643-650.

Qiang, D.S.; Ying, Q.G.; Bo, Y.H.; Ming, T.S. "Phase Transformation and Memory Effect of the High Temperature Shape Memory Alloy $Ti_{49}Ni_{25}Pd_{26}B_{0.12}$," *Shape Memory Materials '94 Proceedings of the International Symposium on Shape Memory Material*, 1994, International Academic Publishers, Beijing, China, pp. 248-252 (6 pages).

"Radiopaque Polymers," *Encyclopedia of Polymer Science and Engineering*, John Wiley & Sons, Inc., New York, USA, 1988, 14, pp. 1-8 (10 pages).

Rios, O.; Noebe, R.; Biles, T.; Garg, A.; Palczer, A.; Scheiman, D.; Seifert, H.J.; Kaufman, M. "Characterization of Ternary NiTiPt High-Temperature Shape Memory Alloys," *12th SPIE Conf. International Symposium*, San Diego, CA, USA, Mar. 6-10, 2005, pp. 1-12.

Russell, S.M.; Hodgson, D.E.; Basin, F. "Improved NiTi Alloys for Medical Applications," *SMST-97: Proceedings of the Second International Conference on Shape Memory and Superelastic Technologies*, Pacific Grove, CA, 1997, pp. 429-436.

Shimizu, S.; Xu, Y.; Okunishi, E.; Tanaka, S.; Otsuka, K.; Mitose, K. "Improvement of Shape Memory Characteristics by Precipitation-Hardening of Ti-Pd-Ni Alloys," *Materials Letters*, 1998, 34, pp. 23-29.

"Standard Practice for Selecting Generic Biological Test Methods for Materials and Devices," *American Society for Testing and Materials (ASTM) Standard F748-04*, ASTM International, West Conshohocken, PA, 2004, 1 page.

"Standard Practice for Direct Contact Cell Culture Evaluation of Materials for Medical Devices," *American Society for Testing and Materials (ASTM) Standard F813-01*, ASTM International, West Conshohocken, PA, 2001, 4 pages.

"Standard Specification for Wrought Nickel-Titanium Shape Memory Alloys for Medical Devices and Surgical Implants," *American Society for Testing and Materials (ASTM) Standard F2063-05*, ASTM International, West Conshohocken, PA, 2005, 4 pages.

"Standard Test Method for Agar Diffusion Cell Culture Screening for Cytotoxicity," *American Society for Testing and Materials (ASTM) Standard F895-84*, ASTM International, West Conshohocken, PA, 2006, 5 pages.

"Standard Test Method for Tension Testing of Nickel-Titanium Superelastic Materials," *American Society for Testing and Materials (ASTM) Standard F2516-07*, ASTM International, West Conshohocken, PA, 2007, 6 pages.

"Standard Test Method for Transformation Temperature of Nickel-Titanium Alloys by Thermal Analysis," *American Society for Testing and Materials (ASTM) Standard F2004-05*, ASTM International, West Conshohocken, PA, 2005, 4 pages.

Sun, L.; Wu, K-H. "The Two-Way Memory Effect (TWME) in NiTi-Pd High Temperature Shape Memory Alloys," *SPIE Conference Proceedings: Smart Structures and Materials*, 1994, 2189, pp. 298-305.

Suzuki, Y.; Xu, Y.; Morito, S.; Otsuka, K.; Mitose, K. "Effects of Boron Addition on Microstructure and Mechanical Properties of Ti-Pd-Ni High-Temperature Shape Memory Alloys," *Materials Letters*, 1998, 36, pp. 85-94.

Thoma, P.E.; Boehm, J.J. "The Effect of Hafnium and Thermal Cycling on the Transformation Temperatures of NiTi-Based Shape Memory Alloys," *Mat. Res. Soc. Symp. Proc.*, 2000, 604, pp. 221-226.

*Using Nitinol Alloys*, Johnson Matthey, San Jose, CA, 2004, 1-46.

Wong, T.; Seuntjens, J.M.; "Development of Rare Earth Regenerator Materials in Fine Wire Form," *Adv. Cryog. Eng.*, 1997, 42, pp. 439-444, 2 page Abstract.

Wu, K.H.; Liu, Y.Q.; Maich, M.; Tseng, H.K. "The Mechanical Properties of a NiTi-Pd High Temperature Shape Memory Alloy," *SPIE Conference Proceedings: Smart Structures and Materials*, 1994, 2189, pp. 306-313.

(56) References Cited

OTHER PUBLICATIONS

Wu, S.K.; Wayman, C.M. "Martensitic Transformations and the Shape Memory Effect in $Ti_{50}Ni_{10}Au_{40}$ and $Ti_{50}Au_{50}$ Alloys," *Metallography*, 1987, 20, pp. 359-376.

Xu, Y.; Otsuka, K.; Furubayashi, E.; Mitose, K. "TEM Observation of Recrystallization Process in Solution-Treated $Ti_{50}Pd_{50}$ Martensite," *Materials Letters*, 1998, 34, pp. 14-18.

Xu, Y.; Shimizu, S.; Suzuki, Y.; Otsuka, K.; Ueki, T.; Mitose, K. "Recovery and Recrystallization Processes in Ti-Pd-Ni High-Temperature Shape Memory Alloys," *Acta Mater.*, 1997, 45(4), pp. 1503-1511.

Yang, W.S.; Mikkola, D.E. "Ductilization of Ti-Ni-Pd Shape Memory Alloys with Boron Additions," *Scripta Metallurgica et Materialia*, 1993, 28, pp. 161-165.

Zadno, G.R.; Duerig, T.W. "Linear Superelasticity in Cold-Worked Ni-Ti," *Engineering Aspects of Shame Memory Alloys*, Butterworth-Heinemann, Ltd., 1990, pp. 414-419.

Zhang, C.; Thoma, P.; Chin, B.; Zee, R. "Martensitic and R-Phase Transformations in Ni-Ti and Ni-Ti-Hf," *Trans. Nonferrous Met. Soc. China*, 1999, 9(1), pp. 55-64.

Zhao, C. "Improvement of Shape Memory Effect in Fe-Mn-Si-Cr-Ni Alloys," *Metallurgical and Materials Transactions A*, 1999, 30A, pp. 2599-2604.

Zhu, Y.R.; Pu, Z.J.; Li, C.; Wu, K.H. "The Stability of NiTi-Pd and NiTi-Hf High Temperature Shape Memory Alloys," *Shape Memory Materials '94 Proceedings of the International Symposium on Shape Memory Materials*, 1994, International Academic Publishers, pp. 253-257 (6 pages).

International Preliminary Report on Patentability for International Patent Application No. PCT/US2007/019445 dated Dec. 4, 2008.

Seo, C-Y.; Choi, S-J.; Choi, J.; Park, C-N.; Lee, P.S.; Lee, J-Y. "Effect of Ti and Zr Additions on the Characteristics of $AB_5$-type Hydride Electrode for Ni-MH Secondary Battery," *International Journal of Hydrogen Energy*, 2003, 28, 317-327.

US 5,976,281, 11/1999, Nakamura et al. (withdrawn)

\* cited by examiner

NICKEL-TITANIUM ALLOY INCLUDING A RARE EARTH ELEMENT

RELATED APPLICATIONS

The present patent document claims the benefit of the filing date under 35 U.S.C. §119(e) of Provisional U.S. Patent Application Ser. No. 60/842,484, filed Sep. 6, 2006, Provisional U.S. Patent Application Ser. No. 60/872,369, filed Nov. 29, 2006, and Provisional U.S. Patent Application Ser. No. 60/872,370, filed Nov. 29, 2006, which are hereby incorporated by reference.

TECHNICAL FIELD

The present disclosure relates generally to nickel-titanium alloys and more particularly, but not exclusively, to nickel-titanium alloys for medical device applications.

BACKGROUND

Nickel-titanium alloys are commonly used for the manufacture of intraluminal biomedical devices, such as self-expandable stents, stent grafts, embolic protection filters, and stone extraction baskets. Such devices may exploit the superelastic or shape memory behavior of equiatomic or near-equiatomic nickel-titanium alloys, which are commonly referred to as Nitinol.

As a result of the poor radiopacity of nickel-titanium alloys, however, such devices may be difficult to visualize from outside the body using non-invasive imaging techniques, such as x-ray fluoroscopy. Visualization is particularly problematic when the intraluminal device is made of fine wires or thin-walled struts. Consequently, a clinician may not be able to accurately place and/or manipulate a Nitinol stent or basket within a body vessel.

Current approaches to improving the radiopacity of nickel-titanium medical devices include the use of radiopaque markers or coatings. For example, gold markers attached to ends of a stent may guide the positioning of the device and delineate its length during an x-ray procedure. Alternatively, a medical device may be plated, clad or otherwise coated with gold or another heavy metal to create a radiopaque surface or outer layer. In another approach, a heavy metal cylinder may be included within the lumen of a stent to produce a radiopaque core. These approaches to improving radiopacity may have shortcomings, however. In some cases, markers may be easily dislodged or may undesirably increase the delivery profile of the device. A surface coating or cladding may delaminate as the medical device is expanded or it may interfere with the mechanical behavior of the device. Radiopaque cores may be expensive to fabricate. Galvanic corrosion may also be a problem. Furthermore, gold and other heavy metals, such as platinum, palladium, and tungsten, tend to be costly.

BRIEF SUMMARY

Disclosed herein is a nickel-titanium alloy comprising nickel, titanium, and at least one rare earth element. The nickel-titanium alloy may further include one or more additional alloying elements. In addition to radiopacity, the nickel-titanium alloy preferably exhibits superelastic or shape memory behavior. Medical devices comprising the nickel-titanium alloy and a method of making and using them are also disclosed.

According to one embodiment, the nickel-titanium alloy comprises from about 34 at. % (atomic percent) to about 60 at. % nickel, from about 34 at. % to about 60 at. % titanium, and from about 0.1 at. % to about 15 at. % at least one rare earth element selected from the group consisting of La, Pr, Nd, Pm, Sm, Eu, Gd, Tb, Dy, Ho, Er, Tm, Yb, Lu, Ac, Th, Pa, and U.

According to another embodiment, the nickel-titanium alloy comprises from about 34 at. % to about 60 at. % nickel, from about 34 at. % to about 60 at. % titanium, and from about 0.1 at. % to about 15 at. % at least one rare earth element, whereby the nickel-titanium alloy has a radiopacity greater than that of a near-equiatomic binary nickel-titanium alloy.

According to another embodiment, the nickel-titanium alloy includes from about 34 at. % to about 60 at. % nickel, from about 34 at. % to about 60 at. % titanium, from about 0.1 at. % to about 10 at. % at least one rare earth element, and at least one transition metal at a concentration of no more than about 4.9 at. %. The rare earth element is selected from the group consisting of Ce, La, Pr, Nd, Pm, Sm, Eu, Gd, Tb, Dy, Ho, Er, Tm, Yb, Lu, Ac, Th, Pa, and U.

According to another embodiment, the nickel-titanium alloy comprises from about 34 at. % to about 60 at. % nickel, from about 34 at. % to about 60 at. % titanium, from about 0.1 at. % to about 10 at. % at least one rare earth element; and at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U, and whereby the nickel-titanium alloy has a radiopacity greater than that of a near-equiatomic binary nickel-titanium alloy.

According to one embodiment, the medical device comprises at least one component including a nickel-titanium alloy including from about 34 at. % to about 60 at. % nickel, from about 34 at. % to about 60 at. % titanium, and from about 0.1 at. % to about 15 at. % at least one rare earth element, wherein the at least one rare earth element is selected from the group consisting of La, Pr, Nd, Pm, Sm, Eu, Gd, Tb, Dy, Ho, Er, Tm, Yb, Lu, Ac, Th, Pa and U.

According to another embodiment, the medical device comprises at least one component comprising a nickel-titanium alloy including from about 34 at. % to about 60 at. % nickel; from about 34 at. % to about 60 at. % titanium; from about 0.1 at. % to about 10 at. % at least one rare earth element; and at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U.

According to another embodiment, the medical device comprises least one component comprising a nickel-titanium alloy including nickel at a concentration of from about 34 at. % to about 60 at. %, titanium at a concentration of from about 34 at. % to about 60 at. %, and at least one rare earth element at a concentration of from about 0.1 at. % to about 15 at. %, wherein the at least one rare earth element is selected from the group consisting of La, Pr, Nd, Pm, Sm, Eu, Gd, Tb, Dy, Ho, Er, Tm, Yb, Lu, Ac, Th, Pa and U. The nickel-titanium alloy comprises a radiopacity greater than that of a near-equiatomic binary nickel-titanium alloy, and the nickel-titanium alloy further comprises a recoverable strain of at least about 0.5% upon removal of a deforming stress at or below body temperature.

Also disclosed herein is a method of using a medical device. To carry out the method, according to one aspect, a medical device including at least one component comprising from about 34 at. % to about 60 at. % nickel, from about 34 at. % to about 60 at. % titanium, and from about 0.1 at. % to about 15 at. % at least one rare earth element is provided. The rare earth element is selected from the group consisting of La, Pr, Nd, Pm, Sm, Eu, Gd, Tb, Dy, Ho, Er, Tm, Yb, Lu, Ac, Th, Pa, and U. The medical device is then delivered to a treatment site within the patient.

According to another embodiment, the method of using the medical device comprises providing a medical device comprising at least one component comprising a nickel-titanium alloy including from about 34 at. % to about 60 at. % nickel, from about 34 at. % to about 60 at. % titanium, from about 0.1 at. % to about 10 at. % at least one rare earth element, and at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U, and delivering the medical device to a treatment site within the patient.

Also disclosed is a method of imaging a medical device within a patient. The method comprises, according to one aspect, delivering a medical device having at least one component made from a nickel-titanium alloy including from about 34 at. % to about 60 at. % nickel, from about 34 at. % to about 60 at. % titanium, and from about 0.1 at. % to about 15 at. % at least one rare earth element to a site in a patient. The at least one rare earth element is selected from the group consisting of La, Pr, Nd, Pm, Sm, Eu, Gd, Tb, Dy, Ho, Er, Tm, Yb, Lu, Ac, Th, Pa, and U. The patient is then exposed to radiation having an energy in the range of from 15 keV to 150 keV to image the medical device.

According to another aspect, the method of imaging the medical device within a patient comprises delivering a medical device having at least one component comprising a nickel-titanium alloy including from about 34 at. % to about 60 at. % nickel, from about 34 at. % to about 60 at. % titanium, from about 0.1 at. % to about 10 at. % at least one rare earth element, and at least one transition metal at a concentration of no more than about 4.9 at. % to a site in a patient. The at least one rare earth element is selected from the group consisting of Ce, La, Pr, Nd, Pm, Sm, Eu, Gd, Tb, Dy, Ho, Er, Tm, Yb, Lu, Ac, Th, Pa, and U. The patient is then exposed to radiation having an energy in the range of from 15 keV to 150 keV to image the medical device.

In addition, a method of making a medical device is disclosed. To carry out the method, a melt including from about 34 at. % to about 60 at. % nickel, from about 34 at. % to about 60 at. % titanium, and from about 0.1 at. % to about 15 at. % a rare earth element is formed. The rare earth element is selected from the group consisting of La, Pr, Nd, Pm, Sm, Eu, Gd, Tb, Dy, Ho, Er, Tm, Yb, Lu, Ac, Th, Pa, and U. The melt is cooled to form a solid, and the solid is formed into a component to form a medical device.

According to another aspect, the method of making the medical device comprises forming a melt comprising from about 34 at. % to about 60 at. % nickel, from about 34 at. % to about 60 at. % titanium, from about 0.1 at. % to about 10 at. % at least one rare earth element, and at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U. The melt is cooled to form a solid, and the solid is formed into a component to form the medical device.

BRIEF DESCRIPTION OF THE DRAWINGS

Preferred features of the present invention will now be described, by way of example, with reference to the accompanying drawings, in which.

DETAILED DESCRIPTION

Definitions

Figure 1:
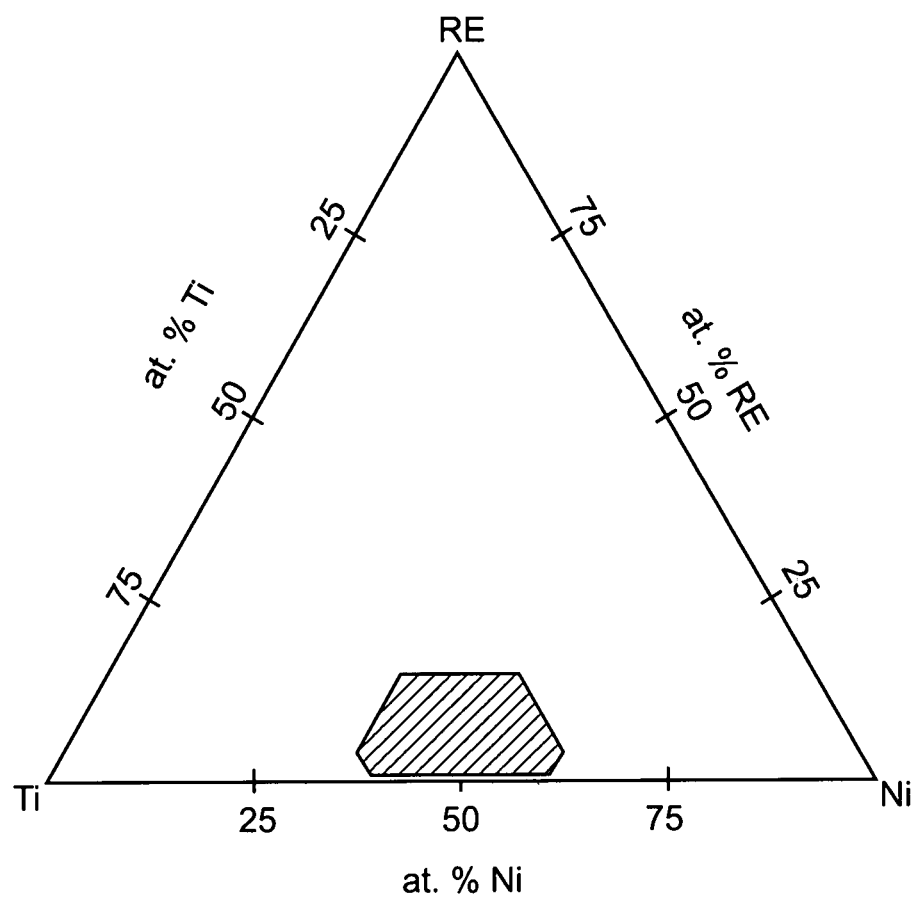
FIG. 1 is a ternary alloy concentration diagram showing a composition range of a nickel-titanium alloy according to one embodiment.

As used in the following specification and the appended claims, the following terms will have the meanings ascribed below:

Martensite start temperature ($M_s$) is the temperature at which a phase transformation to martensite begins upon cooling for a shape memory material exhibiting a martensitic phase transformation.

Martensite finish temperature ($M_f$) is the temperature at which the phase transformation to martensite concludes upon cooling.

Austenite start temperature ($A_s$) is the temperature at which a phase transformation to austenite begins upon heating for a shape memory material exhibiting an austenitic phase transformation.

Austenite finish temperature ($A_f$) is the temperature at which the phase transformation to austenite concludes upon heating.

R'-phase start temperature ($R'_s$) is the temperature at which a phase transformation to R-phase begins upon heating for shape memory material exhibiting an R-phase transformation.

R'-phase finish temperature ($R'_f$) is the temperature at which the phase transformation to R-phase concludes upon heating.

R-phase start temperature ($R_s$) is the temperature at which a phase transformation to R-phase begins upon cooling for a shape memory material exhibiting an R-phase transformation.

R-phase finish temperature ($R_f$) is the temperature at which the phase transformation to R-phase concludes upon cooling.

Radiopacity is a measure of the capacity of a material or object to absorb incident electromagnetic radiation, such as x-ray radiation. A radiopaque material preferentially absorbs incident x-rays and tends to show high radiation contrast and good visibility in x-ray images. A material that is not radiopaque tends to transmit incident x-rays and may not be readily visible in x-ray images. A linear absorption coefficient ($\mu$) of a material may be a good indicator of its capacity for absorbing x-ray radiation, and thus its radiopacity. For the purposes of this disclosure, a cumulative linear absorption coefficient, which is defined and described in detail below, may be taken as representative of the radiopacity of a material.

The term "near-equiatomic binary nickel-titanium alloy" refers to a two-component alloy including from 45 at. % to 55 at. % nickel and the balance titanium.

Described herein is a nickel-titanium alloy comprising nickel, titanium, and at least one rare earth element. According to one embodiment, the nickel-titanium alloy comprises at least one additional alloying element. The nickel-titanium alloy preferably has improved radiopacity compared to previous nickel-titanium alloys. Accordingly, a medical device comprising the nickel-titanium alloy may have better visibility during non-invasive imaging procedures such as x-ray fluoroscopy. The nickel-titanium alloy preferably has superelastic or shape memory properties that are advantageous for medical devices, as will be discussed below.

Preferably, the one or more rare earth elements of the nickel-titanium alloy are chosen from the lanthanide series and/or the actinide series of the periodic table, which include La, Ce, Pr, Nd, Pm, Sm, Eu, Gd, Tb, Dy, Ho, Er, Tm, Yb, Lu, Ac, Th, Pa, and U. Yttrium (Y) and scandium (Sc) are sometimes referred to as rare earth elements although they are not elements of the lanthanide or actinide series. More preferably, the rare earth (RE) element is selected from the group consisting of La, Pr, Nd, Pm, Sm, Eu, Gd, Tb, Dy, Ho, Er, Tm, Yb, and Lu.

According to a preferred embodiment, the rare earth element occupies a ternary position in terms of concentration in the alloy. In other words, the amount of the rare earth element is preferably less than the respective amounts of nickel and titanium, but greater than the amount of any additional alloying elements that may be present in the alloy. An exemplary composition range for the alloy is shown schematically in FIG. 1.

The nickel-titanium alloy comprises at least about 0.1% at least one rare earth element, according to one embodiment. Preferably, the nickel-titanium alloy comprises at least about 1.0 at. % at least one rare earth element. More preferably, the nickel-titanium alloy comprises at least about 2.5 at. % at least one rare earth element. It may be desirable that the nickel-titanium alloy comprises at least about 5 at. % at least one rare earth element.

It is also preferred that the nickel-titanium alloy comprises no more than about 15 at. % at least one rare earth element. More preferably, the nickel-titanium alloy comprises no more than about 12.5 at. % at least one rare earth element. Even more preferably, the nickel-titanium alloy comprises no more than about 10 at. % at least one rare earth element. Yet even more preferably, the nickel-titanium alloy comprises no more than about 7.5 at. % at least one rare earth element. Most preferably, the nickel-titanium alloy comprises no more than about 5.0 at. % at least one rare earth element.

By way of example, the nickel-titanium alloy comprises from about 0.1 at. % to about 15 at. % at least one rare earth element, according to a preferred embodiment. Preferably, the nickel-titanium alloy comprises from about 1.0 at. % to about 12.5 at. %. More preferably, the nickel-titanium alloy comprises from about 1.0 at. % to about 10.0 at. % at least one rare earth element. Even more preferably, the nickel-titanium alloy comprises from about 1.0 at. % to about 7.5 at. %, or from about 2.5 at. % to about 7.5 at. % at least one rare earth element. Most preferably, the nickel-titanium alloy comprises from about 2.5 at. % to about 5.0 at. % at least one rare earth element. For example, the nickel-titanium alloy may comprise 3.0 at. %, 3.25 at. %, 3.5 at. %, 3.75 at. % or 4 at. % at least one rare earth element.

According to a preferred embodiment, the nickel-titanium alloy comprises at least about 34 at. % nickel. More preferably, the nickel-titanium alloy comprises at least about 36.5 at. % nickel. Even more preferably, the nickel-titanium alloy comprises at least about 39 at. % nickel. Still more preferably, the nickel-titanium alloy comprises at least about 44 at. % nickel.

It is also preferred that the nickel-titanium alloy comprises no more than about 60 at. % nickel. More preferably, the nickel-titanium alloy comprises no more than about 55 at. % nickel. The nickel-titanium alloy may comprise 50 at. % nickel.

According to a preferred embodiment, the nickel-titanium alloy comprises at least about 34 at. % titanium. More preferably, the nickel-titanium alloy comprises at least about 36.5 at. % titanium. Even more preferably, the nickel-titanium alloy comprises at least about 39 at. % titanium. Still more preferably, the nickel-titanium alloy comprises at least about 44 at. % titanium.

It is also preferred that the nickel-titanium alloy comprises no more than about 60 at. % titanium. More preferably, the nickel-titanium alloy comprises no more than about 55 at. % titanium. Even more preferably, the nickel-titanium alloy comprises no more than about 50 at. % titanium.

According to an exemplary embodiment, the nickel-titanium alloy comprises from about 36.5 at. % to about 55 at. % nickel, from about 36.5 at. % to about 55 at. % titanium, and from about 2.5 at. % to about 12.5 at. % at least one rare earth element. According to another exemplary embodiment, the nickel-titanium alloy comprises from about 39 at. % to about 55 at. % nickel, from about 39 at. % to about 55 at. % titanium, and from about 5 at. % to about 10 at. % at least one rare earth element.

The nickel-titanium alloy may also contain one or more additional alloying elements, such as transition metals or other metals. For example, one or more of Al, Cr, Mn, Fe, Co, Cu, Zn, Ga, Ge, Zr, Nb, Mo, Tc, Ru, Rh, Pd, Ag, Cd, In, Sn, Sb, Hf, Ta, W, Re, Os, Ir, Pt, Au, Hg, Tl, Pb, Bi, Po, V, and Mischmetal may be included as the additional alloying element (AAE). It is preferable that the nickel-titanium alloy comprises no more than about 14.9 at. % AAE. More preferably, the nickel-titanium alloy comprises no more than about 9.9 at. % ME. Even more preferably, the nickel-titanium alloy comprises no more than about 7.4 at. % AAE. Still more preferably, the nickel-titanium alloy comprises no more than about 4.9 at. % AAE. Most preferably, the nickel-titanium alloy comprises no more than about 1.9 at. % AAE. According to one preferred embodiment, the nickel-titanium alloy includes at least about 0.1 at. % AAE. Preferably, the additional alloying element has a lower concentration in the nickel-titanium alloy than the rare earth element when the one or more additional alloying elements are selected from the group consisting of Ir, Pt, Au, Re, W, Pd, Rh, Ta, Ag, Ru, Hf, Os, Zr, Nb, and Mo.

It is known in the art that equiatomic or near-equiatomic binary nickel-titanium alloys exhibit superelastic or shape memory behavior. Such alloys are commonly referred to as Nitinol or Nitinol alloys. Slightly nickel-rich Nitinol alloys including, for example, 51 at. % Ni and 49 at. % Ti, are known to be useful for medical devices which are austenitic at body temperature. Specifically, alloys including 50.6-50.8 at. % Ni and 49.2-49.4 at. % Ti are considered to be medical grade Nitinol alloys.

Accordingly, the nickel-titanium alloy of the present disclosure comprises about 51 at. % Ni, about 34 at. % Ti, and about 15 at. % RE, according to one preferred embodiment. In another example in which one or more additional alloying elements (AAE) are present in the alloy, the nickel-titanium alloy preferably includes about 51 at. % Ni, about 34 at. % Ti, about (15-x) at. % RE, and about x at. % AAE, where $0 \leq x \leq 14.9$. Preferably, the rare earth element is in the ternary position in the alloy and $0 \leq x \leq 7.4$. According to these examples, the rare earth element substitutes for titanium. Alternatively, the rare earth element may substitute for nickel, or may substitute for both nickel and titanium.

According to another preferred embodiment, the nickel-titanium alloy of the present disclosure comprises about 51 at. % Ni, about 36.5 at. % Ti, and about 12.5 at. % RE. In another example in which one or more additional alloying elements (AAE) are present in the alloy, the nickel-titanium alloy preferably includes about 51 at. % Ni, about 36.5 at. % ti, about (12.5-x) at. % RE, and about x at. % AAE, where $0 \leq x \leq 12.4$. Preferably, the rare earth element is in the ternary position in the alloy and $0 \leq x \leq 6.2$. According to these examples, the rare earth element substitutes for titanium. Alternatively, the rare earth element may substitute for nickel, or may substitute for both nickel and titanium.

According to another preferred embodiment, the nickel-titanium alloy of the present disclosure comprises about 51 at. % Ni, about 39 at. % Ti, and about 10 at. % RE. In another example in which one or more additional alloying elements (AAE) are present in the alloy, the nickel-titanium alloy preferably includes about 51 at. % Ni, about 39 at. % Ti, about (10-x) at. % RE, and about x at. % AAE, where $0 \leq x \leq 9.9$. Preferably, the rare earth element is in the ternary position in the alloy and $0 \leq x \leq 4.9$. According to these examples, the rare earth element substitutes for titanium. Alternatively, the rare earth element may substitute for nickel, or may substitute for both nickel and titanium.

According to another preferred embodiment, the nickel-titanium alloy comprises about 51 at. % Ni, about 41.5 at. % Ti, and about 7.5 at. % RE. In another example in which one or more additional alloying elements are present in the alloy, the nickel-titanium alloy preferably includes about 51 at. % Ni, about 41.5 at. % Ti, about (7.5-x) at. % RE, and about x at. % AAE, where $0 \leq x \leq 7.4$. Preferably, the rare earth element is in the ternary position in the alloy and $0 \leq x \leq 3.7$. According to these examples, the rare earth element substitutes for titanium. Alternatively, the rare earth element may substitute for nickel, or may substitute for both nickel and titanium.

According to another preferred embodiment, the nickel-titanium alloy comprises about 51 at. % Ni, about 44 at. % Ti, and about 5.0 at. % RE. In another example in which one or more additional alloying elements are present in the alloy, the nickel-titanium alloy includes about 51 at. % Ni, about 44 at. % Ti, about (5.0-x) at. % RE, and about x at. % AAE, where $0 \leq x \leq 4.9$. Preferably, the rare earth element is in the ternary position in the alloy and $0 \leq x \leq 2.4$. According to these examples, the rare earth element substitutes for titanium. Alternatively, the rare earth element may substitute for nickel, or may substitute for both nickel and titanium.

According to another preferred embodiment, the nickel-titanium alloy comprises about 51 at. % Ni, about 46.5 at. % Ti, and about 2.5 at. % RE. In another example in which one or more additional alloying elements are present in the alloy, the nickel-titanium alloy includes about 51 at. % Ni, about 46.5 at. % Ti, about (2.5-x) at. % RE, and about x at. % AAE, where $0 \leq x \leq 2.4$. Preferably, the rare earth element is in the ternary position in the alloy and $0 \leq x \leq 1.2$. According to these examples, the rare earth element substitutes for titanium. Alternatively, the rare earth element may substitute for nickel, or may substitute for both nickel and titanium.

In an alternative embodiment, the nickel-titanium alloy may include about 50 at. % Ni, (50-y-x) at. % Ti, y at. % RE, and x at. % AAE, where x is no more than about 15 and y is no more than about 14.9, as described previously. In another example, the nickel-titanium alloy may include about 52 at. % Ni, (48-y-x) at. % Ti, y at. % RE, and x at. % AAE, with x and y having the bounds described above. Alternatively, the alloy may include about 53 at. % Ni, (47-y-x) at. % Ti, y at. % RE, and x at. % AAE. It is also envisioned that the alloy may include about 54 at. % Ni, (46-y-x) at. % Ti, y at. % RE, and x at. % AAE, or 55 at. % Ni, (45-y-x) at. % Ti, y at. % RE, and x at. % AAE. In another example, the alloy may include about or 56 at. % Ni, (44-y-x) at. % Ti, y at. % RE, and x at. % AAE. According to one preferred embodiment, y is equal to (4-x), and x has the exemplary values shown in Table 1 below.

The nickel-titanium alloy has a phase structure that depends on the composition and processing history of the alloy. The rare earth element may form a solid solution with nickel and/or titanium. The rare earth element may also form one or more binary intermetallic compound phases with nickel and/or with titanium. In other words, the rare earth element may combine with nickel in specific proportions and/or with titanium in specific proportions. Without wishing to be bound by theory, it is believed that most of the rare earth

TABLE 1

Preferred Alloy Compositions (at. %)

| | | | | |
|---|---|---|---|---|
| $Ni_{50}Ti_{46}RE_4$ | $Ni_{50}Ti_{46}RE_{3.75}AAE_{0.25}$ | $Ni_{50}Ti_{46}RE_{3.5}AAE_{0.5}$ | $Ni_{50}Ti_{46}RE_{3.25}AAE_{0.75}$ | $Ni_{50}Ti_{46}RE_3AAE_1$ |
| $Ni_{51}Ti_{45}RE_4$ | $Ni_{51}Ti_{45}RE_{3.75}AAE_{0.25}$ | $Ni_{51}Ti_{45}RE_{3.5}AAE_{0.5}$ | $Ni_{51}Ti_{45}RE_{3.25}AAE_{0.75}$ | $Ni_{51}Ti_{45}RE_3AAE_1$ |
| $Ni_{52}Ti_{44}RE_4$ | $Ni_{52}Ti_{44}RE_{3.75}AAE_{0.25}$ | $Ni_{52}Ti_{44}RE_{3.5}AAE_{0.5}$ | $Ni_{52}Ti_{44}RE_{3.25}AAE_{0.75}$ | $Ni_{52}Ti_{44}RE_3AAE_1$ |
| $Ni_{53}Ti_{43}RE_4$ | $Ni_{53}Ti_{43}RE_{3.75}AAE_{0.25}$ | $Ni_{53}Ti_{43}RE_{3.5}AAE_{0.5}$ | $Ni_{53}Ti_{43}RE_{3.25}AAE_{0.75}$ | $Ni_{53}Ti_{43}RE_3AAE_1$ |
| $Ni_{54}Ti_{42}RE_4$ | $Ni_{54}Ti_{42}RE_{3.75}AAE_{0.25}$ | $Ni_{54}Ti_{42}RE_{3.5}AAE_{0.5}$ | $Ni_{54}Ti_{42}RE_{3.25}AAE_{0.75}$ | $Ni_{54}Ti_{42}RE_3AAE_1$ |
| $Ni_{55}Ti_{41}RE_4$ | $Ni_{55}Ti_{41}RE_{3.75}AAE_{0.25}$ | $Ni_{55}Ti_{41}RE_{3.5}AAE_{0.5}$ | $Ni_{55}Ti_{41}RE_{3.25}AAE_{0.75}$ | $Ni_{55}Ti_{41}RE_3AAE_1$ |
| $Ni_{56}Ti_{40}RE_4$ | $Ni_{56}Ti_{40}RE_{3.75}AAE_{0.25}$ | $Ni_{56}Ti_{40}RE_{3.5}AAE_{0.5}$ | $Ni_{56}Ti_{40}RE_{3.25}AAE_{0.75}$ | $Ni_{56}Ti_{40}RE_3AAE_1$ |

Erbium (Er) is a preferred rare earth element. It is believed that Er is less likely to cause cracking or brittleness of the nickel-titanium alloy at increasing rare earth concentrations than other rare earth elements. Chromium (Cr) is a preferred additional alloying element (AAE). It is believed that increasing concentrations of chromium are effective for suppressing the austenitic phase transformation temperatures of the alloy to near body temperature, as further discussed below. Nickel-rich alloys are also known to have suppressed transformation temperatures. Accordingly, compiled in Table 2 below are several preferred Ni—Ti alloy compositions that include Er and Cr, along with increasing concentrations of nickel.

elements set forth as preferred ternary alloying additions will substitute for titanium and form one or more intermetallic compound phases with nickel, such as, for example, NiRE, $Ni_2RE$, $Ni_3RE_2$ or $Ni_3RE_7$. In some cases, however, the rare earth element may substitute for nickel and combine with titanium to form a solid solution or a compound such as $Ti_xRE_y$. The nickel-titanium alloy may also include one or more other intermetallic compound phases of nickel and titanium, such as NiTi, $Ni_3Ti$ and/or $NiTi_2$, depending on the composition and heat treatment. The rare earth addition may form a ternary intermetallic compound phase with both nickel and titanium atoms, such as $Ni_xTi_yRE_z$. Some exemplary

TABLE 2

Preferred Alloy Compositions including Er and Cr (at. %)

| | | | | |
|---|---|---|---|---|
| $Ni_{50}Ti_{46}Er_4$ | $Ni_{50}Ti_{46}Er_{3.75}Cr_{0.25}$ | $Ni_{50}Ti_{46}Er_{3.5}Cr_{0.5}$ | $Ni_{50}Ti_{46}Er_{3.25}Cr_{0.75}$ | $Ni_{50}Ti_{46}Er_3Cr_1$ |
| $Ni_{51}Ti_{45}Er_4$ | $Ni_{51}Ti_{45}Er_{3.75}Cr_{0.25}$ | $Ni_{51}Ti_{45}Er_{3.5}Cr_{0.5}$ | $Ni_{51}Ti_{45}Er_{3.25}Cr_{0.75}$ | $Ni_{51}Ti_{45}Er_3Cr_1$ |
| $Ni_{52}Ti_{44}Er_4$ | $Ni_{52}Ti_{44}Er_{3.75}Cr_{0.25}$ | $Ni_{52}Ti_{44}Er_{3.5}Cr_{0.5}$ | $Ni_{52}Ti_{44}Er_{3.25}Cr_{0.75}$ | $Ni_{52}Ti_{44}Er_3Cr_1$ |
| $Ni_{53}Ti_{43}Er_4$ | $Ni_{53}Ti_{43}Er_{3.75}Cr_{0.25}$ | $Ni_{53}Ti_{43}Er_{3.5}Cr_{0.5}$ | $Ni_{53}Ti_{43}Er_{3.25}Cr_{0.75}$ | $Ni_{53}Ti_{43}Er_3Cr_1$ |
| $Ni_{54}Ti_{42}Er_4$ | $Ni_{54}Ti_{42}Er_{3.75}Cr_{0.25}$ | $Ni_{54}Ti_{42}Er_{3.5}Cr_{0.5}$ | $Ni_{54}Ti_{42}Er_{3.25}Cr_{0.75}$ | $Ni_{54}Ti_{42}Er_3Cr_1$ |
| $Ni_{55}Ti_{41}Er_4$ | $Ni_{55}Ti_{41}Er_{3.75}Cr_{0.25}$ | $Ni_{55}Ti_{41}Er_{3.5}Cr_{0.5}$ | $Ni_{55}Ti_{41}Er_{3.25}Cr_{0.75}$ | $Ni_{55}Ti_{41}Er_3Cr_1$ |
| $Ni_{56}Ti_{40}Er_4$ | $Ni_{56}Ti_{40}Er_{3.75}Cr_{0.25}$ | $Ni_{56}Ti_{40}Er_{3.5}Cr_{0.5}$ | $Ni_{56}Ti_{40}Er_{3.25}Cr_{0.75}$ | $Ni_{56}Ti_{40}Er_3Cr_1$ |

Palladium (Pd) may also be useful for suppressing the austenitic phase transformation temperature of the alloy, and it may further improve the radiopacity of the material. Accordingly, Pd may be included as an alloying element in place of or in addition to Cr. It may also be useful to include iron (Fe) in the alloy composition as a quaternary or higher order elemental addition, as iron can improve the hot workability of the nickel-titanium alloy.

Small amounts (e.g., hundreds of ppm) of non-metal elemental additions, such as, for example, C, H, N, or O, may also be present in the nickel-titanium alloy, although non-metallic elements are generally not included in the summation of alloying elements used to specify the composition of the alloy. Preferably, the amounts of C, O, and N are consistent with the American Society of Testing and Materials (ASTM) standard F2063, so as to avoid forming a high number density of and/or large-size carbide, oxide, nitride or complex carbonitride particles. This may result in a better electropolished surface and better fatigue life of the nickel-titanium alloy. H is preferably controlled per ASTM standard F2063 to minimize hydrogen embrittlement of the alloy. The aforementioned ASTM standards are hereby incorporated by reference.

phases in various Ni—Ti-RE alloys are identified below in Table 3. Also, in the event that one or more additional alloying elements are present in the nickel-titanium alloy, the additional alloying elements may form intermetallic compound phases with nickel, titanium, and/or the rare earth element.

TABLE 3

Exemplary Phases in Ni—Ti-RE Alloys

| Alloy | Exemplary Phases |
|---|---|
| Ni—Ti—Dy | DyNi, $DyNi_2$, $Dy_xTi_y$, $\alpha(Ti)$, $\alpha(Ni)$, $Ni_xTi_yDy_z$ |
| Ni—Ti—Er | ErNi, $ErNi_2$, $Er_xTi_y$, $\alpha(Ti)$, $\alpha(Ni)$, $Ni_xTi_yEr_z$ |
| Ni—Ti—Gd | GdNi, $GdNi_2$, $Gd_xTi_y$, $\alpha(Ti)$, $\alpha(Ni)$, $Ni_xTi_yGd_z$ |
| Ni—Ti—La | LaNi, $La_2Ni_3$, $La_xTi_y$, $\alpha(Ti)$, $\alpha(Ni)$, $Ni_xTi_yLa_z$ |
| Ni—Ti—Nd | NdNi, $NdNi_2$, $Nd_xTi_y$, $\alpha(Ti)$, $\alpha(Ni)$, $Ni_xTi_yNd_z$ |
| Ni—Ti—Yb | $YbNi_2$, $Yb_xTi_y$, $\alpha(Ti)$, $\alpha(Ni)$, $Ni_xTi_yYb_z$ |

The phase structure of the nickel-titanium alloy may be determined by experimental and/or computational methods. For example, diffraction methods, such as x-ray diffraction, neutron diffraction, and/or electron diffraction, may be employed. Alternatively, the CALPHAD method (CALculation of PHAse Diagrams) may be employed. Implementation of the CALPHAD method is discussed in "Thermodynamic Modeling of Multicomponent Phase Equilibria," *JOM* 49, 12 (1997) 14-19, which is hereby incorporated by reference. A number of commercially available software programs may be used to carry out the CALPHAD method, including, for example, ChemSage, MTDATA and Thermo-Calc. The Thermo-Calc program, for example, uses a combination of pre-existing published data on elements and data provided by the user in order to calculate phase diagrams. The program includes some pre-existing data for NiTi, while data and thermodynamic equations for rare earth systems obtained from the scientific literature may have to be provided. A ternary phase diagram can be constructed from these two sets of information. The process involves entering the known phase data, adding additional phases unknown to the program, and manipulating the interactions between the elements and phases. A set of equations derived from these manipulations may then be applied to invariant points or features of the phase diagram which are known or expected, and the program calculates the diagram from the given data, optimizing the given parameters to fit.

Ab initio superstructure calculations may be used to determine the energetics of the substitution mechanisms, that is, whether the rare earth element is substituting for nickel or titanium. These calculations also reveal the effect of the rare earth substitution on the mechanical properties of the energetically favorable configurations. Once the energetics of the alloys of interest are determined, semi-empirical interatomic potentials may be fit to the ab initio data and to available experimental data to describe the alloys. For example, these potential models may be utilized to predict and describe the dynamic behaviour of the nickel-titanium alloys, e.g., the dependence of phase stability on temperature and pressure (stress), which may be indicative of the $M_f$ and $A_f$ temperatures.

In selecting a desired alloy composition, the effect of the rare earth alloying element on various properties of the nickel-titanium alloy, including radiopacity, transformation temperatures ($M_f$, $M_s$, $R'_s$, $R'_f$, $R_s$, $R_f$, $A_s$, $A_f$), and mechanical properties, may be considered.

The radiopacity of a material is related to its linear absorption coefficient, $\mu$, which depends on its effective atomic number ($Z_{eff}$) and density ($\rho$), and on the energy (E) of the incoming x-ray photons:

$$\frac{\mu}{\rho} = const \cdot \frac{Z_{eff}^3}{E^3}$$

The linear absorption coefficient $\mu$ is proportional to the density $\rho$ of the material, and thus the quantity $$\frac{\mu}{\rho}$$

is a material constant known as the mass absorption coefficient and expressed in units of cm$^2$ g$^{-1}$.

Figure 2:
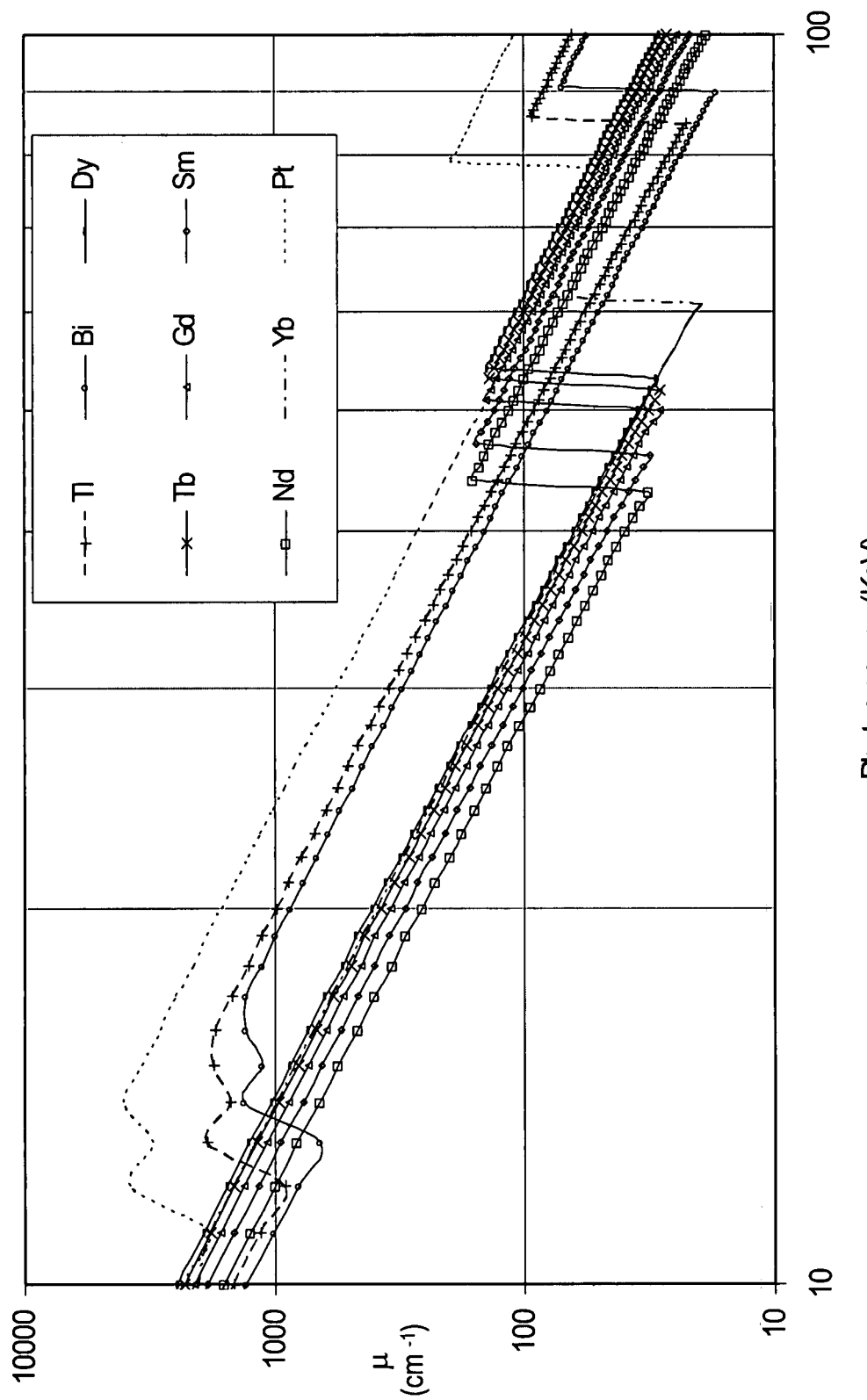
FIG. 2 is a graph of linear absorption coefficient versus photon energy for several rare earth (RE) elements and platinum.
Figure 3:
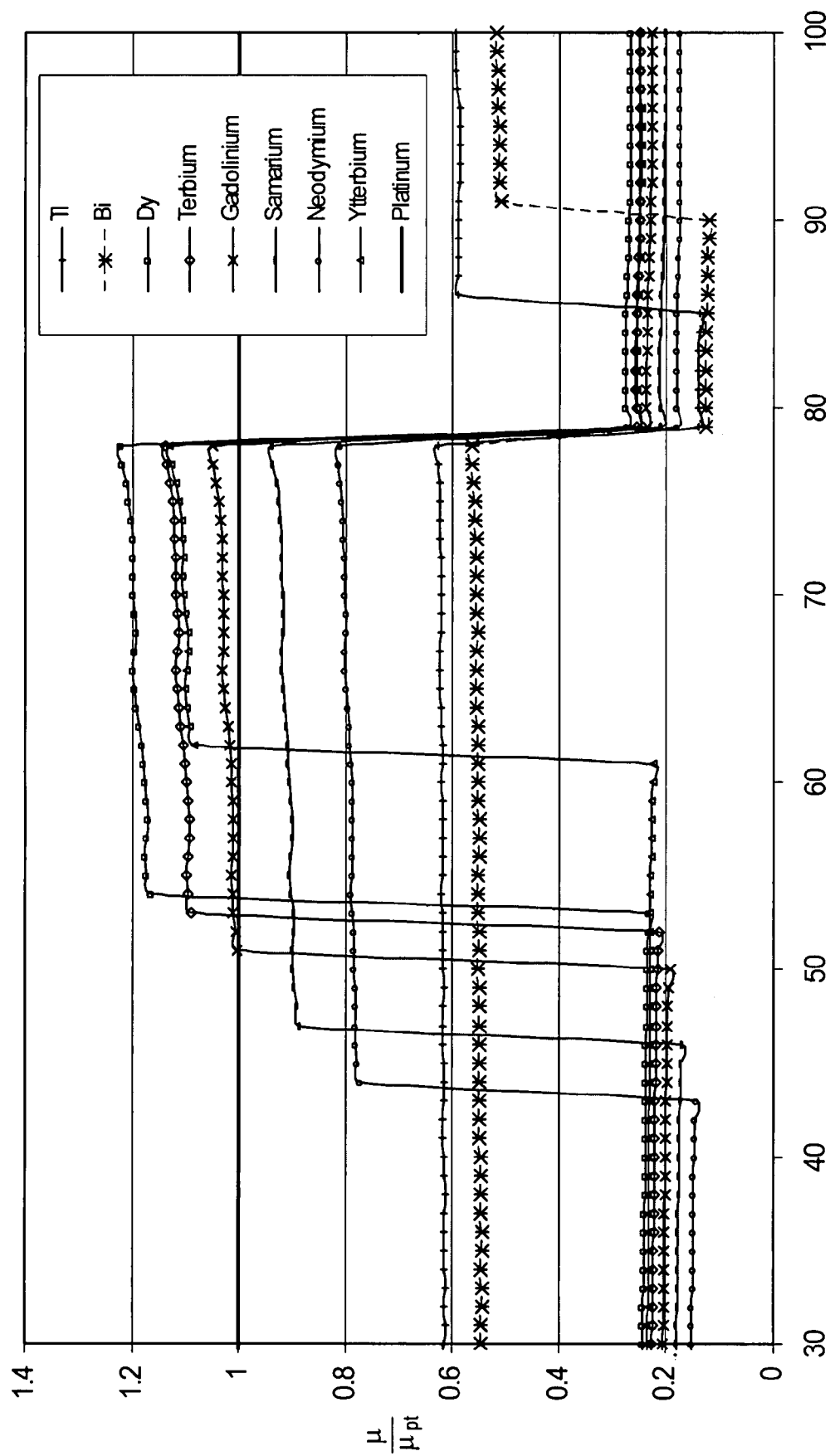
FIG. 3 is a graph of the linear absorption coefficient of FIG. 2 normalized with respect to the linear absorption coefficient of platinum versus photon energy.

Linear absorption coefficients $\mu$ were calculated for several rare earth elements and also for platinum for comparison. The results are shown in FIG. 2. In FIG. 3, the linear absorption coefficients $\mu$ are shown normalized with respect to the linear absorption coefficient of platinum $\mu_{Pt}$. The figures indicate that the absorption of the rare earth elements tends to peak in the photon energy range of about 40 to 80 keV, with some rare earth elements exceeding the absorption of platinum in this region.

Linear absorption coefficients were also calculated for several Ni—Ti-RE alloy compositions, as will be described below. The calculations were carried out under simulated x-ray conditions in order to evaluate the potential for rare earth alloying additions to improve the radiopacity of nickel-titanium medical devices.

To carry out a typical diagnostic x-ray procedure, a x-ray source or tube may be disposed in opposition to a patient with at least one filter placed between the source and the patient. A diagnostic x-ray tube typically has a built-in aluminum filter of about 2.5 mm in thickness per Food and Drug Administration (FDA) regulations, and additional filters may be used to achieve further filtering of the emitted x-ray beam. The x-ray photons may be generated when electrons from a tungsten filament are accelerated by a tube voltage and bombard a W or W/Re anode within the x-ray tube. Typically, for diagnostic procedures, the tube voltage is in the range of from about 50 kVp to about 150 kVp. The x-rays generated by the bombardment may pass through a beryllium window and through the one or more filters disposed between the source and the patient. The x-rays also experience a filtering or attenuation effect when passing through air and through tissues of the patient.

Figure 4A:
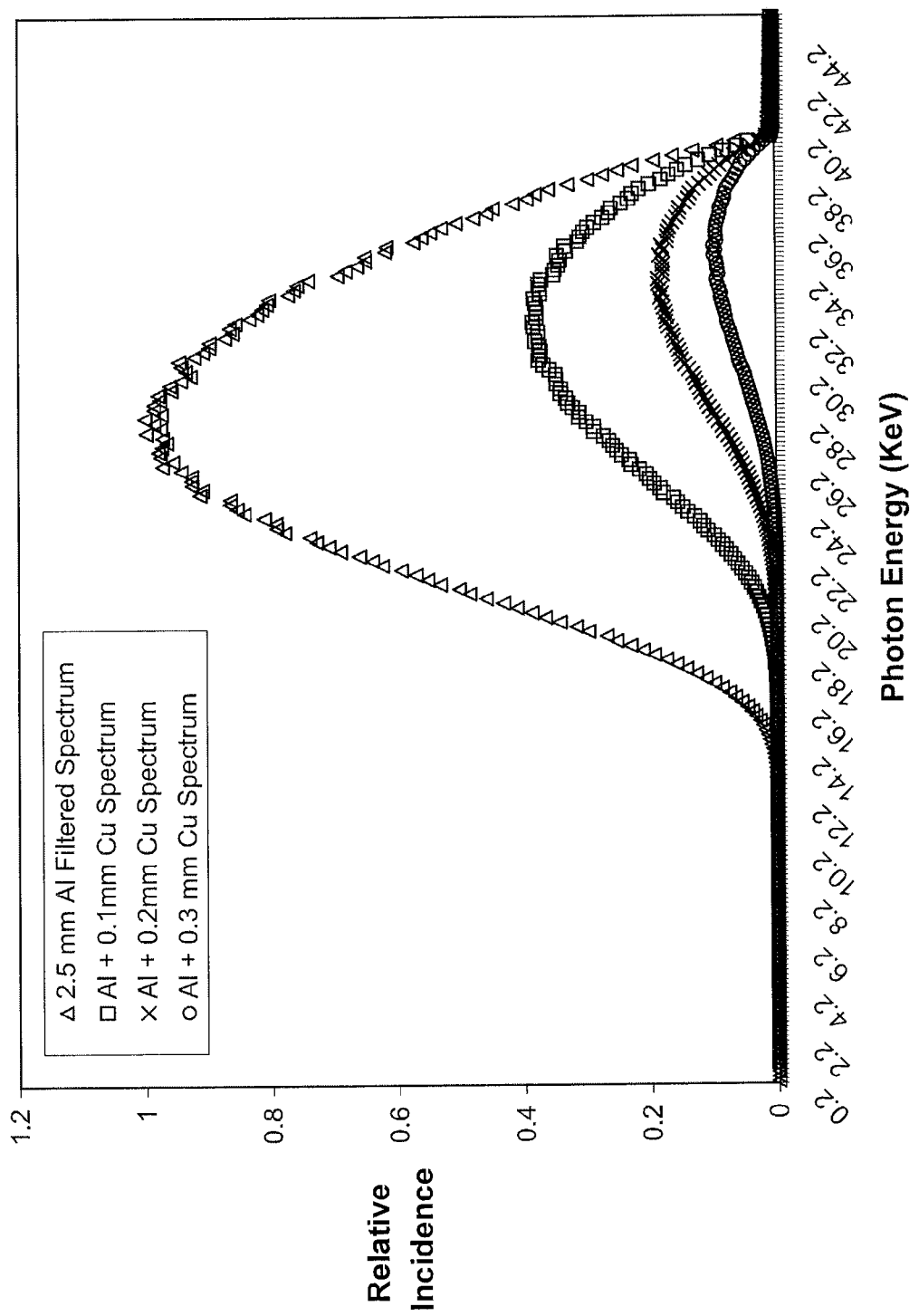
FIG. 4A is graph of relative incidence versus photon energy at a 40 kVp tube voltage for four different filtration levels.
Figure 4B:
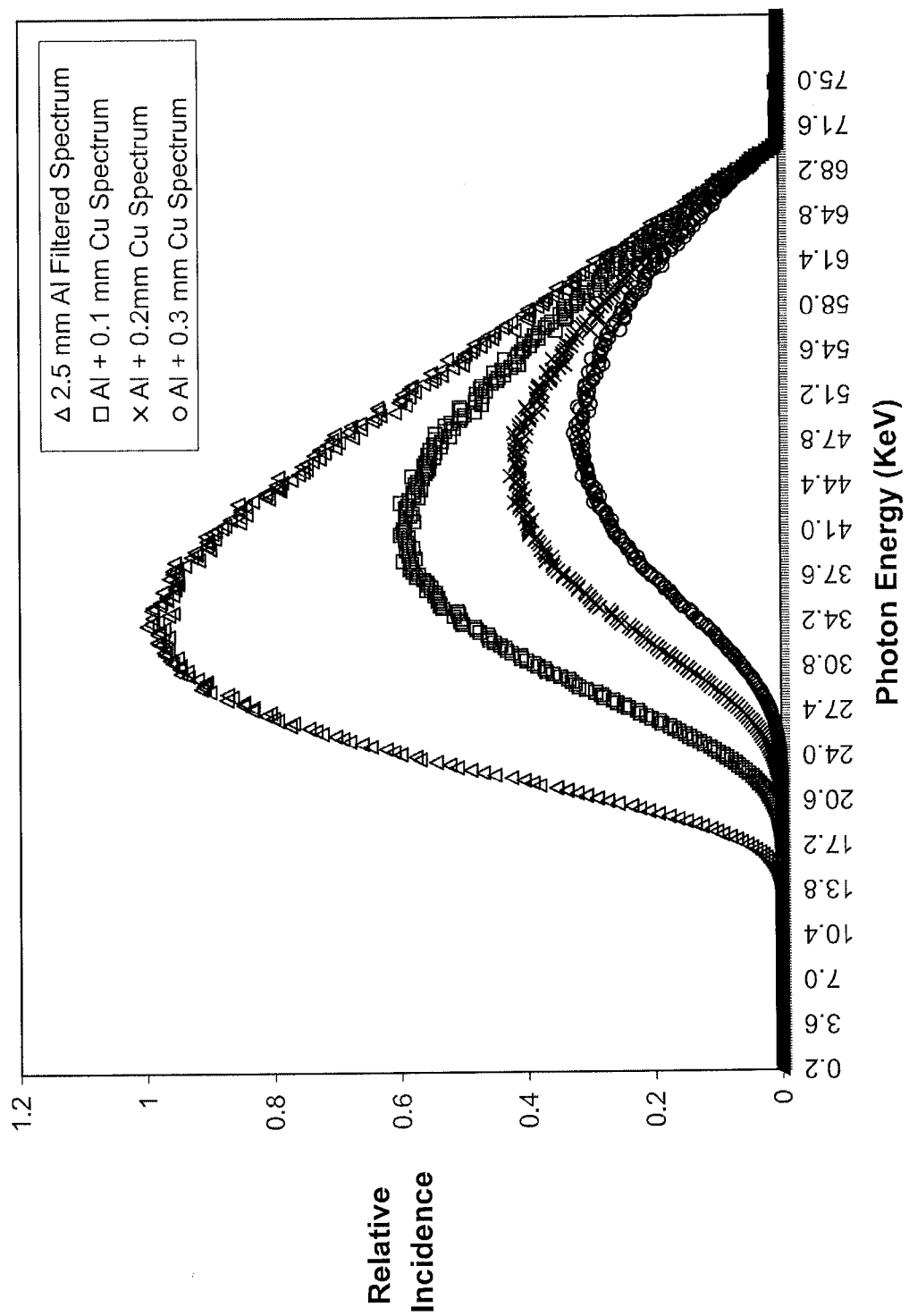
FIG. 4B is graph of relative incidence versus photon energy at a 70 kVp tube voltage for four different filtration levels.
Figure 4C:
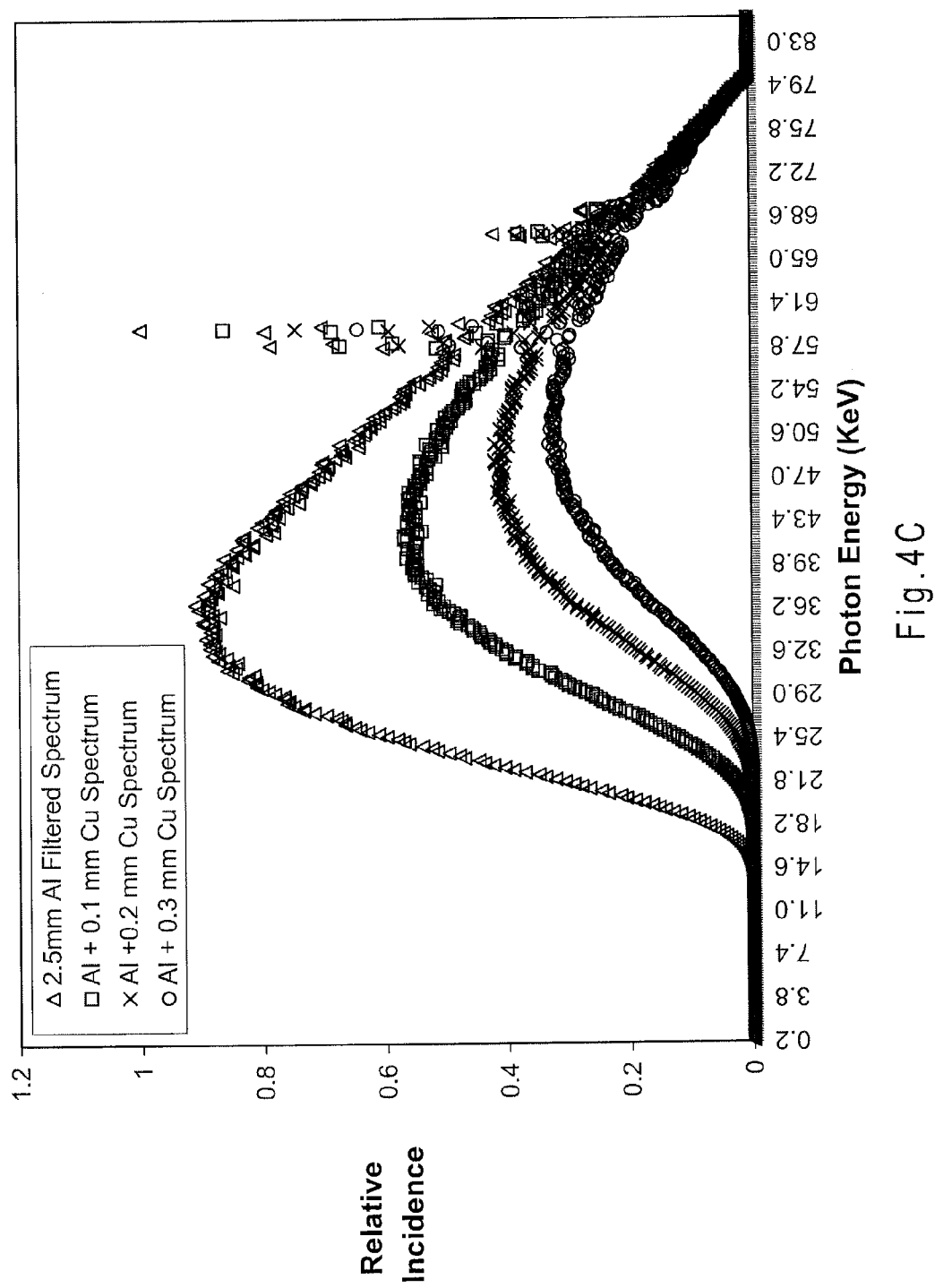
FIG. 4C is graph of relative incidence versus photon energy at a 80 kVp tube voltage for four different filtration levels.
Figure 4D:
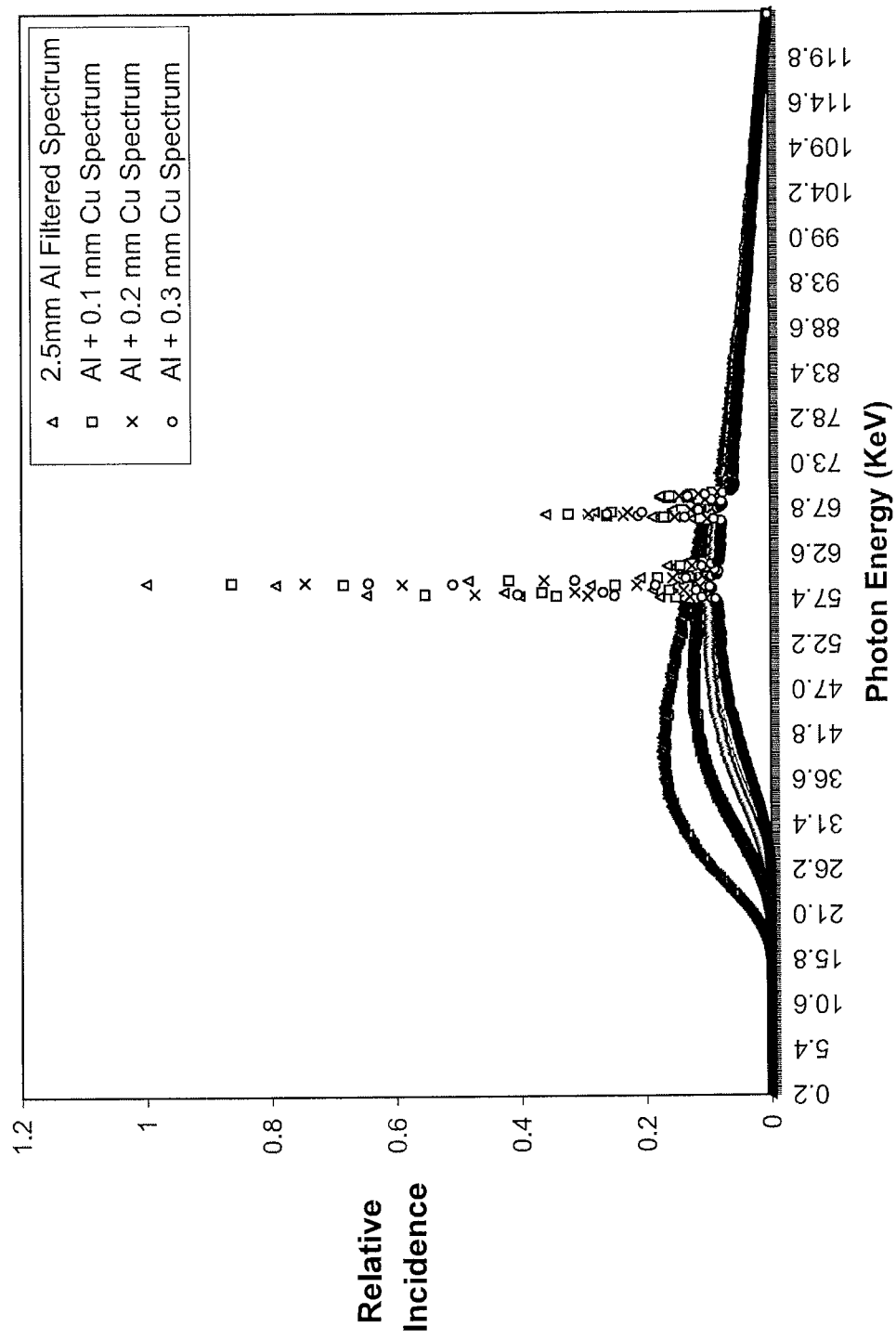
FIG. 4D is graph of relative incidence versus photon energy at a 125 kVp tube voltage for four different filtration levels.
Figure 5:
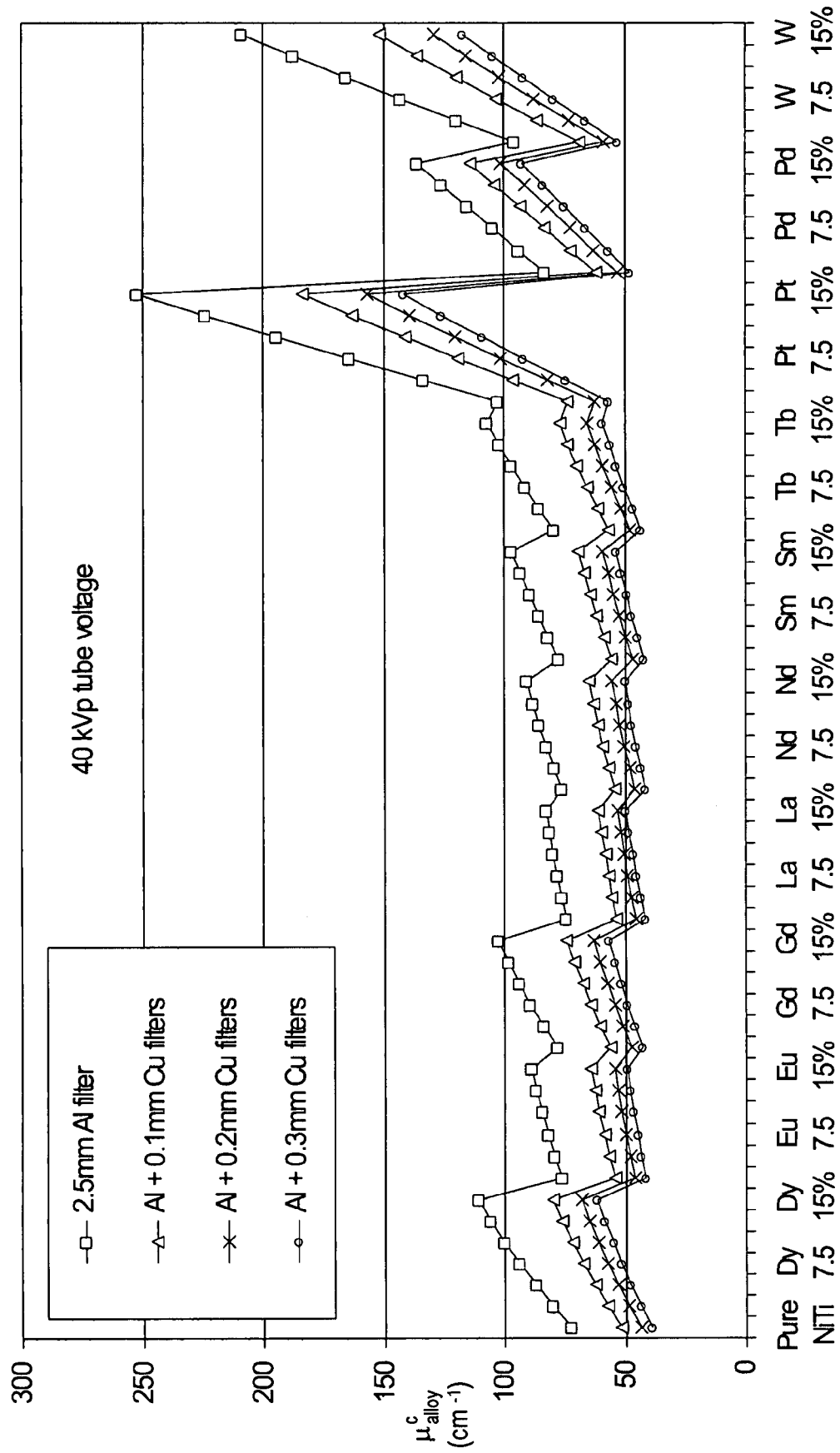
FIG. 5 is a graph of the calculated cumulative linear absorption coefficient of various Ni—Ti-RE alloys for a 40 kVp tube voltage and several filtration schemes.
Figure 6:
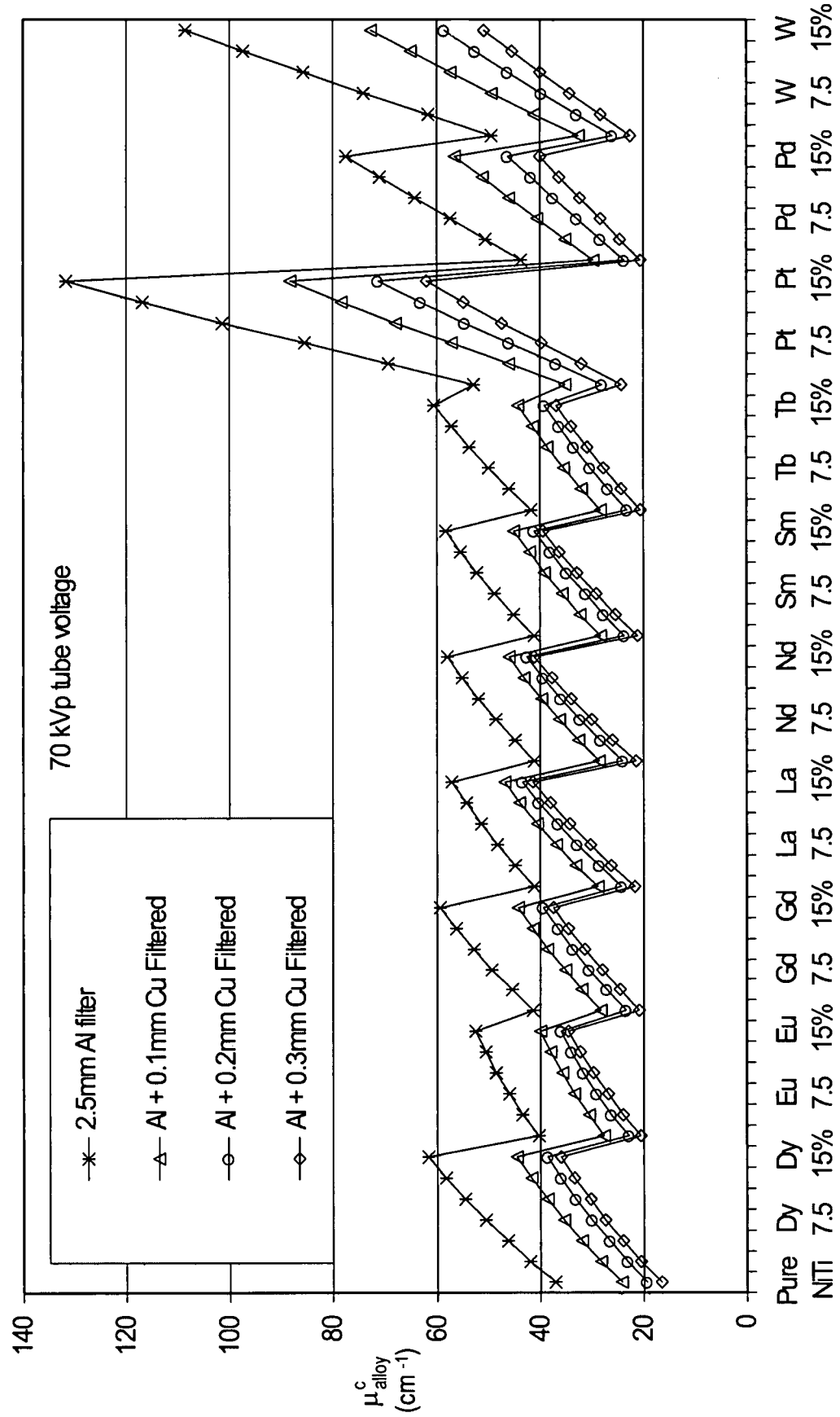
FIG. 6 is a graph of the calculated cumulative linear absorption coefficient (radiopacity) of various Ni—Ti-RE alloys for a 70 kVp tube voltage and several filtration schemes.
Figure 7:
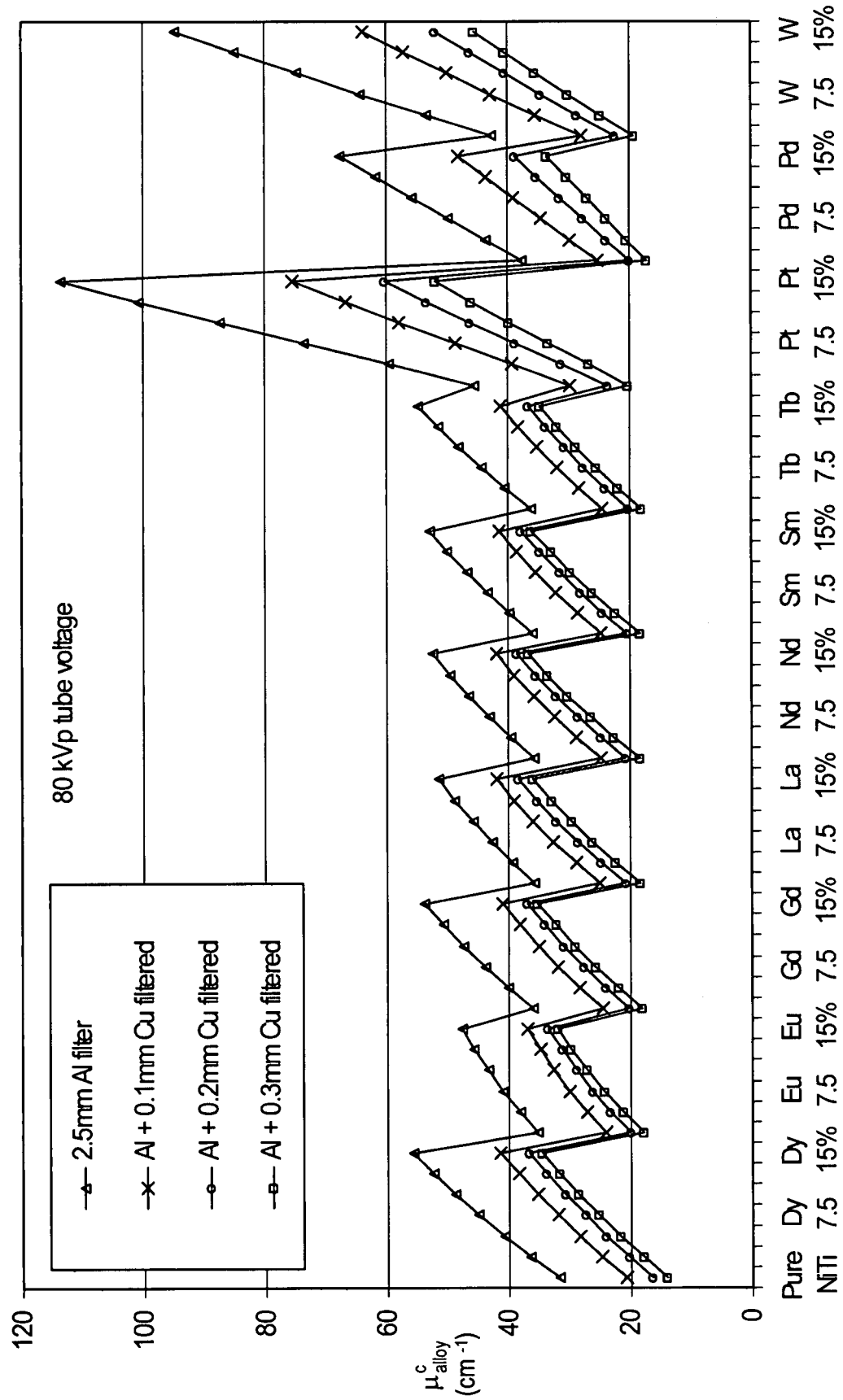
FIG. 7 is a graph of the calculated cumulative linear absorption coefficient (radiopacity) of various Ni—Ti-RE alloys for a 80 kVp tube voltage and several filtration schemes.
Figure 8:
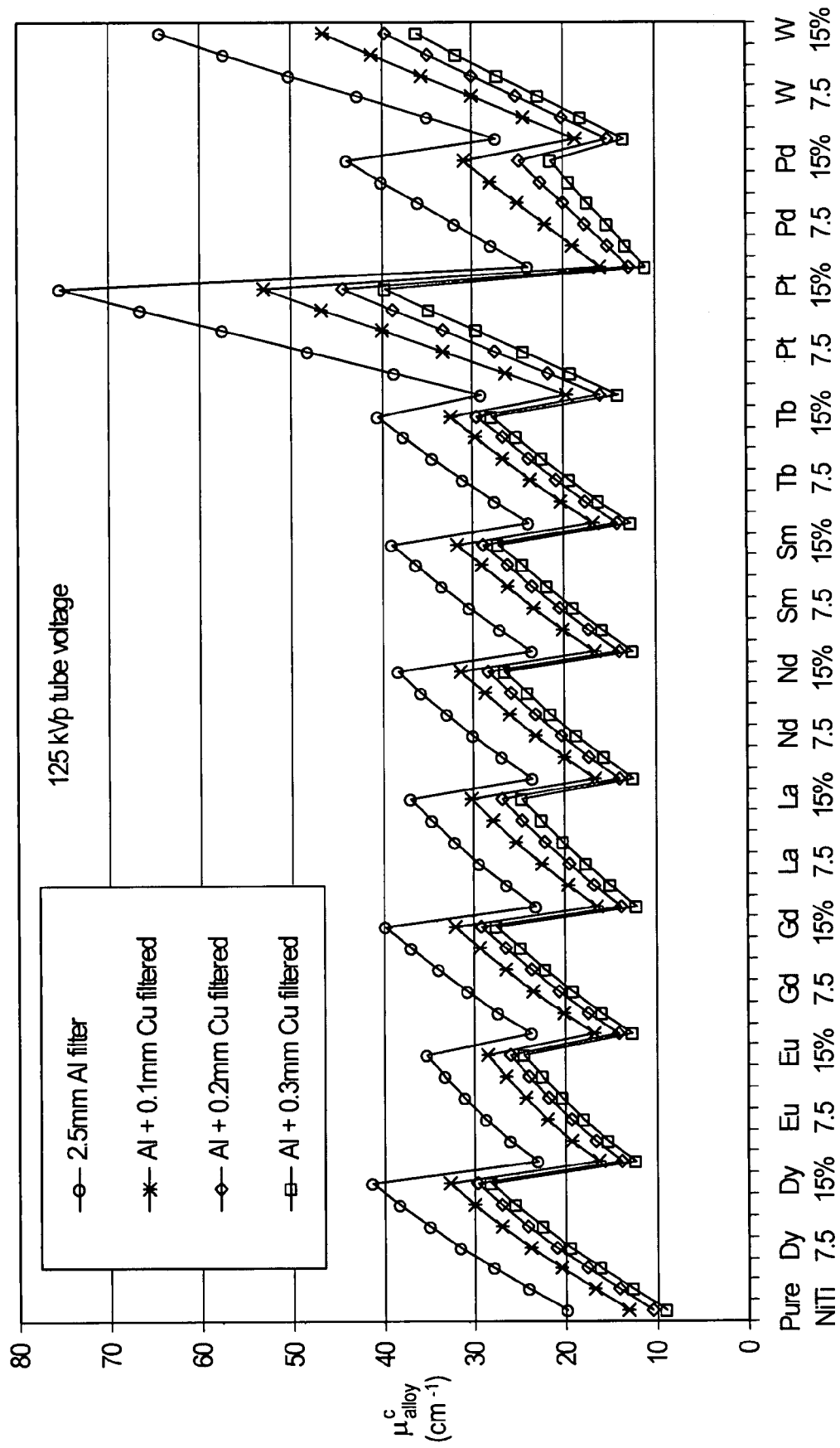
FIG. 8 is a graph of the calculated cumulative linear absorption coefficient (radiopacity) of various Ni—Ti-RE alloys for a 125 kVp tube voltage and several filtration schemes.
Figure 9:
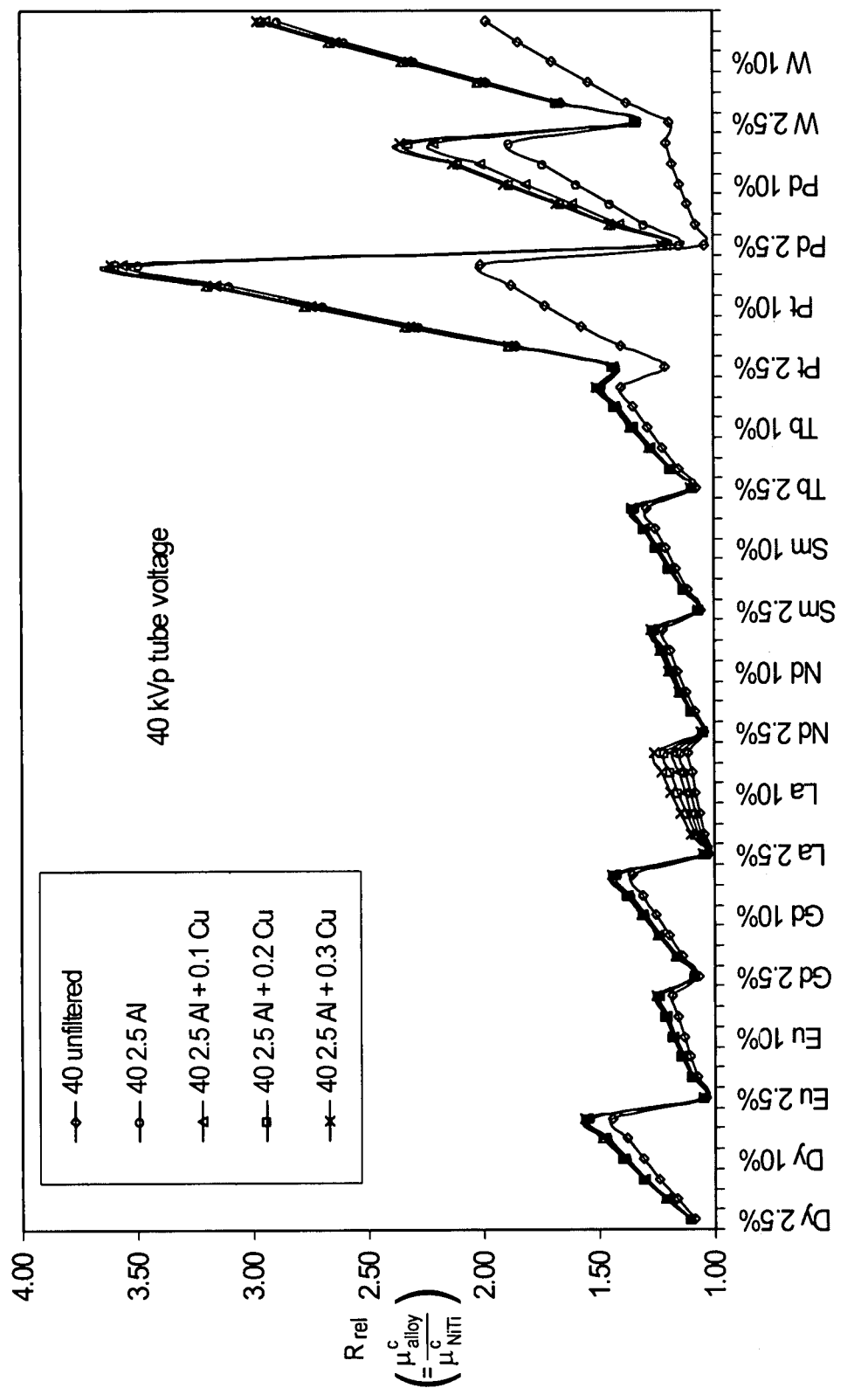
FIG. 9 is a graph of the radiopacity of various Ni—Ti-RE alloys relative to the radiopacity of a near-equiatomic binary nickel-titanium alloy for a 40 kVp tube voltage and several filtration schemes.
Figure 10:
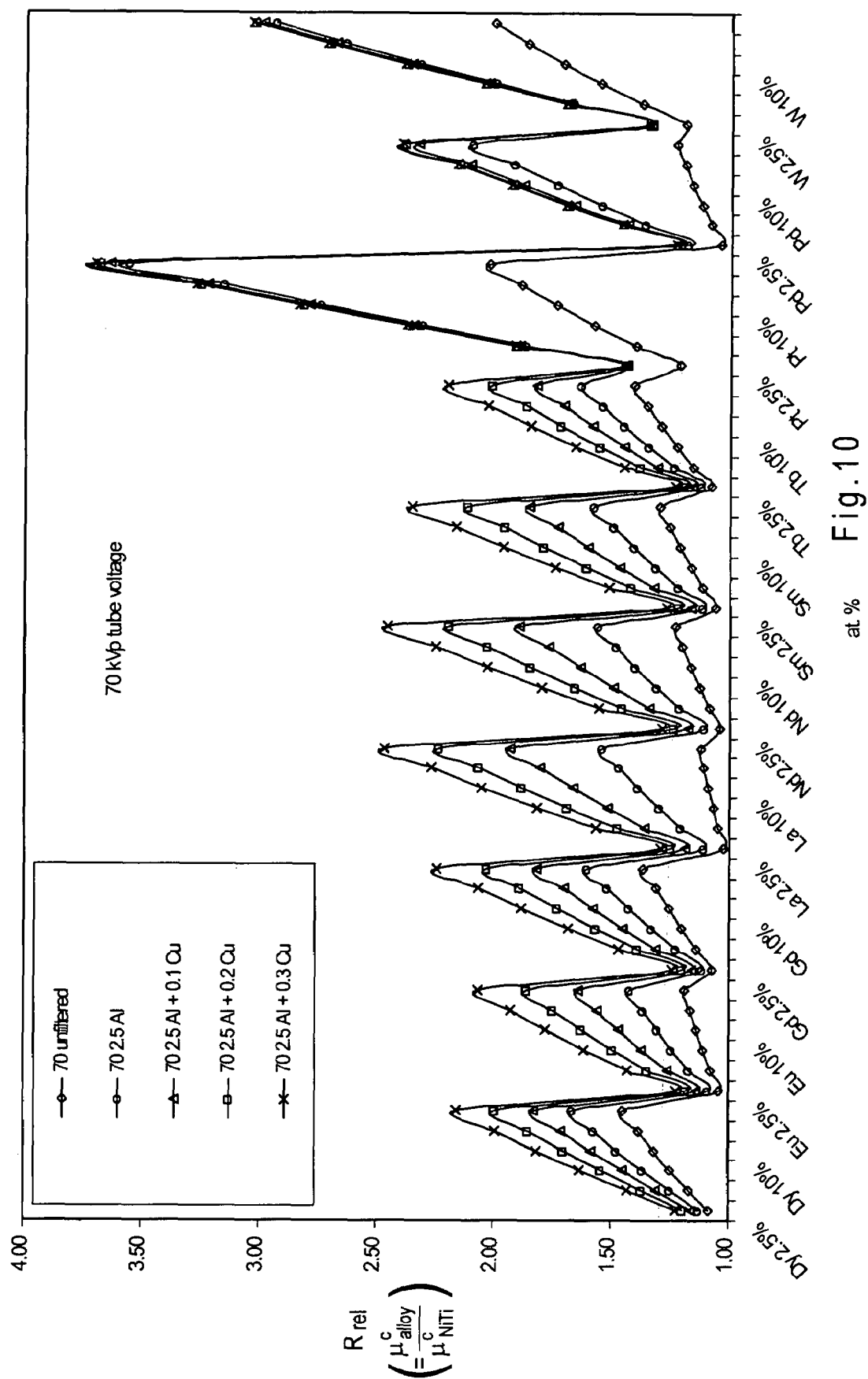
FIG. 10 is a graph of the radiopacity of various Ni—Ti-RE alloys relative to that of near-equiatomic binary nickel-titanium alloy for a 70 kVp tube voltage and several filtration schemes.
Figure 11A:
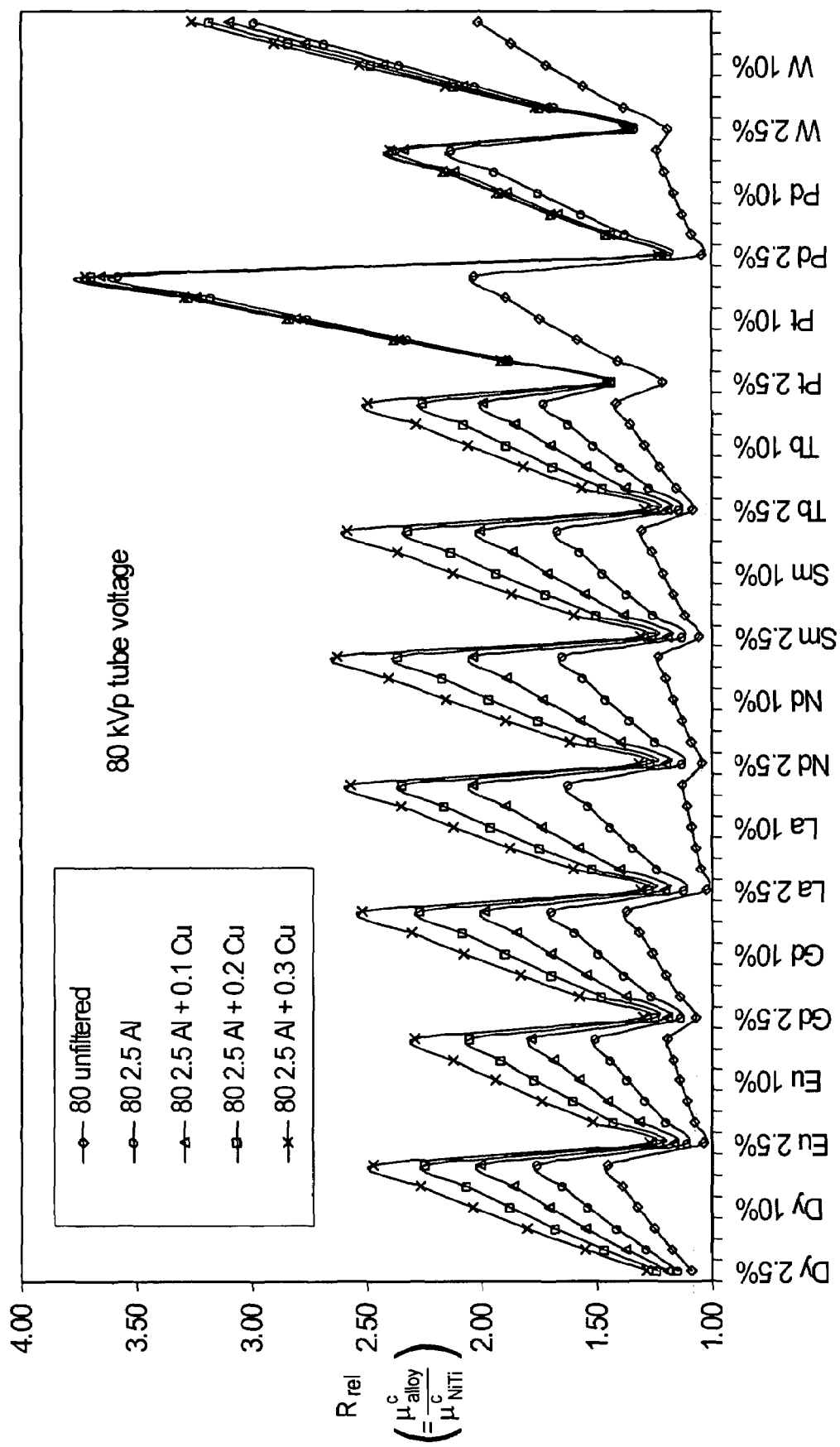
FIG. 11A and FIG. 11B are graphs of the radiopacity of various Ni—Ti-RE alloys relative to that of a near-equiatomic binary nickel-titanium alloy for a 80 kVp tube voltage and several filtration schemes.
Figure 11B:
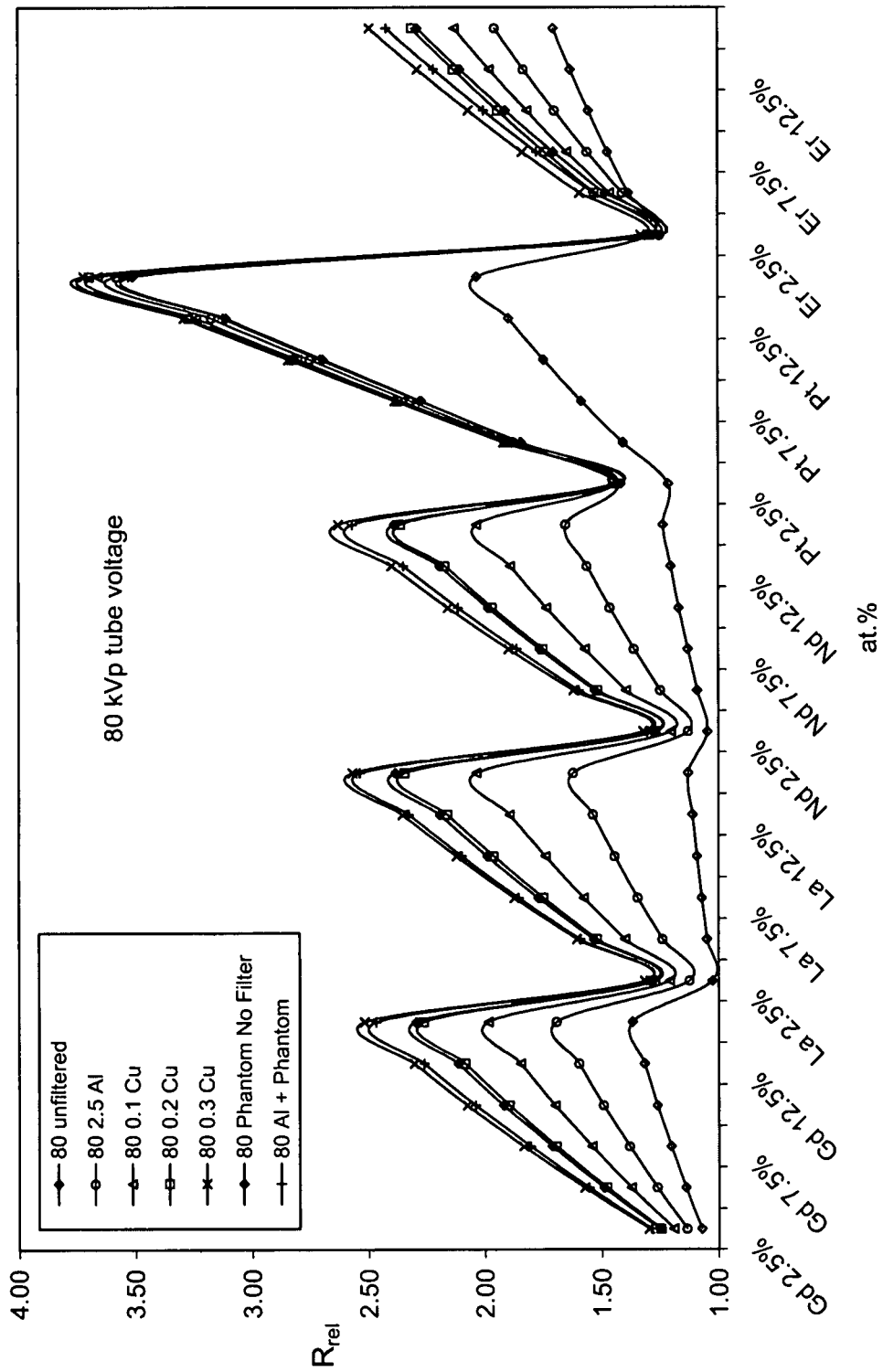
Figure 12:
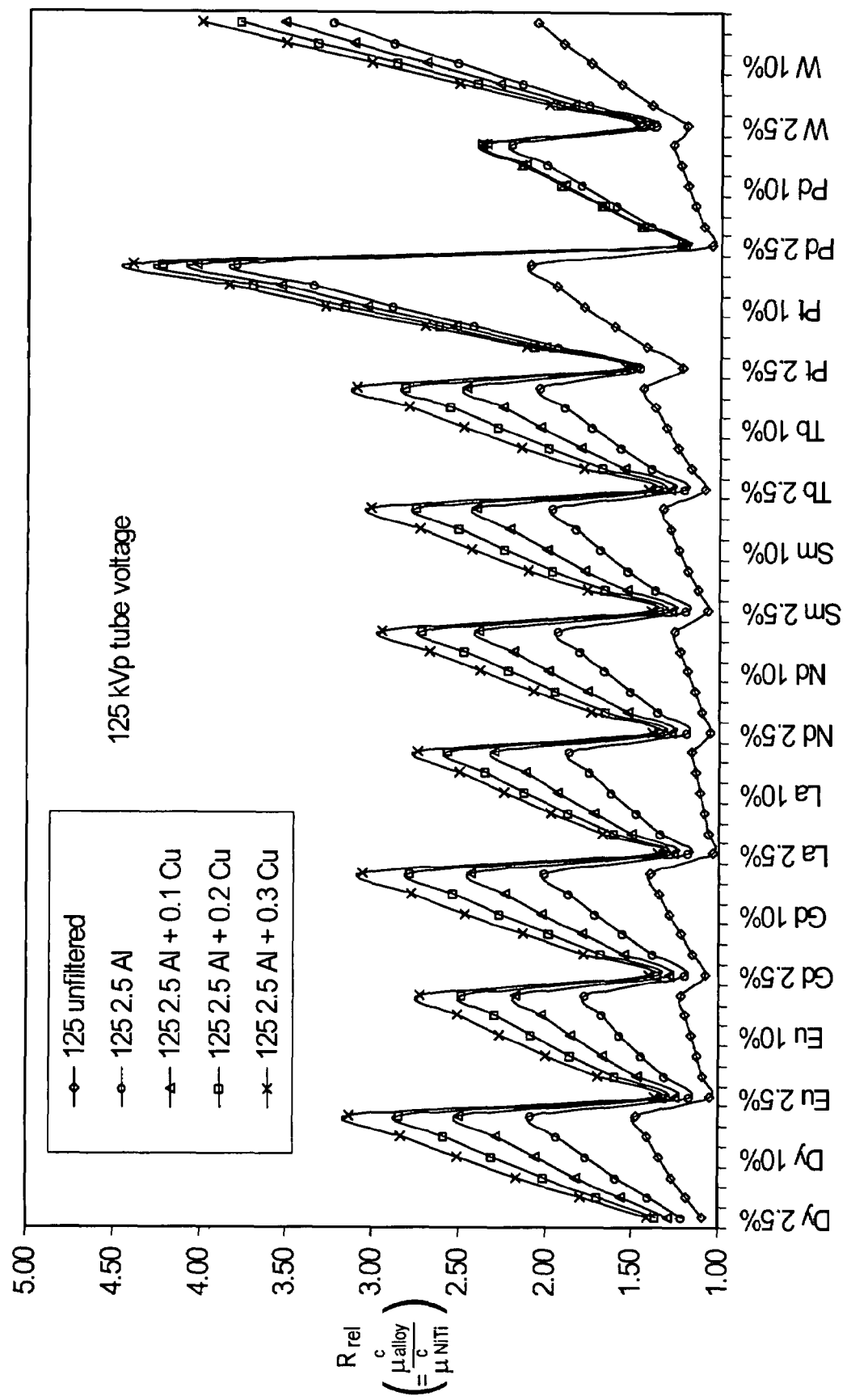
FIG. 12 is a graph of the radiopacity of various Ni—Ti-RE alloys relative to that of near-equiatomic binary nickel-titanium alloy for a 125 kVp tube voltage and several filtration schemes.

The x-ray beam emitted from the x-ray tube is not monochromatic, but rather includes a distribution of photons over a range of energies. Referring to FIGS. 4A-4D, the x-ray photons have a maximum energy corresponding to the tube voltage. For example, at a tube voltage of 70 kVp (see FIG. 4B), the maximum energy of the x-ray beam is 70 keV. The x-ray beam has a peak intensity (maximum number of photons) at an energy corresponding to about one-third of the maximum photon energy. The peak intensity may be shifted to higher energies, however, by the use of one or more filters. Other attenuation effects, such as passage of the x-ray beam through body tissue, may also cause a shift of the maximum intensity to higher energies, a phenomenon that may be referred to as beam hardening. For example, as shown in FIG. 4B, the peak intensity of the x-ray beam may be shifted to about 45 keV from about 35 keV by including a 0.2 mm copper filter in addition to a 2.5 mm aluminum filter between the x-ray source and the patient. By replacing the 0.2 mm copper filter with a 0.3 mm copper filter, the peak intensity of the x-ray beam may be shifted to about 50 keV. Generally speaking, the one or more filters may cause a shift of between 5 keV and 30 keV in the peak intensity of the radiation passing through the filter.

The intensity of x-rays transmitted through a material $I_x$ is related to the incident intensity $I_0$, material thickness x, and the linear absorption coefficient $\mu$:

$$I_x = I_0 e^{-\mu x}$$

Materials or tissues that substantially transmit incident x-rays are not readily visible in x-ray images. In contrast, radiopaque materials absorb incident x-rays over a given energy range and tend to show high contrast and good visibility in x-ray images. The magnitude of the linear absorption coefficient of a material may be a good indicator of its capacity for absorbing x-ray radiation, and thus its radiopacity.

Linear absorption coefficients were calculated for several Ni—Ti-RE alloy compositions using a software program called XMuDat developed by Robert Nowotny of the Institut f. Biomed. Technik und Physik at the University of Wien, Wien, Austria. XMuDat is a computer program for the presentation and calculation of various photon interaction coefficients for materials of dosimetric interest. Data for mass attenuation-, mass energy transfer- and mass energy absorption coefficients in a photon energy range of 1 keV to 50 MeV are available. For calculation the program uses photon interaction coefficients collected from J M. Boone, A E. Chavez; *Medical Physics* 23, 12 (1996) 1997-2005.

The effects of various diagnostic x-ray tube voltages and filtration schemes were considered, as summarized in Table 4 below. The raw data for unfiltered photons at various tube voltages were taken from Horst Aichinger, Joachim Dierker, Sigrid Joite-Barfuβ and Manfred Säbel, *Radiation Exposure and Image Quality in X-Ray Diagnostic Radiology: Physical Principles and Clinical Applications*, Springer: Berlin. The polychromatic nature of the x-ray beam generated from a W/Re anode and the role of beam attenuation with various filters were also taken into account.

TABLE 4

Parameters of Linear Absorption Coefficient Calculations

| Parameter | Range Considered |
| --- | --- |
| Tube voltage | 40 kVp-125 kVp |
| Filtration | Unfiltered |
|  | 2.5 mm Al |
|  | 2.5 mm Al + 0.1 mm Cu |
|  | 2.5 mm Al + 0.2 mm Cu |
|  | 2.5 mm Al + 0.3 mm Cu |
| Rare earth (RE) addition | Dy, Eu, Gd, La, Nd, Sm, Tb |
| Concentration of RE addition | 2.5, 5, 7.5, 10, 12.5, and 15 at. % |

As a first step in the calculations, mass absorption coefficients $A_{alloy}$ for various alloy compositions were calculated using a rule of mixtures approach:

$$A_{alloy} = pA_{Ni} = qA_{Ti} + rA_{RE}$$

where $$p = \frac{aM_{Ni}}{(aM_{Ni} + bM_{Ti} + cM_{RE})}$$

$$q = \frac{bM_{Ti}}{(aM_{Ni} + bM_{Ti} + cM_{RE})}$$

$$r = \frac{cM_{RE}}{(aM_{Ni} + bM_{Ti} + cM_{RE})}$$

The variables $A_{Ni}$, $A_{Ti}$, and $A_{RE}$ represent elemental mass absorption coefficients, which are equivalent to $$\frac{\mu}{\rho}$$

for each element. The variables $M_{Ti}$, $M_{Ni}$, and $M_{RE}$ represent the molecular weight of each element and a, b, and c are atomic percentages of each element in the alloy. It was assumed in estimating the atomic percentages that the rare earth element substituted for titanium. This assumption was made based on the closer proximity of the rare earth elements to titanium than to nickel in the periodic table. Since the radiopacity of nickel is comparable to the radiopacity of titanium in the energy range of interest for diagnostic x-ray procedures, the specifics of the substitution are believed to be less important than the atomic percentage of the rare earth element in the Ni—Ti-RE alloy.

Once the mass absorption coefficient $A_{alloy}$ was obtained for a given alloy composition, the linear absorption coefficient $\mu_{alloy}$ was calculated as the product of $A_{alloy}$ and the density $\rho_{alloy}$ of the alloy. The density $\rho_{alloy}$ was calculated using the same rule of mixtures approach as above.

Next, a cumulative linear absorption coefficient $\mu_{alloy}^C$ was calculated for each alloy composition to take into account the polychromatic nature of the x-ray beam. Using x-ray intensity distributions for a W/Re anode at various x-ray tube voltages and with different levels of filtration, photon probability distributions were calculated. Cumulative linear absorption coefficients $\mu_{alloy}^C$ were obtained for various tube voltages and filtration levels by multiplying the values of $\mu_{alloy}$ determined above by the respective photon probability at a given energy and then summing the values over the entire energy spectrum. The resulting values of $\mu_{alloy}^C$, or radiopacity, are shown in graphical form in FIGS. 5-8 for various Ni—Ti-RE alloy compositions in atomic percent (at. %), tube voltages and filtration schemes. Calculated data are also presented for Ni—Ti—Pt, Ni—Ti—Pd, and Ni—Ti—W alloys for comparison.

It is desirable that the Ni—Ti-RE alloys exhibit improved radiopacity compared to a binary Nitinol alloy. Therefore, the cumulative linear absorption coefficients $\mu_{alloy}^C$ obtained for various Ni—Ti-RE alloy compositions were normalized to the cumulative linear absorption coefficient $\mu_{NiTi}^C$ of binary Nitinol, thus obtaining values of relative radiopacity $R_{rel}$, i.e., $$\left(R_{rel} = \frac{\mu_{alloy}^C}{\mu_{NiTi}^C}\right).$$

Figure 20:
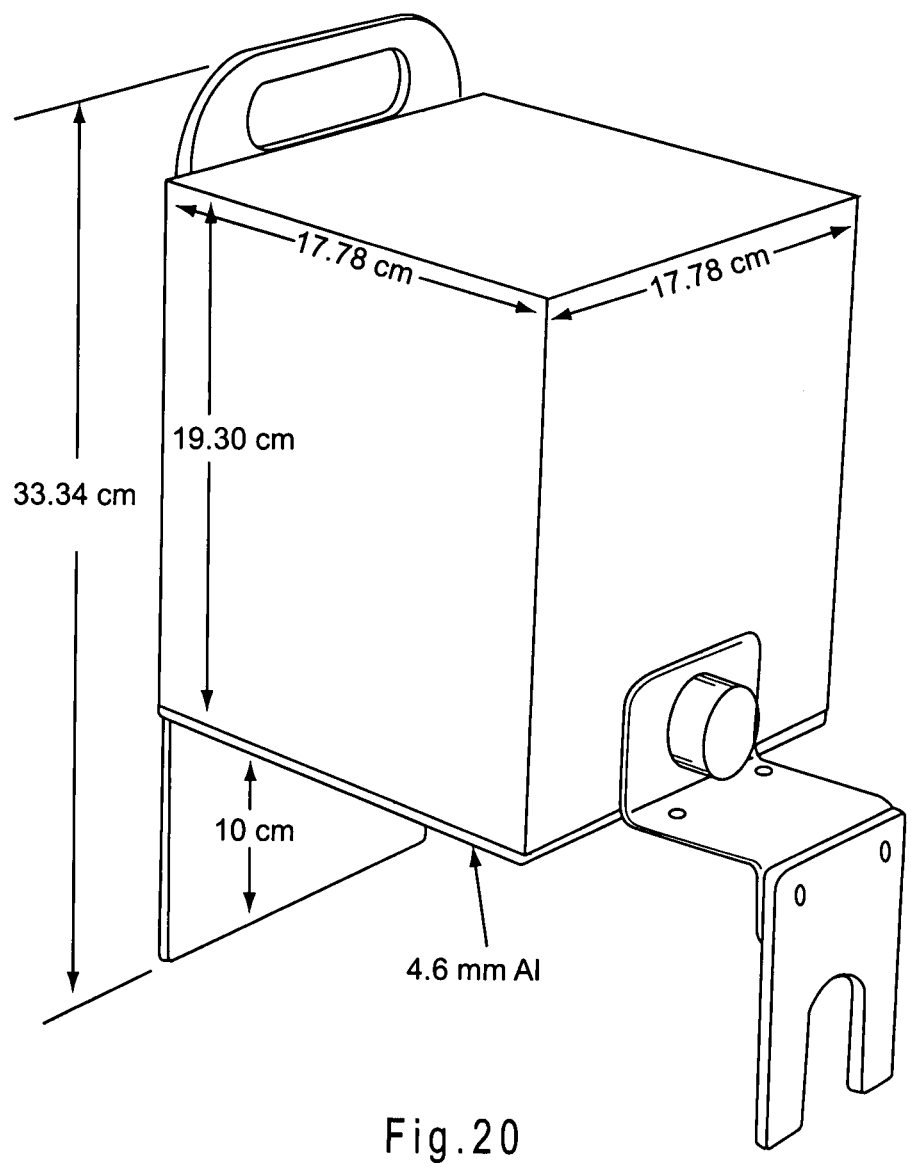
FIG. 20 is a schematic of a phantom developed by the Center for Devices and Radiological Health (CDRH) to simulate x-ray attenuation through the lower abdomen of a typical adult.

A slightly nickel-rich composition of 50.6 at. % Ni was assumed in calculating $\mu_{NiTi}^C$ for binary Nitinol. Using this approach, it is possible to compare the radiopacity of the Ni—Ti-RE alloys to the radiopacity of a near-equiatomic binary Ni—Ti alloy. The relative radiopacity values $R_{rel}$ are shown in graphical form in FIGS. 9-12 for various Ni—Ti-RE alloy compositions in atomic percent (at. %), tube voltages and filtration schemes (e.g., unfiltered, Al filter, Cu filter, or CDRH phantom, which is described later and shown in FIG. 20). Calculated data are also presented for Ni—Ti—Pt, Ni—Ti—Pd, and Ni—Ti—W alloys for comparison.

Referring to the calculated data shown in FIGS. 9-12, it can be observed that the radiopacity of the Ni—Ti-RE alloys is greater than that of a near-equiatomic binary nickel-titanium alloy. The Ni—Ti-RE alloys have a cumulative absorption coefficient $\mu_{alloy}^C$ (radiopacity) ranging from greater than about 1 to about 3.2 times that of a near-equiatomic binary nickel-titanium alloy when exposed to radiation having an energy in the range of from 15 keV to 125 keV. This is shown, for example, in FIG. 12, which corresponds to a tube voltage of 125 kVp. The Ni—Ti-RE alloys have a cumulative absorption coefficient $\mu_{alloy}^C$ (radiopacity) ranging from greater than about 1 to about 2.7 times that of a near-equiatomic binary nickel-titanium alloy when exposed to radiation having an energy in the range of from 15 keV to 80 keV, as shown, for example, in FIG. 11A, which corresponds to a tube voltage of 80 kVp. The Ni—Ti-RE alloys have a cumulative absorption coefficient $\mu_{alloy}^C$ (radiopacity) ranging from greater than about 1 to about 2.5 times that of a near-equiatomic binary nickel-titanium alloy when exposed to radiation having an energy in the range of from 15 keV to 70 keV, as shown, for example, in FIG. 10, which corresponds to a tube voltage of 70 kVp.

By using more than one rare earth element and/or additional alloying elements in the nickel-titanium alloy, the radiopacity may be increased in a cumulative manner consistent with the radiopacity of the individual alloying elements.

Preferably, the nickel-titanium alloy has a radiopacity in the range of from greater than about 1 to about 8 times that of a near-equiatomic binary nickel-titanium alloy (i.e., the relative radiopacity $R_{rel}$ is in the range of from about 1 to about 8) when exposed to radiation having an energy in the range of from 15 keV to 150 keV. The radiopacity of the nickel-titanium alloy may also be in the range of from greater than about 1 to about 8 times that of a near-equiatomic binary nickel-titanium alloy when the alloys are exposed to radiation in the range of from 15 keV to 125 keV. According to other embodiments, the radiopacity may be in the range of from greater than about 1 to about 8 times that of a near-equiatomic binary nickel-titanium alloy when the alloys are exposed to radiation in the range of from 15 keV to 80 keV, from 15 keV to 70 keV, or from 15 keV to 60 keV.

More preferably, the nickel-titanium alloy has a radiopacity in the range of from about 1.2 to about 8 times that of a near-equiatomic binary nickel-titanium alloy (i.e., the relative radiopacity $R_{rel}$ is in the range of from about 1.2 to about 8) when exposed to radiation having an energy in the range of from 15 keV to 150 keV. The radiopacity of the nickel-titanium alloy may also be in the range of from about 1.2 to about 8 times that of a near-equiatomic binary nickel-titanium alloy when the alloys are exposed to radiation in the range of from 15 keV to 125 keV. According to other embodiments, the radiopacity may be in the range of from about 1.2 to about 8 times that of a near-equiatomic binary nickel-titanium alloy when the alloys are exposed to radiation in the range of from 15 keV to 80 keV, from 15 keV to 70 keV, or from 15 keV to 60 keV.

Even more preferably, the nickel-titanium alloy has a radiopacity in the range of from about 1.2 to about 5 times that of a near-equiatomic binary nickel-titanium alloy (i.e., the relative radiopacity $R_{rel}$ is in the range of from about 1.2 to about 5) when exposed to radiation having an energy in the range of from 15 keV to 150 keV. The radiopacity of the nickel-titanium alloy may also be in the range of from about 1.2 to about 5 times that of a near-equiatomic binary nickel-titanium alloy when the alloys are exposed to radiation in the range of from 15 keV to 125 keV. According to other embodiments, the radiopacity may be in the range of from about 1.2 to about 5 times that of a near-equiatomic binary nickel-titanium alloy when the alloys are exposed to radiation in the range of from 15 keV to 80 keV, from 15 keV to 70 keV, or from 15 keV to 60 keV.

It may be even more advantageous if the radiopacity of the nickel-titanium alloy is in the range of from about 1.5 to about 5 times greater than that of a near-equiatomic binary nickel-titanium alloy when the alloys are exposed to radiation having an energy within any of the above-mentioned ranges (i.e., from 15 keV to 150 keV, from 15 keV to 125 keV, from 15 keV to 80 keV, from 15 keV to 70 keV, or from 15 keV to 60 keV).

According to a preferred embodiment, the nickel-titanium alloy has a radiopacity in the range of from greater than about 1 to about 8 times that of a near-equiatomic binary nickel-titanium alloy when exposed to radiation having a peak intensity at an energy in the range of from 30 keV to 60 keV. It is also preferable that the radiopacity of the nickel-titanium alloy is in the range of from greater than about 1 to about 8 times that of a near-equiatomic binary nickel-titanium alloy when exposed to radiation having a peak intensity at an energy in the range of from 35 keV to 55 keV, or from 40 keV to 50 keV.

According to another preferred embodiment, the nickel-titanium alloy has a radiopacity in the range of from greater than about 1.2 to about 5 times that of a near-equiatomic binary nickel-titanium alloy when exposed to radiation having a peak intensity at an energy in the range of from 30 keV to 60 keV. It is also preferable that the radiopacity of the nickel-titanium alloy is in the range of from greater than about 1.2 to about 5 times that of a near-equiatomic binary nickel-titanium alloy when exposed to radiation having a peak intensity at an energy in the range of from 35 keV to 55 keV, or from 40 keV to 50 keV.

Again referring to the calculated data shown in FIGS. 9-12, the radiopacity of the Ni—Ti-RE alloys is comparable to or better than that of Ni—Ti—Pd at a tube voltage in the range of from 70 kVp to 125 kVp, depending on the filter selection. FIGS. 9-12 correspond to tube voltages of 40 kVp, 70 kVp, 80 kVp, and 125 kVp, respectively. Referring to FIG. 11A, for example, a nickel-titanium alloy including 7.5 at. % Nd has a relative radiopacity $R_{rel}$ of approximately 1.9 when a 2.5 mm Al filter and 0.3 mm Cu filter are used, whereas a nickel-titanium alloy including 7.5 at. % Pd has a relative radiopacity $R_{rel}$ of about 1.7 under the same conditions. Preferably, the radiopacity of the Ni—Ti-RE alloys is comparable to or better than that of Ni—Ti—Pd at a tube voltage in the range of from 60 kVp to 150 kVp.

It also can be observed from the calculated data that the radiopacity of the Ni—Ti-RE alloys increases at higher concentrations of the rare earth alloying addition. Referring again to FIG. 11A, for example, the maximum radiopacity (largest value of $\mu_{rel}^C$) for each alloy composition is achieved at the highest rare earth element concentration (15 at. %) considered in the calculations.

In addition to considering the impact of the rare earth element(s) on the radiopacity of the nickel-titanium alloy, it is also desirable to consider the impact on the superelastic and mechanical properties of the alloy. The improved radiopacity achieved at high concentrations of rare earth elements preferably may be balanced against the effects of high concentrations of alloying elements on the superelastic and mechanical properties of the nickel-titanium alloy.

According to a preferred embodiment, the nickel-titanium alloy exhibits superelastic or shape memory behavior. That is, the nickel-titanium alloy undergoes a reversible phase transformation that allows it to "remember" and return to a previous shape or configuration. The nickel-titanium alloy transforms between a lower temperature phase (martensite) and a higher temperature phase (austenite). Austenite is characteristically the stronger phase, and martensite may be deformed up to a recoverable strain of about 8%. Strain introduced in the alloy in the martensitic phase to achieve a shape change may be substantially recovered upon completion of a reverse phase transformation to austenite, allowing the alloy to return to a previous shape. The strain recovery may be driven by the application and removal of stress (superelastic effect) and/or by a change in temperature (shape memory effect).

Figure 13:
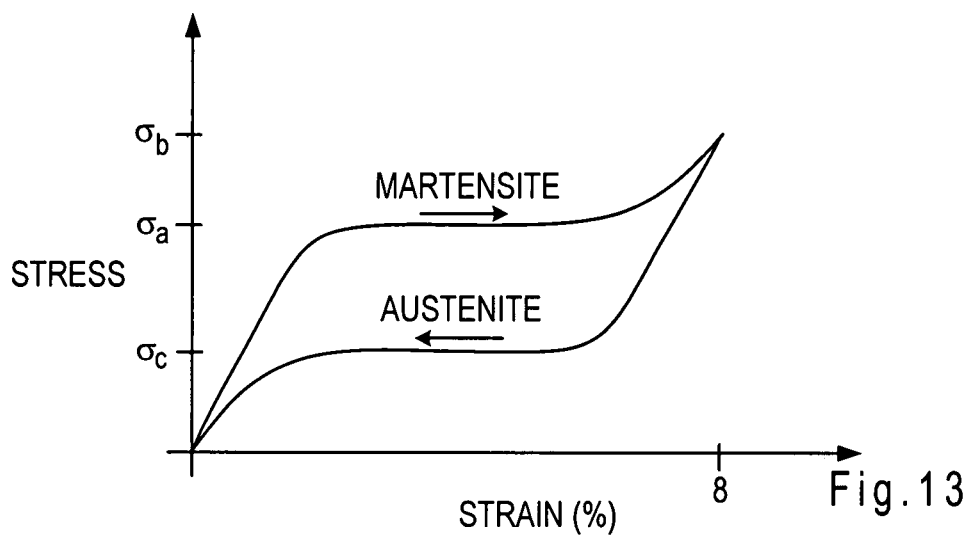
FIG. 13 is a diagram of stress versus strain for an exemplary shape memory alloy at a temperature above an austenitic final temperature of the alloy.

The stress-strain diagram in FIG. 13 illustrates the superelastic effect for an exemplary nickel-titanium alloy at a temperature above the austenitic final temperature ($A_f$) of the alloy. Upon application of a stress $\sigma_a$, an alloy in a first configuration begins to transform from austenite to martensite as a result of the formation of stress-induced martensite. The martensitic phase of the alloy can accommodate several percent strain at a nearly constant stress. At a stress of $\sigma_b$, which corresponds to 8% strain in this example, the martensitic transformation is complete and the alloy has been deformed to a second configuration. Upon release of the stress, the martensite begins to transform back to austenite and the alloy recovers the strain at a lower plateau stress of $\sigma_c$. The nickel-titanium alloy thus returns to the first configuration.

Figure 14:
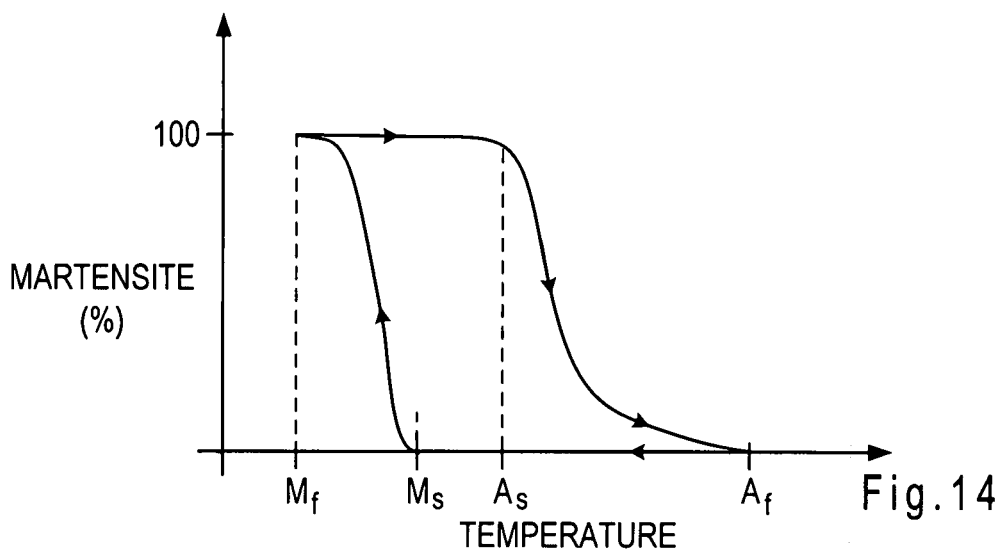
FIG. 14 is a transformation temperature curve for an exemplary shape memory alloy.

FIG. 14 shows a typical transformation temperature curve for an exemplary nickel-titanium shape memory alloy, where the y-axis represents the amount of martensite in the alloy and the x-axis represents temperature. At or above a temperature of $A_f$, the nickel-titanium alloy has a fully austenitic structure. Following the arrows, the alloy may be cooled to a temperature of $M_s$, at which point the transformation to the martensitic phase begins. Further cooling leads to an increase in the percentage of martensite in the material, ultimately leading to a fully martensitic structure at a temperature of $M_f$, as shown in FIG. 14.

Figure 15:
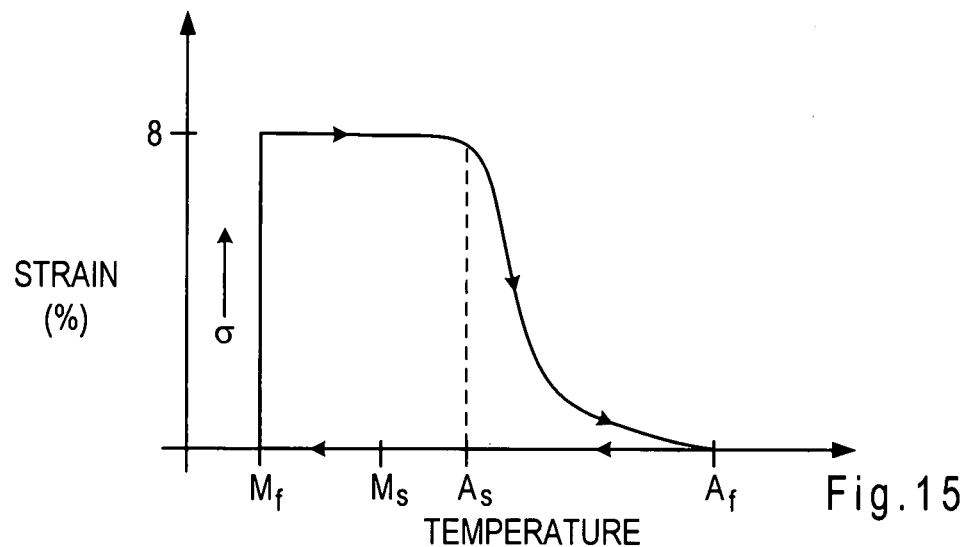
FIG. 15 is a diagram of strain versus temperature for an exemplary shape memory alloy.

Now referring also to FIG. 15, which shows strain versus temperature for an exemplary nickel-titanium shape memory alloy, the fully martensitic structure attained at a temperature of $M_f$ may be strained from a first configuration to a second configuration (as shown by the stress symbol $\sigma$). The alloy may accommodate several percent recoverable strain (8% in this example). To reverse the phase transformation and recover the strain, the temperature of the alloy is increased. Again following the arrows, the nickel-titanium alloy may be warmed to a temperature of $A_s$, at which point the alloy begins to transform to the austenitic phase. Upon further heating, the transformation to austenite progresses and the alloy gradually recovers the first configuration. Ultimately, at a temperature of $A_f$ or higher, the material has completed the return transformation to the austenitic phase (0% martensite) and has fully recovered the 8% strain.

According to one embodiment, the nickel-titanium alloy may include an intermediate temperature R-phase in addition to the higher temperature austenitic phase and the lower temperature martensitic phase. In other words, the R-phase may appear prior to martensite upon cooling from austenite. Similarly, the R-phase may appear prior to austenite upon heating from martensite. Whether or not the nickel-titanium alloy includes the R-phase depends on the composition and processing history of the alloy.

For the purposes of this disclosure, a nickel-titanium alloy that provides a substantial amount of recoverable strain (i.e., an elastic strain of at least about 0.5%) upon the removal of a deforming stress may be referred to as a superelastic alloy, whether or not the behavior is driven by phase transformations between martensite and austenite. For example, a recoverable strain of about 0.75% may be obtained by stress- and/or temperature-induced phase transformations between austenite and the R-phase (*Using Nitinol Alloys*, Johnson Mathey, San Jose, Calif. (2004) p. 17). It is also known that cold-worked martensitic nickel-titanium alloys can provide a recoverable strain of several percent (e.g., 3-4%) without a phase transformation to austenite (Duerig, T. W. et al., Linear Superelasticity in Cold-Worked Ni—Ti, *Engineering Aspects of Shape Memory Alloys*, Butterworth-Heinemann Ltd., London (1990) pp. 414-419). Preferably, the nickel-titanium alloy of the present disclosure provides a recoverable strain in the range of from about 0.5% to about 10%. More preferably, the recoverable strain is in the range of from about 2% to about 10%. Even more preferably, the recoverable strain is in the range of from about 3% to about 10%. Most preferably, the recoverable strain is in the range of from about 5% to about 10%.

Preferably, the medical device includes at least one component comprising the nickel-titanium alloy described herein. The component may be formed in whole or in part of the nickel-titanium alloy from wire, tubing, ribbon, button, bar, disk, sheet, foil, or another cast or worked shape. According to one embodiment, the component has a composite structure in which one or more portions of the structure are formed of the Ni—Ti-RE alloy, and one or more portions of the structure are formed of a different material. For example, the component may include distinct constituents, such as layers, cladding, filaments, strands, cables, particles, fibers, and/or phases, where one or more of the constituents are formed from the Ni—Ti-RE alloy, and one or more are formed from the different material. The different material may be a near-equiatomic binary nickel-titanium alloy, according to one embodiment, or a material including one or more elements selected from the group consisting of: Al, Cr, Mn, Fe, Co, Cu, Zn, Ga, Ge, Tc, Cd, In, Sn, Sb, Hg, Tl, Pb, Bi, Po, V, Ir, Pt, Au, Re, W, Pd, Rh, Ta, Ag, Ru, Hf, Os, Zr, Nb, and Mo. Such a composite structure may provide a component having improved radiopacity and optimized superelastic and/or mechanical properties compared to a monolithic component.

Figure 16:
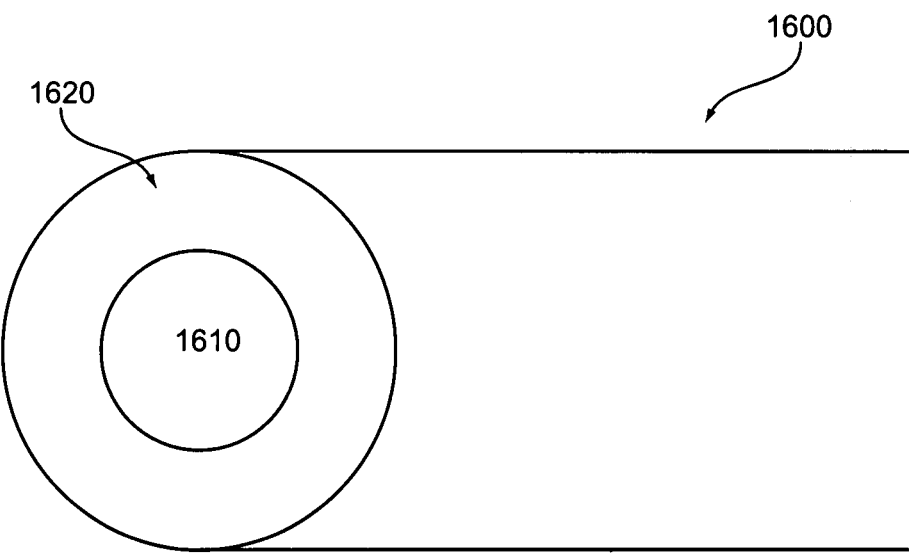
FIG. 16 is a schematic of an exemplary wire having a composite structure including at least one layer formed of a Ni—Ti-RE alloy.

The component including the nickel-titanium alloy described herein may include at least one wire. The wire may have a composite structure including, for example, a core layer and one or more outer layers disposed about the core layer. Preferably, one or more of the layers are formed of the Ni—Ti-RE alloy. One or more of the layers may be formed of a different material. The different material may be a binary nickel-titanium alloy or a material including one or more of the elements mentioned above. According to the embodiment shown in FIG. 16, the wire 1600 may include a core layer 1610 made of the Ni—Ti-RE alloy and an outer layer 1620 made of a near-equiatomic binary nickel-titanium alloy. Alternatively, the core layer 1610 may be made of the near-equiatomic binary nickel-titanium alloy and the outer layer 1620 may be made of the Ni—Ti-RE alloy. The wire 1600 may be formed by, for example, drawing or extruding a performs including multiple coaxial layers to form the composite structure. Alternatively, the wire 1600 may be formed by coating one or more layers on a core layer by plating or another deposition technique.

Figures 17A, 17B:
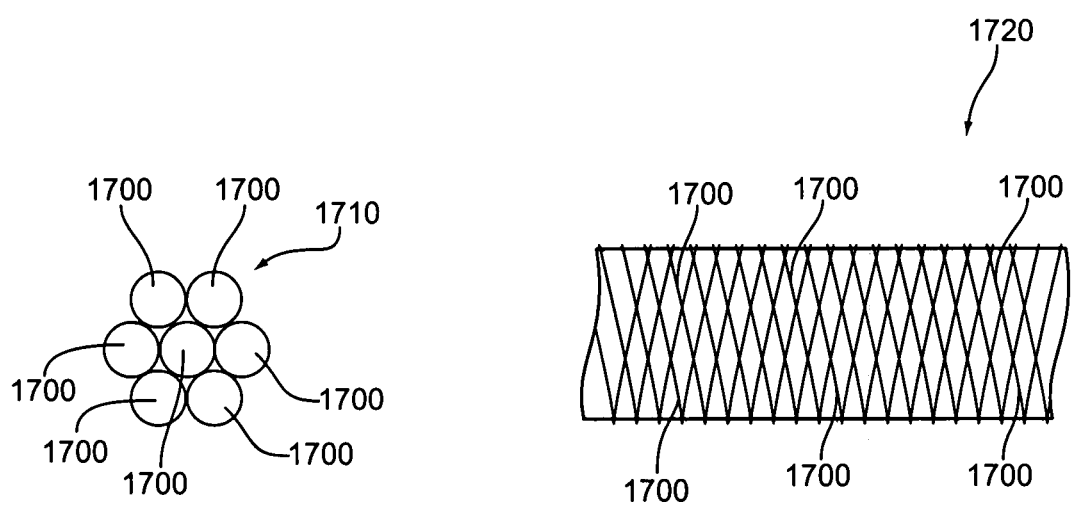
FIG. 17A is a cross-sectional schematic of an exemplary cable formed from seven wire strands, where one or more of the strands are formed of a Ni—Ti-RE alloy.
FIG. 17B is a side view schematic of an exemplary braided wire structure, where one or more strands of the wire structure are formed of a Ni—Ti-RE alloy.

The component may include two, three, four, five, six, or more wires, according to one embodiment, where each wire is made in whole or in part of the nickel-titanium alloy of the present disclosure. It is also contemplated that one or more of the wires may be made in whole or in part of a different material, such as a near-equiatomic binary nickel-titanium alloy or a radiopaque metal. Referring to FIGS. 17A and 17B, for example, the component may include a plurality of wire strands 1700 in a twisted configuration 1710 (e.g., a cable) or a plurality of wire strands 1700 in a braided configuration 1720, where one or more of the strands are made of the Ni—Ti-RE alloy and one or more of the strands are made of a near-equiatomic binary nickel-titanium alloy.

Figure 18:
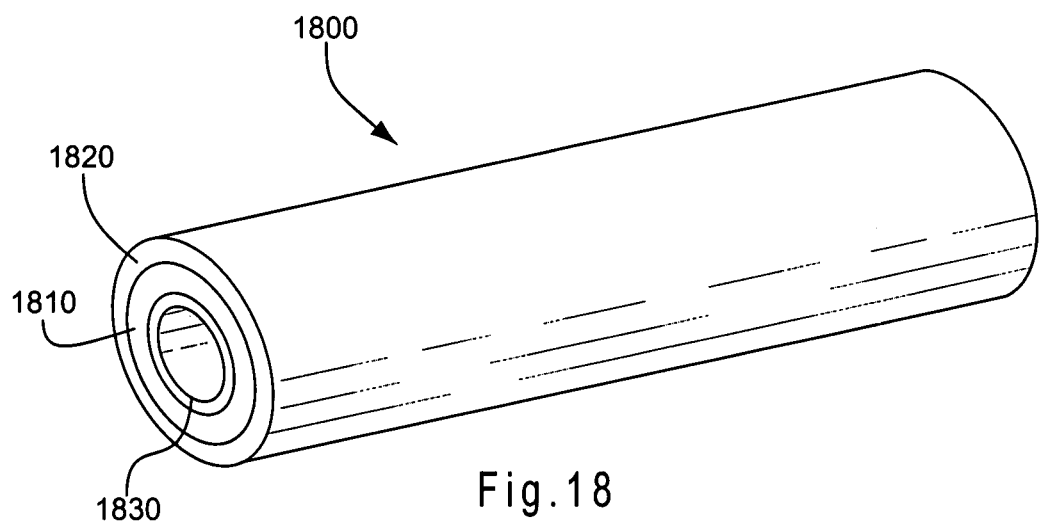
FIG. 18 is a schematic of an exemplary cannula having a composite structure, where one or more layers of the cannula are formed of a Ni—Ti-RE alloy.

According to another embodiment, the component comprises a tube or "cannula," to use terminology common in the medical device community. The cannula may have a composite structure. According to one embodiment, the cannula may be formed from a multilayered tube. Referring for example to FIG. 18, the cannula 1800 may include one or more coaxial layers 1810 of Ni—Ti-RE and one or more coaxial layers 1820, 1830 of another material, such as a binary nickel-titanium alloy or a radiopaque metal. The multilayered tube may be formed by drawing or extruding coaxial tubing. Alternatively, the multilayered tube may be prepared from a clad sheet that has been formed into a tube.

According to another embodiment, the component comprises another cast or worked shape, such as a ribbon, button, bar, rivet, sphere, disk, sheet, or foil.

The above described components may be employed individually or in combination as part of an insertable or implantable medical device, such as, for example, a stent, a stent graft, a wire guide, a radiopaque marker or marker band, a torqueable catheter, an introducer sheath, an orthodontic arch wire, or a manipulation, retrieval, or occlusive device such as a grasper, a snare, a basket (e.g., stone extraction or manipulation basket), a vascular plug, or an embolic protection filter.

Figure 19:
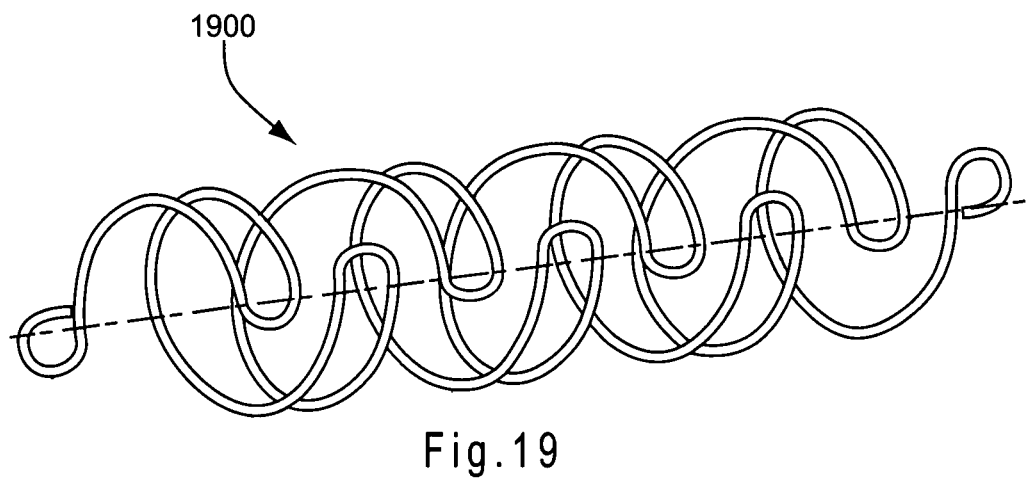
FIG. 19 is a schematic of an exemplary stent formed from one or more wires, where all or a portion of the wires is formed of a Ni—Ti-RE alloy.

According to one embodiment, the device is a stent. All or a portion of the stent may be made of the nickel-titanium alloy. The stent may further include a graft material attached thereto. Preferably, the stent is a self-expanding stent. However, balloon-expandable stents may also benefit from the Ni—Ti-RE alloy of the present disclosure. The stent may be formed from one or more wires or cut (e.g., laser cut) from a tube (cannula) using techniques known in the art. The cannula may have a composite structure as described above. According to another embodiment shown in FIG. 19, the stent 1900 may have a wire structure including one or more wires. A portion of the wire structure may be formed of Ni—Ti-RE and a portion of the wire structure may be formed of a different material, such as a binary nickel-titanium alloy. The one or more wires of such a stent may be formed as described above. The stent may further include a therapeutic surface coating comprising a drug such as, for example, paclitaxel. The therapeutic surface coating may help to prevent, for example, re-stenosis and the build-up of minerals at the treatment site.

According to another embodiment, the device is a radiopaque marker or marker band ("marker") that provides high x-ray contrast. Such a radiopaque marker may be more readily bonded to a nickel-titanium medical device than radiopaque markers formed of other materials (e.g., Pt or Au) due to the similarity between Ni—Ti-RE and binary nickel-titanium. In addition, Ni—Ti-RE radiopaque markers may better resist galvanic corrosion than other materials when used with nickel-titanium based devices. According to one embodiment, the superelastic properties of a Ni—Ti-RE radiopaque marker may aid in attaching the marker to a catheter, stent, wire guide or other medical device. The marker may be designed to fully expand or contract at or above a temperature corresponding to $A_f$ of the Ni—Ti-RE alloy to facilitate the securing of the marker to the device. For example, a Ni—Ti-RE marker band may shrink to fit around a catheter, or a Ni—Ti-RE marker may expand to fit securely within an eyelet of a stent. Ni—Ti-RE radiopaque markers may be formed by mechanical working techniques known in the art, such as swaging, and marker bands may be cut from thin-walled Ni—Ti-RE tubes.

A method of imaging a medical device within a patient according to the present disclosure includes delivering a medical device having at least one component made from a nickel-titanium alloy including from about 34 at. % to about 60 at. % nickel, from about 34 at. % to about 60 at. % titanium, and from about 0.1 at. % to about 15 at. % at least one rare earth element to a site in a patient. The rare earth element is selected from the group consisting of La, Pr, Nd, Pm, Sm, Eu, Gd, Tb, Dy, Ho, Er, Tm, Yb, Lu, Ac, Th, Pa, and U.

The patient is then preferably exposed to radiation having an energy in the range of from 15 keV to 125 keV to image the medical device. More preferably, the energy is in the range of from 15 keV to 80 keV for imaging. Even more preferably, the energy is in the range of from 15 keV to 70 keV, or from 15 keV to 60 keV, for imaging. It is also preferred that the radiation has a peak intensity at an energy in the range of from 30 keV to 60 keV. More preferably, the radiation has a peak intensity at an energy in the range of from 35 keV to 55 keV. Even more preferably, the radiation has a peak intensity at an energy in the range of from 40 keV to 50 keV.

To expose the patient to the radiation, the patient may be situated in opposition to an x-ray source with at least one filter disposed between the x-ray source and the patient. The filter may be an aluminum filter (e.g., a 2.5 mm aluminum filter) and/or a copper filter (e.g., a 0.1 mm copper filter, 0.2 mm copper filter, or a 0.3 mm copper filter), for example. The x-ray source preferably operates at a voltage ("tube voltage") in the range of from 60 kVp to 150 kVp.

A method of using a medical device according to the present disclosure includes providing a medical device including at least one component comprising the nickel-titanium alloy. The medical device (e.g., a stent, stent graft, retrieval device, or an embolic protection filter) may be loaded into a delivery system, according to one aspect of the method. The medical device may then be inserted into a patient and then delivered to a treatment site in the patient. When positioned at the treatment site, the device may be deployed. The superelastic and/or the shape memory effect may be used to deliver and deploy the medical device.

According to a preferred embodiment in which the superelastic effect is utilized for delivery and deployment, the device may be maintained in a delivery configuration by a constraining member. For example, a self-expandable stent is typically maintained at a compressed diameter for delivery within a vessel by a tubular delivery sheath which overlies the stent. When the constraining member (e.g., the delivery sheath) is removed and the stress is released, the martensite transforms to austenite and the medical device may reach (recover) its deployed configuration. For example, the self-expandable stent may expand from the compressed diameter to an expanded diameter and come into contact with the vessel wall. The radiopacity of the alloy aids in positioning the device in the desired location in the body passageway during delivery and deployment.

According to this embodiment, the nickel-titanium alloy has an austenite finish temperature ($A_f$) which is less than or equal to human body temperature (37° C.) so that removal of the constraining member is sufficient to trigger the transformation to the austenitic phase. Preferably, the $A_f$ may be in the range of from about −15° C. to about 37° C. Even more preferably, the $A_f$ may be in the range of from about −15° C. to about 20° C. An austenite start temperature ($A_s$) of the nickel-titanium alloy is preferably in the range of from about −25° C. to about 20° C., according to one embodiment.

Alternatively, the shape memory effect may be utilized to deliver and deploy the medical device comprising the nickel-titanium alloy. In other words, a change in temperature instead of an applied (removed) stress may control the transformation from martensite to austenite. For example, the stent of the previous example may be deployed by heating instead of retraction of a delivery sheath. According to this embodiment, the nickel-titanium alloy has an austenite finish temperature ($A_f$) which is less than or equal to body temperature (37° C.). The medical device is maintained at a temperature of less than $A_f$, and preferably less than $A_s$, prior to and during delivery of the device into the body, thereby maintaining a martensitic structure of the nickel-titanium alloy. The device transforms to the austenitic structure and thus deploys when warmed up to about body temperature. Cooling of the device during delivery is desirable to prevent the martensitic structure from prematurely transforming to austenite. As the device is being advanced in the body, the cooling may entail keeping the device at a temperature below $A_s$ by, for example, flushing a cold fluid through the device or through a delivery system of the device. Preferably, the nickel-titanium alloy has a value of $A_f$ of at least about 27° C., although an $A_f$ of less than about 27° C. is also possible. Even more preferably, the nickel-titanium alloy has a value of $A_f$ of at least about 32° C. It is also preferred that $A_f$ is no higher than about 37° C.

In another example utilizing the shape memory effect, the $A_f$ of the nickel-titanium alloy is greater than body temperature (37° C.) but below a temperature that may be damaging to nearby tissue. Preferably, the $A_f$ is at least about 38° C. It is also preferred that the $A_f$ is no higher than about 58° C. More preferably, the $A_f$ is no higher than about 50° C. According to this embodiment, the medical device is advanced through the body to the treatment site without the need for cooling or a constraining member to maintain a martensitic structure. When the device is in place at the treatment site, the device is warmed up to a temperature of $A_f$ or higher to transform the martensite to austenite, and the device deploys to the deployed configuration. The heating may entail, for example, flushing a warm fluid through the medical device or the delivery system for the device. Once the deployed configuration has been obtained, the heating is halted and the device remains in the body passageway in the deployed configuration. To maintain the austenitic structure of the nickel-titanium alloy while the medical device is in place within the passageway, the nickel-titanium alloy may be chosen such that $M_f$, and preferably $M_s$, are below body temperature. Since austenite is stronger than martensite, it is preferable to retain the austenitic phase of the nickel-titanium alloy when the medical device is deployed. If the martensitic finish temperature ($M_f$) and the martensitic start temperature ($M_s$) are not below body temperature, it may be necessary to continuously heat the device during deployment to prevent an unwanted phase transformation to martensite.

The transformation temperatures of the present nickel-titanium alloys may be adjusted as desired by controlling the composition and processing of the alloys. The transformation temperatures are sensitive to small changes in the ratio of nickel to titanium and to the presence of rare earth or other alloying elements. For example, the $A_f$ of stoichiometric NiTi alloys—those having exactly a one-to-one proportion of nickel atoms to titanium atoms—is generally above 100° C., while the $A_f$ of a slightly off-stoichiometric alloy including an excess of nickel (e.g., from about 50.6 to about 50.8 at. % Ni) is generally around 0° C. Increasing the proportion of nickel to titanium in the alloy, therefore, provides a means of reducing the $A_f$ to the desired level.

The presence of rare earth or other alloying elements also can provide an increase or decrease in the transformation temperatures or alter the magnitude of the temperature hysteresis. By selecting the appropriate concentration, type, and/or combination of rare earth alloying elements, $A_f$ and the other transformation temperatures can be fine-tuned to within the desired temperature range. Furthermore, one or more additional alloying elements can be included in combination with the one or more rare earth alloying elements to obtain the desired transformation temperatures. For example, additions of chromium, palladium, cobalt and/or iron may be effective in reducing $A_f$. Additions of vanadium and/or cobalt may be effective in reducing $M_s$. Copper is useful for eliminating the R-phase.

In practice, differential scanning calorimetry (DSC) techniques known in the art may be used to determine the phase transformation temperatures of the phases present in the nickel-titanium alloys. DSC measurements may be carried out according to the American Society for Testing and Materials (ASTM) standard F2004-05 entitled "Standard Test Method for Transformation Temperature of Nickel-Titanium Alloys by Thermal Analysis," which is hereby incorporated by reference. Alternatively, methods known as constant load dilatometry and bend and free recovery may be employed to determine the transformation temperatures. Bend and free recovery tests may be carried out in accordance with the ASTM standard F2082-03 entitled "Standard Test Method for Determination of Transformation Temperature of Nickel-Titanium Shape Memory Alloys by Bend and Free Recovery," which is hereby incorporated by reference. Electrical resistivity measurements are also known in the art for determining the phase transformation temperatures of metals and alloys. Such measurements may be carried out by heating and cooling the alloy of interest while recording voltage using a four-probe constant current technique, for example. Using electrical resisitivity measurements, it is possible to characterize phase transformations occurring in the nickel-titanium alloy as a function of applied stress as well as temperature.

According to a preferred embodiment, the nickel-titanium alloy is biocompatible. When introduced into a patient, a biocompatible material or device will not cause an adverse reaction or response in a majority of the patients. The biocompatibility of the nickel-titanium alloy may be assessed according to American Society for Testing and Materials (ASTM) standards F748-04 entitled "Standard Practice for Selecting Generic Biological Test Methods for Materials and Devices," F813-01 entitled "Standard Practice for Direct Contact Cell Culture Evaluation of Materials for Medical Devices," and/or F895-84 entitled "Standard Test Method for Agar Diffusion Cell Culture Screening for Cytotoxicity." Additionally, the International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing" may be useful in evaluating the biocompatibility of the nickel-titanium alloy and/or a medical device comprising the alloy. The aforementioned standards set forth practices and methods designed for evaluating cytotoxicity, infectivity, pyrogenicity, irritation potential, reactivity, hemolytic activity, carcinogenicity and/or immunogenicity, and are hereby incorporated by reference. Since biocompatibility is a function of the type of bodily tissue contact and the duration of contact, the amount of testing required generally depends on the application. For example, the biocompatibility testing requirements for a short term contacting basket are substantially different from those of a permanently implanted stent.

To produce the nickel-titanium alloys of the present disclosure and medical devices comprising the alloys, a melt including the desired amounts of alloying elements is formed and then cooled into a solid (e.g., an ingot). For example, from about 34 at. % to about 60 at. % nickel, from about 34 at. % to about 60 at. % titanium, and from about 0.1 at. % to about 15 at. % at least one rare earth element may be added to the melt. Up to about 14.9 at. % additional alloy elements may also be included in the melt. High purity raw materials (e.g., Ti>99.7 wt. % purity and Ni>99.99 wt. % purity) are preferably melted in an inert gas or vacuum atmosphere.

Melting methods known in the art, including but not limited to vacuum induction melting (VIM), vacuum consumable arc melting (VAR), and electron beam melting, may be employed to form the melt. Remelting is generally desirable to obtain satisfactory microstructural homogeneity in the ingot. For example, successive VAR processes or a VIM/VAR double melting process may be employed.

The ingot may then be hot worked into a first shape (e.g., bar, rod, tube hollow, or plate) by, for example, extruding, hot rolling, or forging. Hot working is generally employed to refine the cast structure of the ingot and to improve mechanical properties. The hot working is generally carried out at temperatures in the range of from about 700° C. to about 950° C., and may require multiple hot working and reheating cycles. The reheating may be carried out over an eight hour period, for example. Preferably, the ingot undergoes a minimum deformation of about 90% during hot working in order to homogenize the as-cast, dendritic microstructure. Prior to hot working, it may be beneficial to carry out a solution heat treatment that involves soaking the ingot at an elevated temperature for a given time duration, followed by quenching. The solution heat treatment may aid in homogenizing the microstructure of the alloy and may be carried out at a temperature in the range of from about 850° C. to about 1150° C., for example. Preferably, the solution heat treatment is carried out at a temperature in the range of from about 1000° C. to about 1150° C.

The first shape (e.g., bar, rod, tube, or plate) may then be cold worked into a component by cold drawing or cold rolling, for example. The cold working typically involves several passes in combination with interpass annealing treatments at temperatures in the range of from about 600° C. to about 800° C. The interpass annealing treatments soften the material through recrystallization and growth of the austenite grains between cold work passes, where 30-40% deformation is typically imparted. If cold drawing is employed to form a wire, for example, a polycrystalline diamond die with a molybdenum disulphide or other suitable lubricant may be employed in order to reduce the drawing stress.

Machining operations, such as, for example, drilling, cylindrical centerless grinding, or laser cutting may also be employed to fabricate the component. Other operations, such as wire braiding or winding, may also be carried out.

A heat treatment is employed to impart a "memory" of a desired final shape and to optimize the shape memory/superelastic and mechanical properties of the component. The number, duration and the temperature of the heat treatments may alter the transformation temperatures. Typically, heat treatment temperatures of 350° C. to 550° C. are appropriate to set the final shape and optimize the shape memory/superelastic and mechanical properties. Preferably, the heat treating involves annealing the component while constrained in a final shape at a temperature in the range of from about 350° C. to about 550° C. More preferably, heat treatment or annealing temperatures in the range of from 450° C. to 550° C. are appropriate. In alloys having an excess of nickel atoms (e.g., from about 50.6 to about 50.8 at. % Ni), for example, the heat treatments described above may cause nickel-rich precipitates to form, thereby reducing the nickel content of the matrix and causing the transformation temperatures to increase. The precipitates may also improve the tensile strength of the nickel-titanium alloy. Precipitation of these nickel-rich particles may be desirable so as to obtain a thermoelastic martensitic phase transformation from austenite.

According to a preferred embodiment, the nickel-titanium alloys of the present disclosure have an ultimate tensile strength of at least about 1350 MPa. As is generally known to those of skill in the art, the ultimate tensile strength (or tensile strength) of a material corresponds to the maximum engineering stress that can be sustained by the material in tension without fracture. Engineering stress is defined as $$\frac{F}{A_0},$$

where F represents tensile force and $A_0$ represents the original cross-sectional area of the specimen prior to application of the force. Tensile testing of the alloys is preferably carried out in accordance with American Society of Testing and Materials (ASTM) standards F2063, "Standard Specification for Wrought Nickel-Titanium Shape Memory Alloys for Medical Devices and Surgical Implants" and/or F2516 "Standard Test Method for Tension Testing of Nickel-Titanium Superelastic Materials," which are hereby incorporated by reference.

In the case of nickel-titanium alloys in which a two-way shape memory effect is desired, additional "training" at lower temperatures may be carried out to set a second shape.

EXAMPLE 1

Ingots of several rare-earth doped nickel-titanium alloys were produced using vacuum induction melting (VIM). Specifically, Ni—Ti—Er, Ni—Ti—La, Ni—Ti—Gd, and Ni—Ti—Nd, each containing 7.5 at. % rare earth element, were melted. A Ni—Ti-7.5 at. % Pt ingot and a binary nickel-titanium alloy were also produced by VIM for comparison. The ingots of 2.25 inches in diameter and 3 inches in height were rolled to form plates. Each of the Ni—Ti—X plates showed some interdendritic cracking as a consequence of rolling, although the Er-doped nickel-titanium alloy seemed to withstand rolling the best. The rolled plates were soaked for 24 hours at 850° C. and then hot worked to a size of slightly greater than 1 inch (2.54 cm) in height. The composition of each specimen is given in weight percent in Table 5. The concentration of carbon, oxygen, and nitrogen impurities is also shown in parts per million (ppm).

TABLE 5

Composition Data for Ni—Ti and Ni—Ti—X (X = Er, La, Gd, Nd, or Pt) Specimens

| Sample | Carbon (ppm) | Oxygen (ppm) | Nitrogen (ppm) | Ni | Ti (wt. %) | RE or Pt (wt. %) |
|---|---|---|---|---|---|---|
| Ni—Ti—Er | 1320 | 236 | 60 | Balance | 32.04 | 20.12 |
| Ni—Ti—La | 760 | 307 | 8 | Balance | 33.17 | 17.30 |
| Ni—Ti—La | 33 | 2130 | 23 | Balance | 33.17 | 17.30 |
| Ni—Ti—Gd | 380 | 149 | 6 | Balance | 32.43 | 19.15 |
| Ni—Ti—Nd | 140 | 124 | 4 | Balance | 32.95 | 17.85 |
| Ni—Ti—Pt | 720 | 270 | 12 | Balance | 31.00 | 22.71 |
| Ni—Ti | 980 | 254 | 15 | Balance | Wash chemistry | — |

Prior to rolling, the surfaces of the as-cast specimens were polished to prepare the samples for conventional Brinell hardness tests. Such tests involve pressing a spherical indenter of a specified diameter under a known load into the surface of the specimen, and measuring the diameter (d) of the indentation after the test. A Brinell hardness number (BHN) may then be obtained by dividing the load used, in kilograms, by the actual surface area of the indentation, in square millimeters. Brinell hardness numbers obtained from hardness tests on polished, as-cast specimens are presented in Table 6 below. A steel ball of 1.68 mm in diameter was pushed into the surface of each specimen with a 30 kg force for a dwell time of 10 seconds. Four indentations were made for each sample, with two measurements of diameter ($d_1$, $d_2$) for each indentation. Higher average BHN numbers are obtained from specimens exhibiting greater resistance to plastic deformation (i.e., showing increased hardness), and lower average BHN numbers are obtained from softer specimens. As indicated in Table 6, the Ni—Ti-RE specimens exhibited lower hardnesses than did the binary Ni—Ti specimen. The Ni—Ti—Pt sample exhibited a higher hardness than did the binary Ni—Ti specimen.

TABLE 6

Brinell Hardness Data for As-Cast, Polished Specimens

| Alloy | $d_1$ | $d_2$ | BHN | Average BHN |
|---|---|---|---|---|
| Ni—Ti—Gd | 0.4096 | 0.4274 | 317.4 | 304 |
| | 0.437 | 0.4373 | 291 | |
| | 0.4266 | 0.4467 | 291 | |
| | 0.4153 | 0.4244 | 315 | |
| Ni—Ti—Nd | 0.4816 | 0.5093 | 226.5 | 247 |
| | 0.4531 | 0.4579 | 268.1 | |
| | 0.4614 | 0.4676 | 257.8 | |
| | 0.4919 | 0.4858 | 235.7 | |
| Ni—Ti—Pt | 0.3679 | 0.3522 | 429 | 460 |
| | 0.3735 | 0.3618 | 411.4 | |
| | 0.3447 | 0.3023 | 531.5 | |
| | 0.3535 | 0.3349 | 469.5 | |
| Ni—Ti—Er | 0.4266 | 0.4289 | 303.9 | 294 |
| | 0.4254 | 0.4207 | 311.5 | |
| | 0.4582 | 0.4466 | 271.8 | |
| | 0.4355 | 0.4405 | 289.9 | |
| Ni—Ti | 0.4395 | 0.4386 | 288.5 | 311 |
| | 0.4265 | 0.4315 | 302.2 | |
| | 0.4188 | 0.3953 | 335.6 | |
| | 0.4159 | 0.4203 | 318 | |

The microstructures of the hot worked specimens were investigated using a scanning electron microscope (SEM) equipped with an energy dispersive x-ray spectrometer (EDS). The SEM allowed regions of the alloys to be viewed at high magnifications and the EDS provided localized chemical information. Used together, the tools showed that the rare earth elements tended to segregate to the grain boundaries of the Ni—Ti-RE specimens. The alloy microstructure showed a dendritic form and included oxide and carbide precipitates. It is believed that compositional nonuniformity may inhibit shape memory phase transformations near human body temperature. Indeed, DSC experiments conducted by heating and cooling the specimens over temperatures ranging from −150° C. to 80° C. revealed no phase transformations. Accordingly, the inventors believe that a homogenization heat treatment at a temperature in excess of 850° C. (e.g., 1000° C. to 1150° C.) and for a longer time duration (e.g., 2-3 days) may be advantageous for improving the compositional homogeneity of the Ni—Ti-RE ingots and obtaining a suitable phase structure for shape memory behavior around body temperature.

Experiments to compare the x-ray contrast of two of the Ni—Ti-RE alloys and Ni—Ti—Pt with the x-ray contrast of a binary Nitinol alloy were conducted using a Picker Clinix RF fluoroscope and a phantom developed by the Center for Devices and Radiological Heath (CDRH) of the U.S. Food and Drug Administration (FDA). The phantom was used to simulate x-ray attenuation through the lower abdomen of a typical adult. In particular, the phantom was designed to represent the upper gastrointestinal tract of a 5'8" adult weighing about 165 lbs with a posterior-anterior thickness of 23 cm. The dimensions of the phantom, which is composed primarily of polymethyl methacrylate (PMMA) and aluminum, are given in FIG. 20.

The three ternary nickel-titanium alloy specimens used in the radiopacity experiments included, respectively, 7.5 at. % Er, 7.5 at. % Gd, and 7.5 at. % Pt. The experiments were carried out using the CDRH phantom in fluoroscopic mode and static mode. The intensity of the radiation transmitted through each specimen and the background intensity were measured at various tube voltages. Values of x-ray contrast were obtained by subtracting the radiation transmitted through the specimen from the background intensity at each voltage. The x-ray contrast values were then normalized by the x-ray contrast obtained for the binary Ni—Ti sample to obtain relative x-ray contrast values for each specimen, as shown in Tables 7 and 8.

Figure 21:
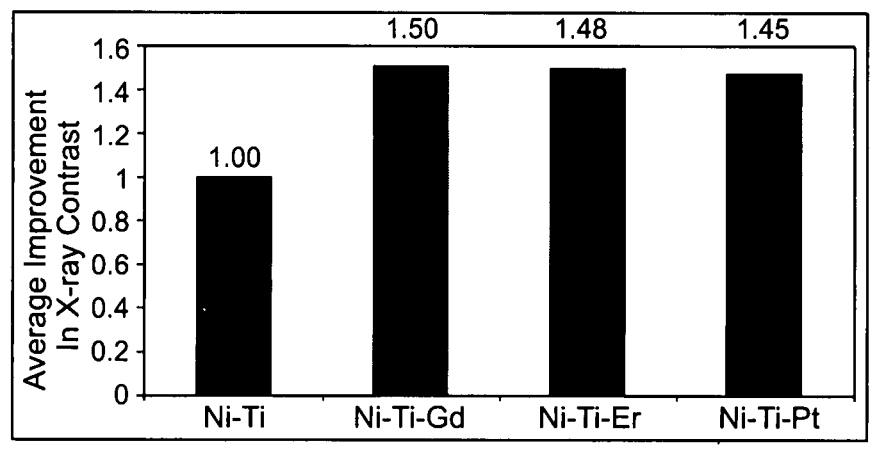
FIG. 21 is a bar graph showing the average improvement in x-ray contrast for Ni—Ti—X specimens (X=Gd, Er or Pt) relative to binary Ni—Ti as determined using the CDRH phantom at various tube voltages in fluoroscopic mode.

As indicated by the x-ray contrast data, each ternary alloy showed an improvement in radiopacity relative to the binary Nitinol alloy. Table 7 shows the relative x-ray contrast values of the alloys as determined using the CDRH phantom at various voltages in fluoroscopic mode, and FIG. 21 shows the average value of relative x-ray contrast for each alloy over the range of voltages used. Overall, the Ni—Ti—Gd alloy exhibited the highest x-ray contrast, with an average relative x-ray contrast of 1.50 for the voltage range of 40-110 kV. The Ni—Ti—Er alloy showed an average relative x-ray contrast of 1.48 for the same voltage range, while the Ni—Ti—Pt alloy exhibited an average relative x-ray contrast of 1.45.

TABLE 7

Values of Relative X-Ray Contrast (Fluoroscopic Mode)

| Specimen | | 40 kV | 50 kV | 60 kV | 70 kV | 80 kV | 90 kV | 100 kV | 110 kV | Avg. |
|---|---|---|---|---|---|---|---|---|---|---|
| Ni—Ti | x-ray contrast | 293 | 301 | 372 | 370 | 300 | 370 | 295 | 333 | 329.3 |
| | relative value | 1.00 | 1.00 | 1.00 | 1.00 | 1.00 | 1.00 | 1.00 | 1.00 | 1.00 |
| Ni—Ti—Gd | x-ray contrast | 532 | 464 | 477 | 495 | 492 | 484 | 490 | 525 | 494.9 |
| | relative value | 1.82 | 1.54 | 1.28 | 1.34 | 1.64 | 1.31 | 1.66 | 1.58 | 1.50 |
| Ni—Ti—Er | x-ray contrast | 546 | 492 | 488 | 488 | 377 | 523 | 500 | 490 | 488.0 |
| | relative value | 1.86 | 1.63 | 1.31 | 1.32 | 1.26 | 1.41 | 1.69 | 1.47 | 1.48 |
| Ni—Ti—Pt | x-ray contrast | 482 | 435 | 480 | 560 | 499 | 453 | 490 | 422 | 477.6 |
| | relative value | 1.64 | 1.45 | 1.29 | 1.51 | 1.66 | 1.22 | 1.66 | 1.27 | 1.45 |

Figure 22:
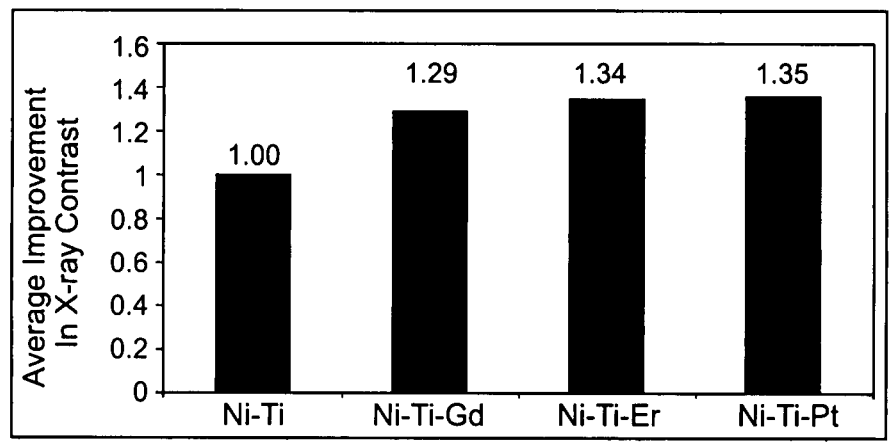
FIG. 22 is a bar graph showing the average improvement in x-ray contrast for Ni—Ti—X specimens (X=Gd, Er or Pt) relative to binary Ni—Ti as determined using the CDRH phantom at various tube voltages in static mode.

Table 8 shows the relative x-ray contrast values of the alloys as determined using the CDRH phantom at several voltages in static mode, and FIG. 22 shows the average value of relative x-ray contrast for each alloy over the range of voltages used. Overall, the Ni—Ti—Pt alloy exhibited the highest x-ray contrast under these conditions, with an average relative x-ray contrast of 1.35 for the voltage range of 60-100 kV. The Ni—Ti—Er alloy showed an average relative x-ray contrast of 1.34 for the same voltage range, while the Ni—Ti—Gd alloy exhibited an average x-ray contrast of 1.29.

TABLE 8

Values of Relative X-Ray Contrast (Static Mode)

| Specimen | | 60 kV | 70 kV | 80 kV | 90 kV | 100 kV | Avg. |
|---|---|---|---|---|---|---|---|
| Ni—Ti | x-ray contrast | 540 | 490 | 437 | 399 | 380 | 449.2 |
| | relative value | 1.00 | 1.00 | 1.00 | 1.00 | 1.00 | 1.00 |
| Ni—Ti—Gd | x-ray contrast | 605 | 610 | 572 | 572 | 540 | 579.8 |
| | relative value | 1.12 | 1.24 | 1.31 | 1.43 | 1.42 | 1.29 |
| Ni—Ti—Er | x-ray contrast | 555 | 620 | 600 | 651 | 583 | 601.8 |
| | relative value | 1.03 | 1.27 | 1.37 | 1.63 | 1.53 | 1.34 |
| Ni—Ti—Pt | x-ray contrast | 644 | 662 | 570 | 580 | 571 | 605.4 |
| | relative value | 1.19 | 1.35 | 1.30 | 1.45 | 1.50 | 1.35 |

Preferably, the x-ray contrast of a Ni—Ti-RE alloy is in the range of from greater than 1 to about 2 times that of a near-equiatomic binary nickel-titanium alloy when the alloys are exposed to radiation having an energy in the range of from 40 keV to 110 keV. More preferably, the x-ray contrast of the Ni—Ti-RE alloy is in the range of from about 1.2 to about 1.9 times that of the near-equiatomic binary nickel-titanium alloy when the alloys are exposed to radiation having an energy in the range of from 40 keV to 110 keV.

EXAMPLE 2

Twelve additional alloys having the compositions given in Table 9 below are being melted. After melting and casting, the alloys may undergo a homogenization heat treatment at 1000° C. for 72 hours. The homogenized alloys may then be mechanically worked into specimens as described above.

TABLE 9

Composition Data for Ni—Ti—Er and Ni—Ti—Er—X
(X = Pd or Cr) Specimens

| | Ni (at. %) | Ti (at. %) | Er (at. %) | Pd (at. %) | Cr (at. %) |
|---|---|---|---|---|---|
| Series A | 51 | 45 | 4 | | |
| | 51 | 44 | 4 | 1 | |
| | 51 | 44 | 4 | | 1 |
| Series B | 52.5 | 43.5 | 4 | | |
| | 52.5 | 42.5 | 4 | 1 | |
| | 52.5 | 42.5 | 4 | | 1 |
| Series C | 55 | 41 | 4 | | |
| | 55 | 40 | 4 | 1 | |
| | 55 | 40 | 4 | | 1 |
| Series X | 47 | 49 | 4 | | |
| | 45 | 51 | 4 | | |
| | 43 | 53 | 4 | | |

A nickel-titanium alloy comprising nickel, titanium, and at least one rare earth element (RE) has been described. A medical device comprising at least one component including the nickel-titanium alloy has also been described. The radiopaque Ni—Ti-RE alloy has improved radiopacity compared to previous nickel-titanium alloys. Consequently, the medical device has better visibility during non-invasive imaging procedures, such as x-ray fluoroscopy. The nickel-titanium alloy preferably further has superelastic or shape memory properties that are advantageous for the medical device.

According to one embodiment, the nickel-titanium alloy comprises from about 39 at. % to about 55 at. % nickel; from about 39 at. % to about 55 at. % titanium; and from about 5 at. % to about 10 at. % at least one rare earth element preferably selected from the group consisting of La, Pr, Nd, Pm, Sm, Eu, Gd, Tb, Dy, Ho, Er, Tm, Yb, and Lu. The alloy further comprises one or more additional alloying elements at a concentration of up to about 9.9 at. %. Preferably, the one or more additional alloying elements are selected from the group consisting of Al, Cr, Mn, Fe, Co, Cu, Zn, Ga, Ge, Tc, Cd, In, Sn, Sb, Hg, Tl, Pb, Bi, Po, V, Ir, Pt, Au, Re, W, Pd, Rh, Ta, Ag, Ru, Hf, Os, Zr, Nb, and Mo. The additional alloying element preferably has a lower concentration in the alloy than the rare earth element when the one or more additional alloying elements are selected from the group consisting of Ir, Pt, Au, Re, W, Pd, Rh, Ta, Ag, Ru, Hf, Os, Zr, Nb, and Mo. It is also preferred that the radiopacity of the nickel-titanium alloy is from about 1.2 to about 5 times greater than that of the near-equiatomic binary nickel-titanium alloy when exposed to radiation having an energy in the range of from 15 keV to 150 keV. The radiation may have a peak intensity at an energy in the range of from 30 keV to 60 keV. The alloy is preferably biocompatible and superelastic with an austenite finish temperature in the range of from about −15° C. to about 37° C. It is also advantageous for the nickel-titanium alloy to have an ultimate tensile strength of at least about 1350 MPa.

According to another embodiment, the nickel-titanium alloy comprises from about 39 at. % to about 55 at. % nickel; from about 39 at. % to about 55 at. % titanium; and from about 2.5 at. % to about 7.5 at. % at least one rare earth element preferably selected from the group consisting of La, Pr, Nd, Pm, Sm, Eu, Gd, Tb, Dy, Ho, Er, Tm, Yb, and Lu. Preferably, the alloy further comprises one or more additional alloying elements at a concentration of up to about 9.9 at. %, wherein the one or more additional alloying elements are selected from the group consisting of Al, Cr, Mn, Fe, Co, Cu, Zn, Ga, Ge, Tc, Cd, In, Sn, Sb, Hg, Tl, Pb, Bi, Po, V, Ir, Pt, Au, Re, W, Pd, Rh, Ta, Ag, Ru, Hf, Os, Zr, Nb, and Mo. The additional alloying element preferably has a lower concentration in the alloy than the rare earth element when the one or more additional alloying elements are selected from the group consisting of Ir, Pt, Au, Re, W, Pd, Rh, Ta, Ag, Ru, Hf, Os, Zr, Nb, and Mo. It is also preferred that the radiopacity of the nickel-titanium alloy is from about 1.2 to about 5 times greater than that of the near-equiatomic binary nickel-titanium alloy when exposed to radiation having an energy in the range of from 15 keV to 150 keV. The radiation may have a peak intensity at an energy in the range of from 30 keV to 60 keV. The alloy is preferably biocompatible and superelastic with an austenite finish temperature in the range of from about −15° C. to about 37° C. It is also advantageous for the nickel-titanium alloy to have an ultimate tensile strength of at least about 1350 MPa.

According to another embodiment, the nickel-titanium alloy has a radiopacity and comprises from about 39 at. % to about 55 at. % nickel; from about 39 at. % to about 55 at. % titanium; and from about 5 at. % to about 10 at. % at least one rare earth element, whereby the nickel-titanium alloy has a radiopacity greater than that of a near-equiatomic binary nickel-titanium alloy. Preferably, the at least one rare earth element is selected from the group consisting of La, Pr, Nd, Pm, Sm, Eu, Gd, Tb, Dy, Ho, Er, Tm, Yb, and Lu. It is also preferred that the alloy further comprise one or more additional alloying elements at a concentration of up to about 9.9 at. %. Preferably, the one or more additional alloying elements are selected from the group consisting of Al, Cr, Mn, Fe, Co, Ni, Cu, Zn, Ga, Ge, Tc, Cd, In, Sn, Sb, Hg, Tl, Pb, Bi, Po, V, Ir, Pt, Au, Re, W, Pd, Rh, Ta, Ag, Ru, Hf, Os, Zr, Nb, and Mo. The one or more additional alloying elements preferably have a lower concentration in the alloy than the rare earth element when the one or more additional alloying elements are selected from the group consisting of Ir, Pt, Au, Re, W, Pd, Rh, Ta, Ag, Ru, Hf, Os, Zr, Nb, and Mo. It is advantageous for the nickel-titanium alloy to have a radiopacity in the range of from greater than about 1.2 to about 5 times that of the near-equiatomic binary nickel-titanium alloy when exposed to radiation having an energy in the range of from 15 keV to 150 keV. Preferably, the radiation has a peak intensity at an energy in the range of from 30 keV to 60 keV. It is also preferred that the nickel-titanium alloy has a lower temperature phase and a higher temperature phase, wherein strain introduced in the nickel-titanium alloy in the lower temperature phase is recovered upon a phase transformation to the higher temperature phase. The lower temperature phase is preferably martensite and the higher temperature phase is preferably austenite. It is also preferred that the alloy has an austenite finish temperature in the range of from about −15° C. to about 37° C., and the alloy may further include an intermediate temperature R-phase. Preferably, the nickel-titanium alloy has an ultimate tensile strength of at least about 1350 MPa and is biocompatible.

According to another embodiment, the nickel-titanium alloy has a radiopacity and comprises from about 39 at. % to about 55 at. % nickel; from about 39 at. % to about 55 at. % titanium; and from about 2.5 at. % to about 7.5 at. % at least one rare earth element, whereby the nickel-titanium alloy has a radiopacity greater than that of a near-equiatomic binary nickel-titanium alloy. Preferably, the at least one rare earth element is selected from the group consisting of La, Pr, Nd, Pm, Sm, Eu, Gd, Tb, Dy, Ho, Er, Tm, Yb, and Lu. It is also preferred that the alloy further comprise one or more additional alloying elements at a concentration of up to about 9.9 at. %. Preferably, the one or more additional alloying elements are selected from the group consisting of Al, Cr, Mn, Fe, Co, Ni, Cu, Zn, Ga, Ge, Tc, Cd, In, Sn, Sb, Hg, Tl, Pb, Bi, Po, V, Ir, Pt, Au, Re, W, Pd, Rh, Ta, Ag, Ru, Hf, Os, Zr, Nb, and Mo. The one or more additional alloying elements preferably have a lower concentration in the alloy than the rare earth element when the one or more additional alloying elements are selected from the group consisting of Ir, Pt, Au, Re, W, Pd, Rh, Ta, Ag, Ru, Hf, Os, Zr, Nb, and Mo. It is advantageous for the radiopacity of the nickel-titanium alloy to in the range of from greater than about 1.2 to about 5 times that of the near-equiatomic binary nickel-titanium alloy when exposed to radiation having an energy in the range of from 15 keV to 150 keV. Preferably, the radiation has a peak intensity at an energy in the range of from 30 keV to 60 keV. It is also preferred that the nickel-titanium alloy has a lower temperature phase and a higher temperature phase, wherein strain introduced in the nickel-titanium alloy in the lower temperature phase is recovered upon a phase transformation to the higher temperature phase. The lower temperature phase is preferably martensite and the higher temperature phase is preferably austenite. It is also preferred that the alloy has an austenite finish temperature in the range of from about −15° C. to about 37° C., and the alloy may further include an intermediate temperature R-phase. Preferably, the nickel-titanium alloy has an ultimate tensile strength of at least about 1350 MPa and is biocompatible.

According to another embodiment, the nickel-titanium alloy includes nickel at a concentration of from about 34 at. % to about 60 at. %, titanium at a concentration of from about 34 at. % to about 60 at. %, and at least one rare earth element at a concentration of from about 2.5 at. % to about 7.5 at. %. Preferably, the at least one rare earth element is selected from the group consisting of La, Pr, Nd, Pm, Sm, Eu, Gd, Tb, Dy, Ho, Er, Tm, Yb, Lu, Ac, Th, Pa, and U. The nickel-titanium alloy has a radiopacity greater than that of a near-equiatomic binary nickel-titanium alloy and further includes at least one additional alloying element at a concentration of no more than about 4.9 at. %, Preferably, the additional alloying element being selected from the group consisting of Cr, Co, Fe, and Pd. It is also advantageous for the alloy to be superelastic with an austenite finish temperature at or below about 37° C. Preferably, the nickel-titanium alloy includes a recoverable strain of at least about 0.5% upon removal of a deforming stress at or below body temperature.

According to another embodiment, the nickel-titanium alloy includes from about 50 at. % to about 56 at. % nickel; from about 40 at. % to about 46 at. % titanium; from about 0.1 at. % to about 4 at. % Er; and up to about 1 at. % at least one transition metal, wherein the at least one transition metal is selected from the group consisting of Cr, Fe, Co, and Pd. Preferably, the nickel-titanium alloy has a radiopacity of from about 1.2 to about 5 times greater than that of a near-equiatomic binary nickel-titanium alloy when exposed to radiation having an energy in the range of from 15 keV to 150 keV. The radiation may have a peak intensity at an energy in the range of from 30 keV to 60 keV. It is preferable that the nickel-titanium alloy is superelastic with an austenite finish temperature in the range of from about −15° C. to about 37° C. The nickel-titanium alloy also preferably has an ultimate tensile strength of at least about 1350 MPa and is biocompatible.

According to another embodiment, the nickel-titanium alloy includes from about 50 at. % to about 56 at. % nickel; from about 40 at. % to about 46 at. % titanium; from about 0.1 at. % to about 4 at. % Er; and up to about 1 at. % at least one transition metal, wherein the at least one transition metal is selected from the group consisting of Cr, Pd, Co, and Fe. Preferably, the nickel-titanium alloy has a radiopacity of about 1.2 to about 5 times greater than that of a near-equiatomic binary nickel-titanium alloy when exposed to radiation having an energy in the range of from 15 keV to 150 keV. The radiation preferably has a peak intensity at an energy in the range of from 30 keV to 60 keV. It is also preferred that the nickel-titanium alloy has a lower temperature phase and a higher temperature phase, wherein strain introduced in the nickel-titanium alloy in the lower temperature phase is recovered upon a phase transformation to the higher temperature phase. The lower temperature phase may be martensite, and the higher temperature phase may be austenite. The alloy may further comprise an intermediate temperature R-phase. Preferably, the nickel-titanium alloy has an austenite finish temperature in the range of from about −15° C. to about 37° C. and an ultimate tensile strength of at least about 1350 MPa. It is also preferred that the nickel-titanium alloy is biocompatible.

According to one embodiment, the medical device includes at least one component comprising a nickel-titanium alloy including from about 34 at. % to about 60 at. % nickel, from about 34 at. % to about 60 at. % titanium, and from about 0.1 at. % to about 15 at. % at least one rare earth element, wherein the at least one rare earth element is selected from the group consisting of La, Pr, Nd, Pm, Sm, Eu, Gd, Tb, Dy, Ho, Er, Tm, Yb, Lu, Ac, Th, Pa and U. Preferably, the nickel-titanium alloy has a radiopacity greater than that of a near-equiatomic binary nickel-titanium alloy. It is also preferred that the alloy is superelastic, and that the component is a self-expandable stent.

According to another embodiment, the medical device includes at least one component comprising a nickel-titanium alloy including from about 34 at. % to about 60 at. % nickel; from about 34 at. % to about 60 at. % titanium; from about 0.1 at. % to about 10 at. % at least one rare earth element; and at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U. Preferably, the nickel-titanium alloy has a radiopacity greater than that of a near-equiatomic binary nickel-titanium alloy and is superelastic. The component may be a self-expandable stent.

According to another embodiment, the medical device includes at least one component comprising a nickel-titanium alloy including nickel at a concentration of from about 34 at. % to about 60 at. %, titanium at a concentration of from about 34 at. % to about 60 at. %, and at least one rare earth element at a concentration of from about 0.1 at. % to about 15 at. %, wherein the at least one rare earth element is selected from the group consisting of La, Pr, Nd, Pm, Sm, Eu, Gd, Tb, Dy, Ho, Er, Tm, Yb, Lu, Ac, Th, Pa and U. Preferably, the component includes at least one of a wire and a cannula. It is also preferred that the concentration of the at least one rare earth element is from about 2.5 at. % to about 7.5 at. %. The nickel-titanium alloy preferably has a radiopacity greater than that of a near-equiatomic binary nickel-titanium alloy and is superelastic with an austenite finish temperature at or below about 37° C.

According to another embodiment, the medical device is radiopaque and includes at least one component comprising a nickel-titanium alloy including nickel at a concentration of from about 34 at. % to about 60 at. %, titanium at a concentration of from about 34 at. % to about 60 at. %, and at least one rare earth element at a concentration of from about 0.1 at. % to about 15 at. %, wherein the at least one rare earth element is selected from the group consisting of La, Pr, Nd, Pm, Sm, Eu, Gd, Tb, Dy, Ho, Er, Tm, Yb, Lu, Ac, Th, Pa and U. The nickel-titanium alloy comprises a radiopacity greater than that of a near-equiatomic binary nickel-titanium alloy, and the nickel-titanium alloy further comprises a recoverable strain of at least about 0.5% upon removal of a deforming stress at or below body temperature. Preferably, the recoverable strain is in the range of from about 2% to about 10%. It is also preferred that the nickel-titanium alloy is superelastic and has an austenite finish temperature at or below about 37° C.

A method of using a medical device has also been described herein. According to one aspect, the method includes providing a medical device having at least one component comprising a nickel-titanium alloy including from about 34 at. % to about 60 at. % nickel, from about 34 at. % to about 60 at. % titanium, and from about 0.1 at. % to about 15 at. % at least one rare earth element. Preferably the at least one rare earth element is selected from the group consisting of La, Pr, Nd, Pm, Sm, Eu, Gd, Tb, Dy, Ho, Er, Tm, Yb, Lu, Ac, Th, Pa and U. The medical device is then delivered to a treatment site within the patient. The method may further include loading the medical device into a delivery system and inserting the medical device into the patient after loading the medical device into a delivery system. Preferably, the nickel-titanium alloy has a radiopacity greater than that of a near-equiatomic binary nickel-titanium alloy. It is also preferred that the nickel-titanium alloy is superelastic. The component may be a stent, a retrieval device, and an embolic protection filter.

According to another aspect, the method of using the medical device may include providing a medical device including at least one component comprising a nickel-titanium alloy having from about 34 at. % to about 60 at. % nickel, from about 34 at. % to about 60 at. % titanium, from about 0.1 at. % to about 10 at. % at least one rare earth element, and at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U. The medical device is delivered to a treatment site within the patient. The method may further include loading the medical device into a delivery system and inserting the medical device into the patient. Preferably, the nickel-titanium alloy has a radiopacity greater than that of a near-equiatomic binary nickel-titanium alloy. It is also preferred that the nickel-titanium alloy is superelastic. The component may be a stent, a retrieval device, and an embolic protection filter.

A method of imaging a medical device within a patient also has been described herein. According to one aspect, the method includes delivering a medical device having at least one component comprising a nickel-titanium alloy including from about 34 at. % to about 60 at. % nickel, from about 34 at. % to about 60 at. % titanium, and from about 0.1 at. % to about 15 at. % at least one rare earth element to a treatment site within a patient. The at least one rare earth element is selected from the group consisting of La, Pr, Nd, Pm, Sm, Eu, Gd, Tb, Dy, Ho, Er, Tm, Yb, Lu, Ac, Th, Pa and U. The patient is exposed to radiation having an energy in the range of from 15 keV to 150 keV, thereby imaging the medical device. Preferably, the radiation has a peak intensity at an energy in the range of from 30 keV to 60 keV. Exposing the patient to radiation preferably includes providing an x-ray source in opposition to the patient and at least one filter between the x-ray source and the patient, wherein the x-ray source comprises a tube voltage in the range of from 60 kVp to 150 kVp. Preferably, the filter is selected from the group consisting of a 2.5 mm aluminum filter, 0.1 mm copper filter, 0.2 mm copper filter, and 0.3 mm copper filter.

According to another aspect, the method of imaging the medical device includes delivering a medical device having at least one component comprising a nickel-titanium alloy including from about 34 at. % to about 60 at. % nickel, from about 34 at. % to about 60 at. % titanium, from about 0.1 at. % to about 10 at. % at least one rare earth element; and at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U to a treatment site within a patient. The patient is exposed to radiation having an energy in the range of from 15 keV to 150 keV, thereby imaging the medical device. Preferably, the radiation has a peak intensity at an energy in the range of from 30 keV to 60 keV. Exposing the patient to radiation preferably includes providing an x-ray source in opposition to the patient and at least one filter between the x-ray source and the patient, wherein the x-ray source comprises a tube voltage in the range of from 60 kVp to 150 kVp. Preferably, the filter is selected from the group consisting of a 2.5 mm aluminum filter, 0.1 mm copper filter, 0.2 mm copper filter, and 0.3 mm copper filter.

A method of making a medical device has also been described herein. According to one aspect, the method comprises forming a melt comprising from about 34 at. % to about 60 at. % nickel, from about 34 at. % to about 60 at. % titanium, and from about 0.1 at. % to about 15 at. % at least one rare earth element, wherein the at least one rare earth element is selected from the group consisting of La, Pr, Nd, Pm, Sm, Eu, Gd, Tb, Dy, Ho, Er, Tm, Yb, Lu, Ac, Th, Pa and U. The melt is cooled to form a solid, and the solid is formed into a component, thereby forming a medical device. Forming the solid into the component preferably includes hot working the solid into a first shape, and cold working the first shape into the component. Hot working the solid may include at least one of extruding, hot rolling, and forging. Cold working the first shape may include drawing or rolling. Forming the solid into a component preferably further includes annealing the component. The annealing may entail constraining the component in a final shape and heating the component at a temperature in the range of from about 350° C. to about 550° C. It may be advantageous to solution heat treat the solid at a temperature of at least about 1,000° C.

According to another embodiment, the method of making the medical device includes forming a melt comprising from about 34 at. % to about 60 at. % nickel, from about 34 at. % to about 60 at. % titanium, from about 0.1 at. % to about 10 at. % at least one rare earth element, at least one transition metal at a concentration of no more than about 4.9 at. %, wherein the at least one rare earth element is selected from the group consisting of Ce, La, Pr, Nd, Pm, Sm, Eu, Gd, Tb, Dy, Ho, Er, Tm, Yb, Lu, Ac, Th, Pa, and U. The melt is cooled to form a solid, and the solid is formed into a component, thereby forming a medical device. Forming the solid into the component preferably includes hot working the solid into a first shape, and cold working the first shape into the component. Hot working the solid may include at least one of extruding, hot rolling, and forging. Preferably, the solid receives a solution heat treatment prior to hot working. Cold working the first shape may include drawing or rolling. Forming the solid into a component preferably further includes annealing the component. The annealing may entail constraining the component in a final shape and heating the component at a temperature in the range of from about 350° C. to about 550° C. It may be advantageous to solution heat treat the solid at a temperature of at least about 1,000° C.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A nickel-titanium alloy comprising:
   nickel at a concentration of from about 34 at. % to about 60 at. %;
   titanium at a concentration of from about 34 at. % to about 60 at. %; and
   at least one rare earth element at a concentration of from about 2.5 at. % to about 15 at. %,
   wherein the at least one rare earth element is selected from the group consisting of La, Pr, Nd, Pm, Sm, Eu, Gd, Tb, Dy, Ho, Er, Tm, Yb, Lu, Ac, Th, Pa, and U, and
   wherein the nickel-titanium alloy comprises an austenite finish temperature at or below 37 ° C., the nickel-titanium alloy being superelastic at body temperature.

2. The nickel-titanium alloy of claim 1 wherein the concentration of the rare earth element is from about 2.5 at. % to about 7.5 at. %.

3. The nickel-titanium alloy of claim 1, further comprising at least one additional alloying element at a concentration of at least about 0.1 at. % up to about 14.9 at. %.

4. The nickel-titanium alloy of claim 3, wherein the concentration of the additional alloying element is no more than about 4.9 at. % and the additional alloying element is selected from the group consisting of Cr, Co, Fe, and Pd.

5. The nickel-titanium alloy of claim 1 having a radiopacity greater than that of a near-equiatomic binary nickel-titanium alloy.

6. The nickel-titanium alloy of claim 5, wherein the radiopacity of the nickel-titanium alloy is in the range of from greater than about 1 to about 8 times that of the near-equiatomic binary nickel-titanium alloy when exposed to radiation having an energy in the range of from 15 keV to 150 keV.

7. The nickel-titanium alloy of claim 1, wherein the nickel-titanium alloy comprises an x-ray contrast in the range of from greater than 1 to about 2 times that of a near-equiatomic binary nickel-titanium alloy when exposed to radiation having an energy in the range of from 40keV to 110keV.

8. The nickel-titanium alloy of claim 1 comprising a recoverable strain of at least about 0.5 % upon removal of a deforming stress at body temperature.

9. The nickel-titanium alloy of claim 1 having a radiopacity greater than that of a near-equiatomic binary nickel-titanium alloy, the concentration of the rare earth element being from about 2.5 at. % to about 7.5 at. %, and further comprising at least one additional alloying element at a concentration of at least about 0.1 at. % to no more than about 4.9 at. %, the additional alloying element being selected from the group consisting of Cr, Co, Fe, and Pd, wherein the nickel-titanium alloy is superelastic and has an austenite finish temperature at or below 37° C.

10. A medical device comprising at least one component comprising a nickel-titanium alloy including nickel at a concentration of from about 34 at. % to about 60 at. %, titanium at a concentration of from about 34 at. % to about 60 at. %, and at least one rare earth element at a concentration of from about 2.5 at. % to about 15 at. %, wherein the at least one rare earth element is selected from the group consisting of La, Pr, Nd, Pm, Sm, Eu, Gd, Tb, Dy, Ho, Er, Tm, Yb, Lu, Ac, Th, Pa and U, and
   wherein the nickel-titanium alloy comprises an austenite finish temperature at or below 37° C., the nickel-titanium alloy being superelastic at body temperature.

11. The medical device of claim 10, wherein the component includes at least one of a wire and a cannula.

12. The medical device of claim 10, wherein the concentration of the at least one rare earth element is from about 2.5at. % to about 7.5at. % and the nickel-titanium alloy has a radiopacity greater than that of a near-equiatomic binary nickel-titanium alloy.

13. A radiopaque medical device comprising at least one component comprising a nickel-titanium alloy including nickel at a concentration of from about 34at. % to about 60at. %, titanium at a concentration of from about 34at.% to about 60at. %, and at least one rare earth element at a concentration of from about 2.5at. % to about 15at. %, wherein the at least one rare earth element is selected from the group consisting of La, Pr, Nd, Pm, Sm, Eu, Gd, Tb, Dy, Ho, Er, Tm, Yb, Lu, Ac, Th, Pa and U, whereby the nickel-titanium alloy comprises a radiopacity greater than that of a near-equiatomic binary nickel-titanium alloy, and wherein the nickel-titanium alloy further comprises a recoverable strain of at least about 0.5 % upon removal of a deforming stress at body temperature, the nickel-titanium alloy being superelastic at body temperature.

14. The radiopaque medical device of claim 13, wherein the nickel-titanium alloy has an austenite finish temperature at or below 37° C.

15. The radiopaque medical device of claim 13, wherein the recoverable strain is in the range of from about 2 % to about 10 %.

16. The nickel-titanium alloy of claim 1, wherein the concentration of titanium is from about 44 at. % to about 60 at. %.

17. The medical device of claim 10, wherein the medical device is selected from the group consisting of: a stent, a stent graft, a wire guide, a radiopaque marker or marker band, a catheter, an introducer sheath, an orthodontic arch wire, a vascular plug, an embolic protection filter, and a manipulation, retrieval or occlusive device.

18. The nickel-titanium alloy of claim 10, wherein the concentration of titanium is from about 44 at. % to about 60 at. %.

19. The radiopaque medical device of claim 15, wherein the radiopaque medical device is selected from the group consisting of: a stent, a stent graft, a wire guide, a radiopaque marker or marker band, a catheter, an introducer sheath, an orthodontic arch wire, a vascular plug, an embolic protection filter, and a manipulation, retrieval or occlusive device.

20. The nickel-titanium alloy of claim 15, wherein the concentration of titanium is from about 44 at. % to about 60 at. %.

* * * * *